United States Patent
Arany et al.

(10) Patent No.: US 9,731,012 B2
(45) Date of Patent: Aug. 15, 2017

(54) LASER-ACTUATED THERAPEUTIC NANOPARTICLES

(71) Applicant: President and Fellows of Harvard College, Cambridge, MA (US)

(72) Inventors: Praveen Arany, Cambridge, MA (US); David J. Mooney, Sudbury, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 98 days.

(21) Appl. No.: 14/389,136

(22) PCT Filed: Mar. 12, 2013

(86) PCT No.: PCT/US2013/030493
§ 371 (c)(1),
(2) Date: Sep. 29, 2014

(87) PCT Pub. No.: WO2013/148158
PCT Pub. Date: Oct. 3, 2013

(65) Prior Publication Data
US 2015/0065685 A1  Mar. 5, 2015

Related U.S. Application Data

(60) Provisional application No. 61/617,822, filed on Mar. 30, 2012.

(51) Int. Cl.
*A61K 47/48* (2006.01)
*A61K 41/00* (2006.01)
*A61K 38/18* (2006.01)
*A61K 38/00* (2006.01)

(52) U.S. Cl.
CPC ...... *A61K 41/0042* (2013.01); *A61K 38/1841* (2013.01); *A61K 47/48284* (2013.01); *A61K 47/48884* (2013.01); *A61K 38/00* (2013.01)

(58) Field of Classification Search
CPC .......... A61K 47/48884; A61K 41/0042; A61K 38/00; A61K 38/1841; A61K 47/48284

USPC .................................. 424/400; 514/1.1, 8.9
See application file for complete search history.

(56) References Cited

U.S. PATENT DOCUMENTS

| | | | |
|---|---|---|---|
| 2010/0183728 A1* | 7/2010 | Desai | A61K 9/0019 424/489 |
| 2010/0196490 A1* | 8/2010 | Desai | A61K 9/0019 424/489 |
| 2010/0226996 A1* | 9/2010 | Desai | A61K 9/0019 424/499 |
| 2012/0076862 A1* | 3/2012 | Desai | A61K 31/337 424/491 |
| 2013/0231287 A1* | 9/2013 | Nacharaju | A61K 47/48215 514/15.2 |

OTHER PUBLICATIONS

Arany et al., Wound Repair Regen, 15(6):866-74. (2007) "Activation of latent TGF-beta1 by low-power laser in vitro correlates with increased TGF-beta1 levels in laser-enhanced oral wound healing."
Arany, P.R., Proceedings of Light-Activated Tissue Regeneration and Therapy Conference Lecture Notes in Electrical Engineering vol. 12 , pp. 207-212. (2008) "Photobiomodulation by Low Power Laser Irradiation Involves Activation of Latent TGF-β1".
Jeong et al., Theranostics, 1:230-239, (2011). "Photosensitizer-Conjugated human serum albumin nanoparticles for effective photodynamic therapy."
Kratz et al., J Control Release 132(3):171-83. (2008). "Albumin as a drug carrier: design of prodrugs, drug conjugates and nanoparticles."
Lu et al., J Control Release, 107(3):428-48. (2005) "Cationic albumin-conjugated pegylated nanoparticles as novel drug carrier for brain delivery."

* cited by examiner

*Primary Examiner* — David Lukton
(74) *Attorney, Agent, or Firm* — McCarter & English, LLP; Maria Laccotripe Zacharakis; Deborah L. Nagle

(57) ABSTRACT

The invention provides compositions and methods for laser actuated drug delivery. Compositions comprise serum albumin based particles conjugated with therapeutic agents which cab become bioavailable upon actuation of the particles by light, e.g. low power laser.

17 Claims, 24 Drawing Sheets

DISTANCE: 789.68 μm
MINIMUM ALTITUDE: -3.3 nm
MAXIMUM ALTITUDE: 31.0 nm
AVERAGE ALTITUDE: 2.9 nm

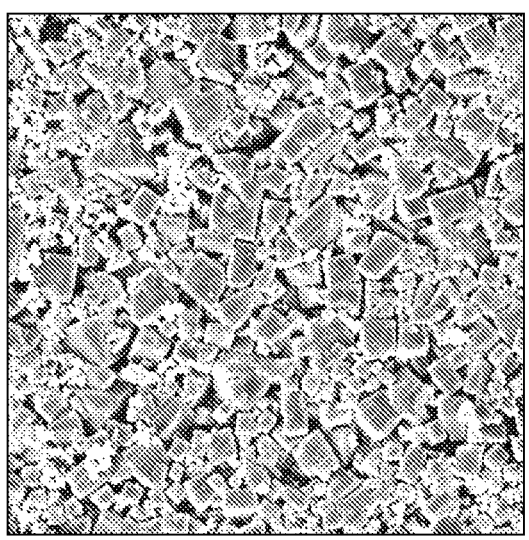
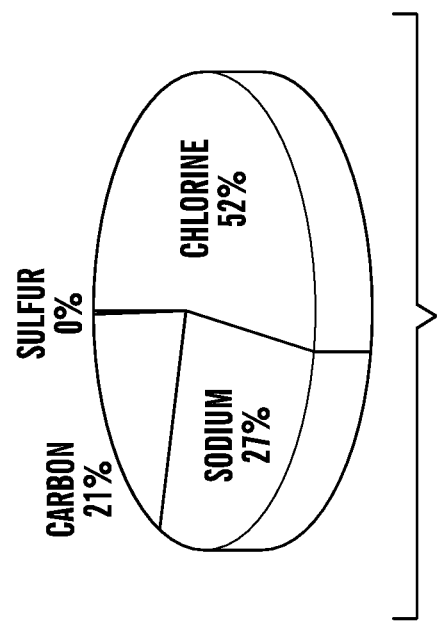
FIG. 15A
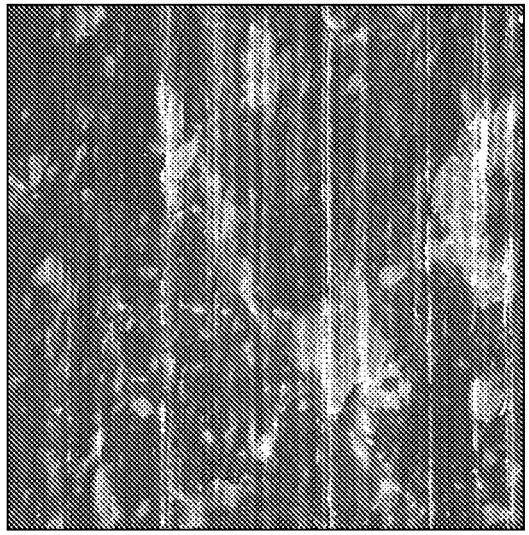
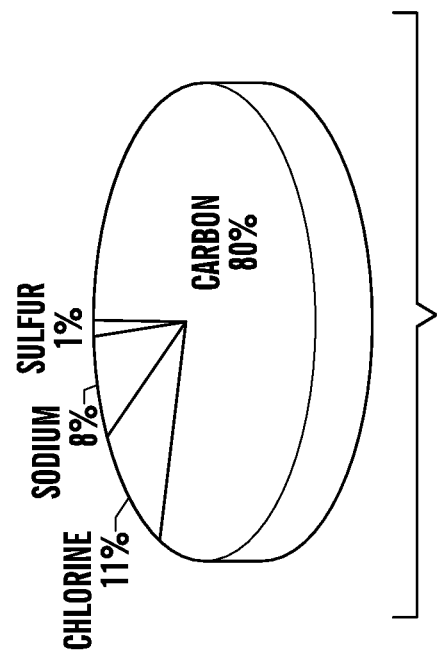
FIG. 15B

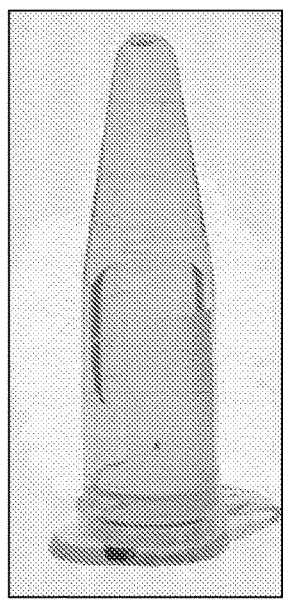 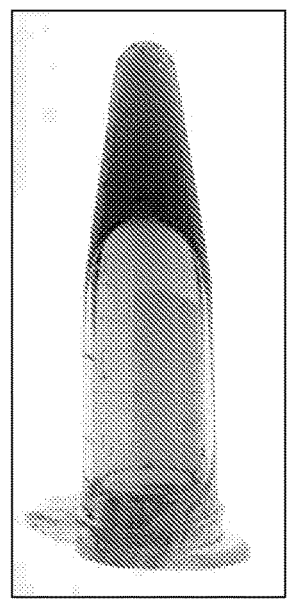 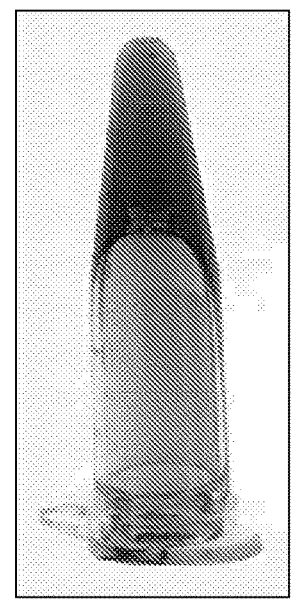
*FIG. 16A*   *FIG. 16B*   *FIG. 16C*
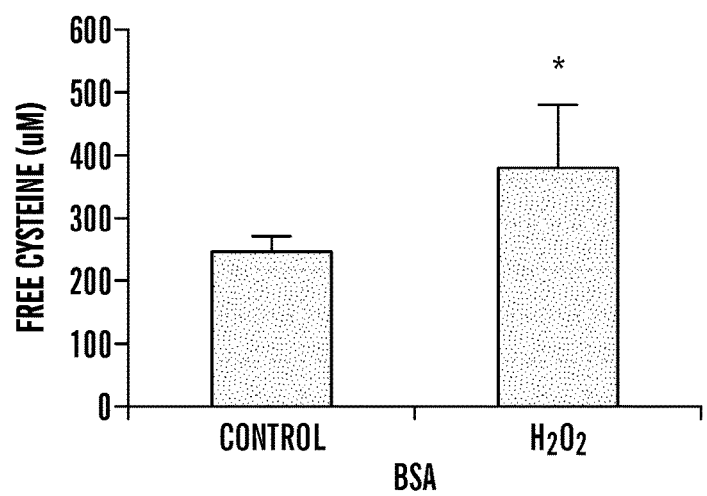
*FIG. 17*

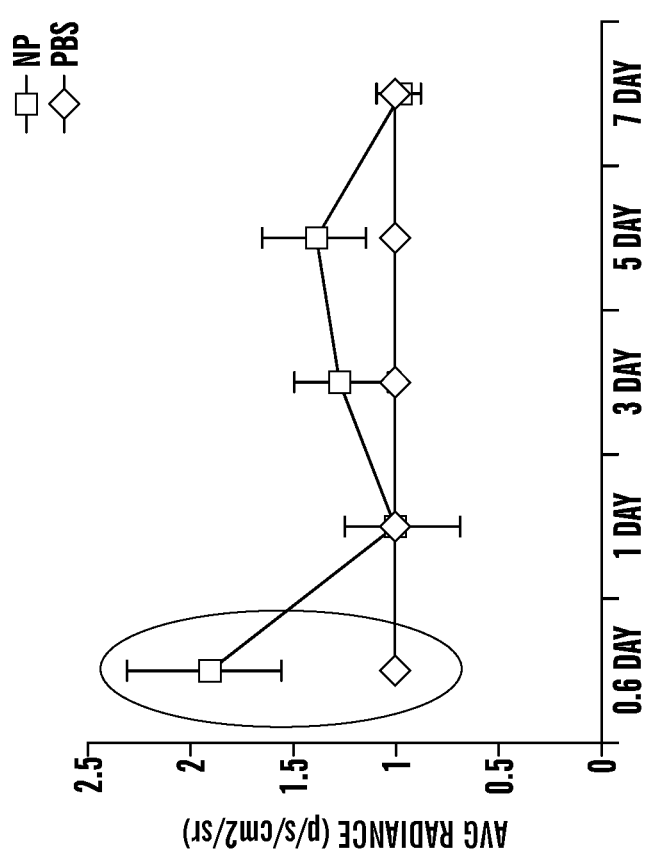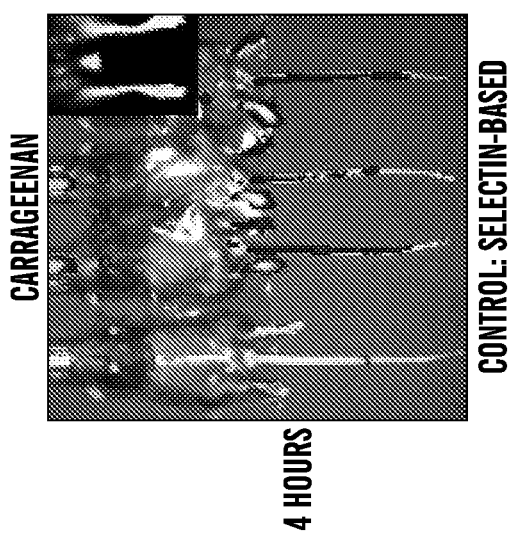
FIG. 32B

TGFβ1 BSA NP

LASER-ACTUATED THERAPEUTIC NANOPARTICLES

CROSS REFERENCE TO RELATED APPLICATIONS

This application is a 35 U.S.C. §371 National Phase Entry Application of International Application No. PCT/US2013/030493 filed Mar. 12, 2013, which designates the U.S., and which claims benefit under 35 U.S.C. §119(e) of the U.S. Provisional Application No. 61/617,822, filed Mar. 30, 2012, the content of which is incorporated herein by reference in its entirety.

GOVERNMENT SUPPORT

This invention was made with government support under Grant No. R01 DE019917 awarded by the National Institutes of Health. The U.S. government has certain rights in the invention.

TECHNICAL FIELD

The present disclosure relates to molecular biology, providing compositions and methods for controlled actuation of therapeutic agents.

BACKGROUND

There remains a need for compositions and methods for selective delivery of active agents such as biomolecules, small molecules, or proteins, in vivo.

SUMMARY

Albumin nanoparticles are considered an ideal candidate for drug delivery due to the high degree of biocompatibility, ability to target drugs to specific sites, and simple preparation. In order to overcome the pharmacokinetic limitations and the need for high concentrations of a drug, therapeutic candidates have been incorporated with nanoparticle systems. The major limitation of previous albumin nanoparticle delivery systems is that they depend on their biodegradation by endogenous enzymatic activity to release their therapeutic payload. The present invention provides for a controlled release albumin nanoparticle delivery system that uses low-power lasers as an actuator. This delivery system can be used to deliver a wide variety of therapeutically relevant active agents including small molecules and proteins.

As a model system, serum albumin nanoparticles were conjugated with TGF-β1 in efforts to harnesses both the natural targeting ability of albumin to sites of inflammation and the anti-inflammatory therapeutic benefits of TGF-β1. Albumin nanoparticles were fabricated using an ethanol coacervation process and conjugated with TGF-β1 (BSA: TGF-β1 NP). Biochemical assays demonstrate the ability for laser to modulate the conformation of albumin via reactive oxygen species (ROS) generation. An ELISA and Mv1Lu reporter cell line showed increased bioavailability of TGF-β1 upon laser actuation. To evaluate this delivery system for immune modulation, a macrophage cell line, RAW293, and primary bone marrow dendritic cells (BMDCs) were stimulated with lipopolysaccharide (LPS) and treated with BSA: TGF-β1 NP with or without laser irradiation. Laser actuated BSA:TGF-β1 NPs were found to significantly suppress NFκB reporter activity while also suppressing IL-1b and TNF-α levels compared with basal BSA:TGF-β1 NPs. The present invention provides for the fabrication and utility of laser-actuated serum albumin nanoparticles, e.g., BSA:TGF-β1 NPs, as an effective therapeutic strategy for delivery of an active agent.

BRIEF DESCRIPTION OF THE DRAWINGS

FIGS. 15A and 15B show analysis of BSA NPs with and without the presence of salt. SEM imaging of lypholized BSA NPs dialyzed against 1 M NaCl (FIG. 15A) and diH20 (FIG. 15B) at 500×. Below each is the elemental composition by weight percent of each sample using EDS.

FIGS. 16A-16C show that protein is present in the BSA NPs. A BCA was used to determine the presence of protein in sample aggregates. The negative control (FIG. 16A) is PBS and the positive control (FIG. 16C) is a BSA (10 mg/mL). A robust color change was observed in BSA NPs (FIG. 16B).

FIG. 17 is a bar graph of data showing ROS increases free cysteine concentration in BSA. Treatment of BSA (10 mg/mL) with $H_2O_2$ (10 µM) followed by free cysteines with IAEDANs dye and quantitation by microplate reader (n=4, * indicates p<0.05).

FIGS. 32A-32C show that BSA NPs utilize EPR effects to home to sites of inflammation. FIG. 32A, carrageenan (7 mg/ml, 100 ul per site) was used to induce acute inflammation in mice paws. After 4 hours, polystyrene beads (Fluorescent, 250 nm, Life Sciences Inc) were injected intravenous to observe localization to inflammation site due to Enhanced Permeability and Retention (EPR) effect. In test animals, BSANPs tagged with Alexa 780 nm (10 mg/ml, 50 ul) were injected intravenous tail vein and observed to localize to these inflammatory sites within 5 minutes. The images on the left show the increased fluorescence signal of localized nanoparticles and the panel on the right demonstrates the kinetics of NP accumulation post injection. FIG. 32B, in a similar carrageenan-induced EPR model, a commercially available selectin-based probe (Caliper) was used to test homing of nanoparticles. The images on the left show the increased fluorescence signal of localized nanoparticles, the first mouse is a control (no NP injection) and inset shows the redness in the left paw associated with carrageenan injection. The panel on the right demonstrates the kinetics of NP injections at 1, 3, 5 and 7 days and imaging demonstrating there is minimal residual accumulation at these sites in the absence of acute inflammation. FIG. 32C, in a distinct injury model, Notexin (4 ug/ml, 10 ul) was injected in the Tibialis muscle and a myeloperoxidase-based probe was used to detect the sub-acute inflammation at 3 days. Intravenous injection of the BSA NPs resulted in a similar increase in accumulation due to peak EPR effects at 3 days.

FIG. 33A is a schematic of the experimental outline to evaluate the ability of the TGF-β1:BSA NPs to deliver to a localized site. Two scaffolds were seeded with TGF-β reporter cells overnight and implanted in rat dorsum along with subcutaneous injection of carrageenan locally. TGF-β1:BSA NPs were injected intravenous and laser treatment was performed on right side. After 24 hours, luciferase imaging was performed. FIG. 33B, show the cell seeded scaffolds that were fixed and imaged by SEM, inset show macroporous scaffold structure permitting easy access to trafficking by cells and nanoparticles. FIG. 33C shows luciferase imaging of the rat with two reporter seeded scaffolds that had the right side laser treated demonstrating the increased signal correlating with activation of the NP. The left side also shows some minimal signal probably due to localized TGF-β during injury-implantation and possibly some diffusion from the other laser-treated side.

FIG. 34A is a schematic showing the experimental outline to evaluate the ability of the laser actuated TGF-β1:BSA NPs to induce a local regulatory T cell response. A specific sub-population of T regulatory cells, FoxP3 positive induced by TGF-β1 were assessed in this experiment. FoxP-GFP mice were implanted with PLG scaffolds incorporating PEI. On day 5 and 10 following implantation, TGFβ1:BSA NPs were injected iv and laser treatment was performed on one site. As controls, PBS was injected and laser treatment was performed. All mice were sacrificed on day 12 and tissues were harvested for analyses by cryosections and molecular assays. FIG. 34B shows cryosections, from mice tissue, stained with DAPI and assessed with fluorescence microscopy. Tissues from TGF-β1:BSA NPs and laser treatment demonstrate GFP positive cells indicating that TGF-β1 was specifically delivered to the local scaffold site.

DETAILED DESCRIPTION

Albumin nanoparticles (NPs) are naturally biodegradable and non-toxic, both bovine serum albumin (BSA) and human serum albumin (HSA). NPs have been studied as drug carriers to improve the pharmokinetic and biodistribution profiles of a therapeutic agent. Not only do albumin NPs improve drug delivery, the accumulation of albumin in solid tumors and inflammatory sites uses endogenous albumin transport to allow for greater specificity in local drug targeting. Clinically, albumin has made a tremendous impact on drug delivery. In 2005, Abraxane® (Paclitaxel injection), a 130 nm albumin-paclitaxel NP drug to treat solid tumors, was FDA approved for the treatment of metastatic breast cancer, demonstrating the growing potential of albumin NPs as an effective drug carrier. Clinical studies demonstrated a 50% higher drug dose could be administered with Abraxane® (Paclitaxel injection) compared to standard paclitaxel treatment because of the reduced toxicity profile of the chemotherapy agents and the ability for albumin NPs to transport the drug to tumors. Kratz & Elsadek, 2011; Hawkins et al., 60 Adv. Drug Deliv. Rev. 876 (2008).

Current albumin NP-based drug carriers rely on biodegradability and protease activity to release the drug from the albumin. Although exploitation of the surface properties of albumin NPs can allow for target-specific release, new modalities are being explored for controlled drug delivery. In addition to degradation, heat and light have been researched as forms of physical energy in nanoparticle drug delivery systems that can induce local drug delivery and therapeutic benefits. De Jong & Borm, 3 Intl. J. Nanomed. 133 (2008); Jahanshahi, 7 African J. Biotechnol. 4926 (2008).

Figure 1:
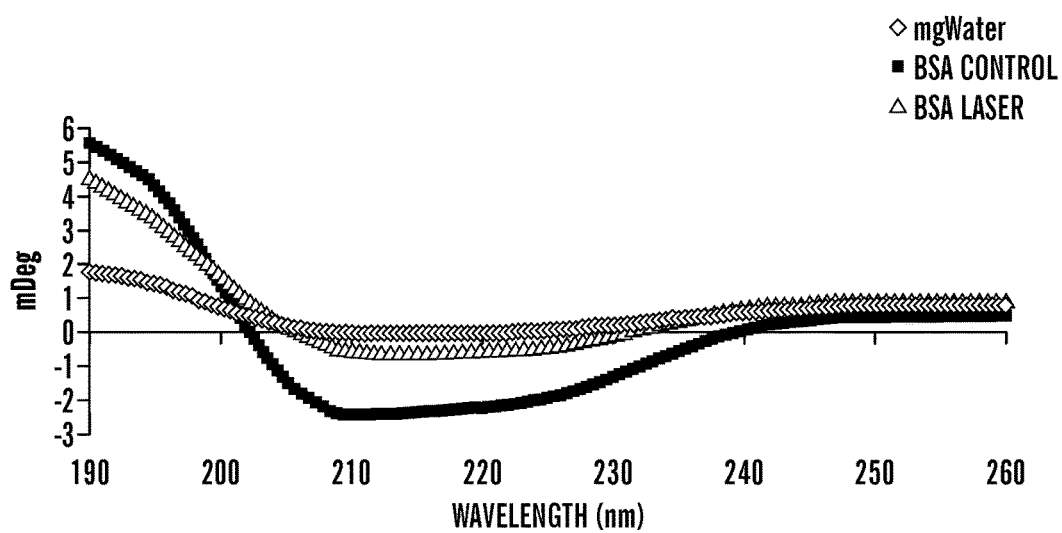
FIG. 1 demonstrates that laser irradiation changes the conformation of BSA. CD analysis of laser irradiated BSA shows a change in conformational structure of BSA upon laser irradiation.
Figure 2:
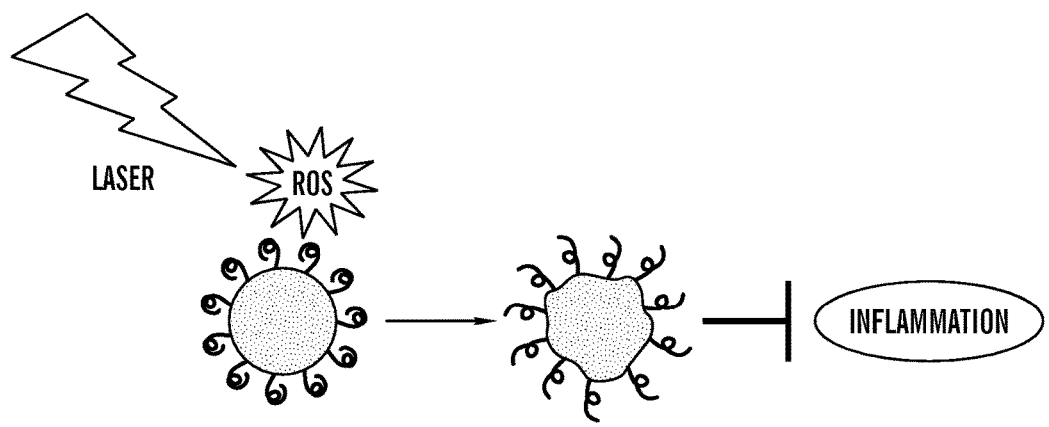
FIG. 2 is a schematic depiction of how LPL generated ROS can change the conformation of BSA NPs. The conformational change allows conjugated TGF-β1 to become more biologically available and have anti-inflammatory effects.

During circular dichorism (CD), a form of light absorbance spectroscopy, low power lasers (LPL) were noted to modulate the conformational structure of bovine serum albumin (FIG. 1). The present invention provides for a laser-actuated albumin NP drug delivery system to control the bioavailability of an incorporated active (therapeutic) agent. Low power laser (LPL) irradiation generates reactive oxygen species (ROS) that modulates albumin NP conformation and increases bioavailability of the active agent, for example, transforming growth factor beta-1 (TGF-β1) (FIG. 2).

Further by way of introduction, albumin has attracted a great deal of interest as an ideal drug carrier. Albumin is the most abundant plasma protein in the body with a molecular weight of 66.5 kDa, has an effective diameter of 7.2 nm, and has an average half-life of 19 days. In addition to these desirable properties, it is highly biocompatible because it is produced in the liver, and is extremely biochemically robust: it is stable in pH 4-9, soluble in 40% ethanol, and can be heated at 60° C. for up to 10 hours without negative effects on its biological functions. Kratz, 132 J. Contr. Release 171 (2008).

Figure 3:
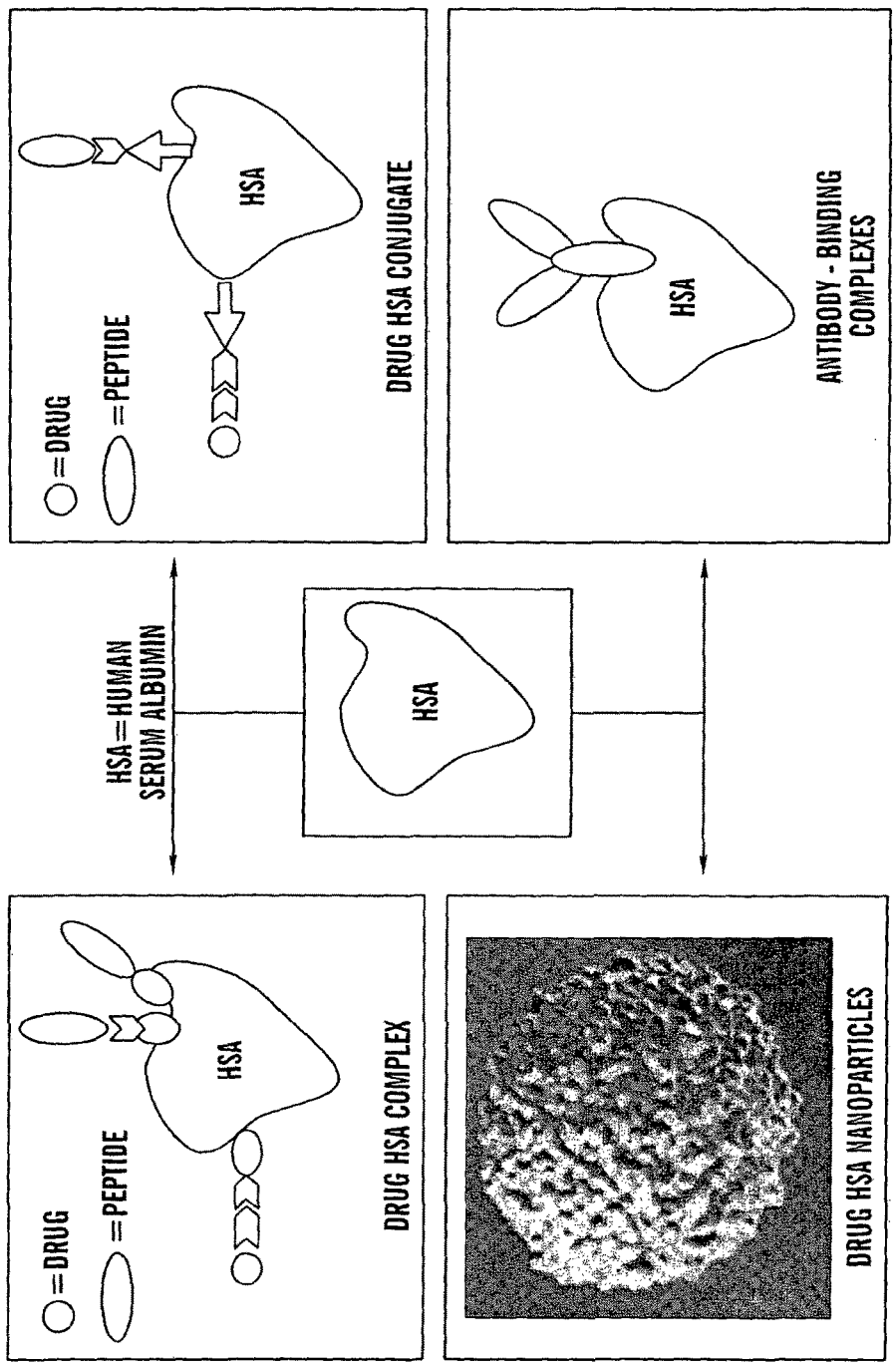
FIG. 3 shows depictions of albumin as a drug carrier. Applications of albumin as a drug carrier for developed drug-, peptide-, or antibody-based drugs as conjugates, complexes, or nanoparticles. Figure adapted from Kratz & Elsadek, J. Control Release (2011).

When selecting an appropriate drug carrier, in addition to cost and availability, important properties to consider include high accumulation in the target tissue, low uptake rates in normal tissue, low toxicity, ability to bind drugs, and release of the drug in the target tissue. De Jong & Borm, 2008; Wunder et al., 170 J. Immunol. 4793 (2003). Albumin, with its abundance in circulation, biodegradability, biocompatibility, and long half-life meets many of the necessary properties of an ideal drug carrier. Albumin has been investigated as a drug carrier in four primary ways: drug-albumin complexes, drug-albumin conjugates, drug-albumin NPs, and drug-albumin ligand and antibody conjugates and complex (FIG. 3). Katz & Elsadek, 2011; Elsadek & Katz, 157 J. Contr. RElease 4 (2012). A complex implies physical binding while a conjugate implies chemical binding of the payload to the albumin.

Albumin as a drug carrier has been used to overcome the inadequate pharmacokinetic properties of many therapeutic agents and to improve the drug targeting properties of small-molecules, peptides, and proteins. The potential targeting ability of albumin-based drug carriers have been extensively explored for cancer and rheumatic arthritis (RA) applications because of the natural accumulation of albumin in malignant and inflamed tissues. Albumin is thought to accumulate in tumor areas because of the enhanced permeability and retention (EPR) effect. Katz, 2008; Park, 157 J. Contr. Release 3 (2012). In addition to the EPR effect in solid tumors, uptake of albumin also seems to be mediated by the gp60 transcytosis pathway, located on cell surface of endothelial cells. Katz & Elsadek, 2011; Elsadek & Katz, 2012. It has been hypothesized that albumin is a major source of energy and nutrition for tumor growth, contributing to the high albumin metabolism rates in tumors. Katz & Elsadek, 2011; Wunder et al., 2003. In RA, the synovial lining layer of joints becomes highly proliferative and blood-joint barrier permeability is up to six times higher, contributing to the high albumin accumulation and metabolism in inflamed joints. Wuner et al., 2003; Levick, 24 Arthritis, 1550 (1981). Exploiting the targeting ability of albumin to malignant and inflamed tissue, methotrexate (MTX, a known anti-inflammatory drug) was coupled to albumin for the treatment of cancer and RA to enhance targeting, reduce toxicity and improve pharmacokinetics of the drug. Wunder et al., 2003; Fiehn et al., 43 Rheumatol. 1097 (2004); Stehle et al. 8 Anticancer Drugs 835 (1997); Stehle et al., 8 Anticancer Drugs 677 (1997).

Therapeutic applications for albumin-based drug carriers have been explored in diabetes and viral diseases as well, in order to exploit the multiple binding sites and long half-life of albumin to protect the drug from rapid degradation and excretion from circulation. Due to the unique availability of albumin's cysteine-34, which is not found on the majority of circulating serum proteins, albumin conjugates or albumin-binding prodrugs and peptides were first developed to be able to quickly and selectively bind to this site on endogenous and exogenous albumin. Kratz, 2008. For example, a glucagon-like peptide 1 (GLP-1) derivative with the ability to selectively bind to the cysteine-34 position of albumin was developed for the treatment of diabetes. Kim et al., 52 Diabetes 751 (2003). Others have focused their work on developing prodrugs that have the ability to bind to the cysteine-34 position of endogenous, circulating albumin, such as an MTX prodrug for in situ delivery to improve binding and create a cleavable bond between the drug and carrier to ensure specific release at the desired sites. Kratz, 2008; Fiehn et al., 67 Ann. Rheum. Did. 1188 (2008).

Nanoparticle-based delivery systems first emerged as a platform for drug delivery around 1970, in effort to allow for more specific drug targeting and delivery, reduce toxicity while maintaining therapeutic effects, and provide greater in vivo safety and biocompatibility. De Jong & Borm, 2008. NP drug carriers hold a great deal of promise because they have the potential to protect a drug from degradation, facilitate drug targeting to a specific site, effectively modulating and improving the pharmacokinetic properties and biodistribution profiles of a drug. In addition, the particle size and surface characteristics can be manipulated to improve targeting and release properties, and enhance drug transport. Jahanshahi, 2008. When fabricating NPs for drug delivery, size plays a critical role in the clearance rate, distribution, and bioavailability of the NP because large particles can be easily removed by the liver and spleen. Nanoparticles in the range of 100 nm to 200 nm are considered ideal to enhance their ability to escape the vascular system through the lining of blood vessels. Jahanshahi, 5 African J. Biotechnol. 1918 (2006); Langer et al., 257 Intl. J. Pharm. 169 (2003).

Among biodegradable colloid NP drug carriers, protein-based NP systems are attractive because not only are these class of nanomaterials biodegradable, they are also non-antigenic and non-toxic. Albumin NPs have been given special attention as a drug carrier due to albumin's ideal biocompatibility, targeting ability, and pharmacokinetic properties. The presence of a free thiol group, cysteine-34 allows albumin to form aggregates and form NPs. Elzoghby et al., 157 Contr. Release 168 (2012). The availability of thiol, amino, and carboxylic acid groups on the surface of albumin also allow for potential ligand binding and surface modifications. Jahanshahi, 2008; Elzoghby et al., 2012; Weber et al., 194 Intl. J. Pharm. 91 (2000). Furthermore, protein-based NPs are advantageous because they have greater stability during storage and in vivo cirulation, and are easy to scale up during manufacturing compared to other drug delivery platforms. Elzoghby et al., 2012.

Albumin NPs are prepared through a simple coacervation, or desolvation, process with ethanol using both bovine serum albumin (BSA) or human serum albumin (HSA). Slowly coacervating a protein solution with natural salts or alcohol to fabricate NPs was proposed previously. Marty et al., 53 Pharm. Acta Hely. 17 (1978). During the dropwise ethanol addition into an aqueous solution of albumin the protein begins to coacervate due to the limited solubility of albumin in ethanol, forming albumin particles. Elzoghby et al., 2012. In order to prevent albumin from redissolving again in water, the nanoparticles must be stabilized. Originally, glutaraldehyde (GA) had been used to cross-link the nanoparticles and stabilize the nanoparticles. Jahanshahi, 2006; Langer et al., 2003; Elzoghby et al., 2012; Weber et al., 2000; Wang et al., 25 Pharm. Res. 2896 (2008). Due to concerns regarding high toxicity of GA, however, other stabilizers including polyethylenimine (PEI) and poly-L-lysine (PLL) have been explored as suitable substitutes for GA cross-linking. Desai, 3 Nanomedicine 337 (2007).

The most successful albumin-based NP delivery system is the albumin-based nanoparticle technology ("nab-technology") developed by American Bioscience, Inc. Nab-technology passes HSA mixed with a drug under high pressure through a jet to form 100-200 nm drug albumin nanoparticles. As noted previously, a 130 nm nab-paclitaxel drug (Abraxane®) became the first nanotechnology based chemotherapeutic FDA drug approved for the treatment of metastatic breast cancer, demonstrating the growing potential of albumin NPs as an effective drug carrier. Hawkins, 2008; Elzoghby et al., 2012. Nab-technology takes advantage of albumin's ability to carry hydrophobic molecules and target tumor cells by binding to the endothelial gp60 cell-surface receptor and the albumin-binding protein, Secreted Protein, Acid and Rich in Cysteine (SPARC), which contributes to the NP's ability to transport drugs to tumors. Desai, 2007. Currently, nab-technology is being applied to other drugs, such as taxane and rapamycin, and explored in other cancer indications. See, e.g., U.S. Patent Pub. No. 2012/0076862.

The two primary techniques for drug loading are adsorption (conjugation or complex) and encapsulation (also referred to as embedding), each of which has specific advantages. By incubating the drug solution and albumin NPs together after nanoparticle fabrication, the drug is adsorbed to the surface of the NP. The amount of absorption relies on the affinity of the drug to the albumin. Adsorption takes advantage of many of the available binding sites present in albumin, providing albumin NPs a high binding capacity with various drugs. Elzoghby, 2012. In addition, adsorption provides insightful information on the best formulation, the drug binding capacity onto the surface of NPs and the amount of drug adsorbed. Zhang & Uludag, 26 Pharm. Res. 1561 (2009). Encapsulation can be achieved by mixing the drug solution with the albumin solution prior to the desolvation process. Drug entrapment is ideal for hydrophobic, water-insoluble drugs. Wunder et al., 2003. Additionally, literature suggests that drug encapsulation can reduce the burst effect caused by a fraction of the drug that is weakly adsorbed to the NP, allowing for a slower, more sustained release. Soppimath et al., 70 J. Contr. Release 1 (2001).

The ability for a drug carrier to release the drug at the intended site is equally as important as the ability for the drug carrier to transport the drug because only the free, unbound drug will usually deliver therapeutic benefits. The NP drug release profiles are governed by diffusion and biodegradation—if degradation occurs faster than diffusion, the primary mechanism of drug release will be degradation, and vice versa. Soppimath, 2001. With albumin, drug release is primarily dependent on the biodegradation of the albumin NP by endogenous proteases to release the therapeutic payload. Wunder et al., 2003; Das et al., 93 Colloids Surf. B. Biointerfaces 161 (2012). Others have studied the kinetics of particle degradation in the presence of different enzymes and concluded that particle stabilization influenced biodegradation and drug release. Langer et al., 347 Intl. J. Pharm. 109 (2008).

Besides small molecules, cytokines, such as growth factors, are another attractive class of therapeutic candidates for drug delivery, and NP drug delivery techniques have also been designed for effective growth factors delivery. Cytokines are endogenous polypeptides that play a critical role in transmitting signals that regulate cellular activities, such as cytokine signaling, migration, differentiation, and proliferation. By binding to specific transmembrane receptors on the target cells, cytokines are able to deliver a particular message and control cellular behavior. Lee et al., 8 J. R. Soc. Interface 153 (2011). Because cytokine, including growth factors, have limited biological half-life in circulation, in the order of several minutes, and undergo rapid degradation in vivo, it is often undesirable and inefficacious to inject growth factors directly into the body. Zhang & Uludag, 2009. In order to ensure that growth factors reach the target site and are not rapidly removed from the body, it is advantageous to use growth factors in conjunction with a drug carrier. NP-based delivery systems for growth factors have the potential to increase their therapeutic benefits by overcoming the limitations of growth factors and allowing for improved release kinetics and targeting capability.

Cytokines that can be delivered according to the present embodiments include, for example, Adrenomedullin (AM), Angiopoietin (Ang), Autocrine motility factor, Bone morphogenetic proteins (BMPs), Brain-derived neurotrophic factor (BDNF), Epidermal growth factor (EGF), Erythropoietin (EPO), Fibroblast growth factor (FGF), Glial cell line-derived neurotrophic factor (GDNF), Granulocyte colony-stimulating factor (G-CSF), Granulocyte macrophage colony-stimulating factor (GM-CSF), Growth differentiation factor-9 (GDF9), Hepatocyte growth factor (HGF), Hepatoma-derived growth factor (HDGF), Insulin-like growth factor (IGF), Migration-stimulating factor, Myostatin (GDF-8), Nerve growth factor (NGF) and other neurotrophins, Platelet-derived growth factor (PDGF), Thrombopoietin (TPO), Transforming growth factor alpha(TGF-α), Transforming growth factor betas (TGF-β), Tumor necrosis factor-alpha(TNF-α), Vascular endothelial growth factor (VEGF), placental growth factor (PlGF), Foetal Bovine Somatotrophin (FBS), IL-1—Cofactor for IL-3 and IL-6, IL-2-T-cell growth factor, IL-3, IL-4, IL-5, IL-6, IL-7, IL-10, and combinations of these.

Modulation of the immune system using the laser actuated albumin:active agent system of the present invention can be used to treat autoimmune disorders such as rheumatoid arthritis, Lupus, eczema, asthma, psoriasis, multiple sclerosis, myopathy, nephropathy, diabetes, a neurodegenerative disorder, graft-versus-host-disease (GVHD), inflammatory bowel disease (IBD), Crohn's disease, or necro-inflammatory liver disease. For example, TGF-β1, IL-10, or both, can be delivered according to the present invention to modulate the inflammatory response and suppress the extent of liver damage following injury or liver disease.

Other active agents that can be used with the laser actuated albumin nanoparticle delivery system of the present invention include anticancer agents, antiallergic agents, antithrombotic agents, immunosuppressive agents, antifungal agents, nucleic acid-based medications, anti-inflammatory agents, and regenerative agents.

In some embodiments, the active agent is an agent useful in regenereative medicine. Regenerative medicine is a strategy that seeks to repair damaged or diseased tissues to their original state or function by helping natural healing processes to work faster. Agents useful for regenerative medicine includes compounds and compositions that enhance or incerease cell growth and differentiation and formation of living tissues.

Specific examples of anticancer active agents that can be delivered by the laser-actuated albumin NPs of the present invention include fluorinated pyrimidine antimetabolites (for example, 5-fluorouracil (5-FU), tegafur, doxifluridine, and capecitabine); antibiotics (for example, mitomycin (MMC) and adriacin (DXR)); purine antimetabolites (for example, folic acid antagonists such as methotrexate and mercaptopurine); active metabolites of vitamin A (for example, antimetabolites such as hydroxy carbamide, tretinoin, and tamibarotene); molecular targeting agents (for example, Herceptin and imatinib mesylate); platinum agents (for example, Briplatin or Randa (CDDP), Paraplatin (CBDC), Elplat (Oxa), and Akupura); plant alkaloids (for example, Topotecin or Campto (CPT), taxol (PTX), Taxotere (DTX), and Etoposide); alkylating agents (for example, busulphan, cyclophosphamide, and ifomide); antiandrogenic agents (for example, bicalutamide and flutamide); estrogenic agents (for example, fosfestrol, chlormadinone acetate, and estramustine phosphate); LH-RH agents (for example, Leuplin and Zoladex); antiestrogenic agents (for example, tamoxifen citrate and toremifene citrate); aromatase inhibitors (for example, fadrozole hydrochloride, anastrozole, and exemestane); progestational agents (for example, medroxyprogesterone acetate); and BCG. Nucleic acid-based medications include, but are not limited to, antisense, ribozyme, siRNA, aptamer, and decoy nucleic acids. It is also recognized that the active agents can include crystalline or amorphous forms of the compounds noted herein, including the solvate and non-solvate forms.

For example, the active agent can be paclitaxel (metastatic breast cancer); doxorubicin or pegylated doxorubicin (metastatic ovarian cancer, late stage metastatic breast cancer, and AIDS-related Kaposi's sarcoma); amphotericin B (fungal infections); propofol (anesthetic); sevelamer hydrochloride (serum phosphorus in patients with chronic kidney disease on dialysis); fenofibrate (lipid disorders); cytarabine (lymphomatous meningitis); daunarubicin (advanced HIV-related Kaposi's sarcoma); estradiol (reduction of vasomotor functions); anti-VEGF aptamer (neovascular age-related macular degeneration); adenosine deaminase (enzyme replacement for treating severe combined immunodeficiency disease); interferon α-2a or α-2b (chronic hepatitis C virus infection); visomant (hGH) (acromegaly); GCFS or methionyl human G-CSF (febrile neutropenia); glatiramer acetate (relapsing remitting multiple sclerosis); asparginase (leukemia); siRNA or siRNA conjugates (various cancers); FUS-1 (metastatic non-small cell lung cancer); TNF (solid tumors); p-53 (solid tumors); or camptothecin (various cancers).

Another class of active agents that can be delivered using the laser-actuated albumin-conjugate NPs of the present invention are regenerative agents. These agents are relevant in pluripotent-cell (stem-cell) and regenerative biology, and include synthetic small molecules and natural products including nuclear receptor-binding agents (e.g., all-trans retinoic acid and dexamethasone); histone-modifying enzymes and DNA-modifying enzymes (e.g., trichostatin A, BIX 01294 and 5-azacytidine), protein kinases and signaling molecules (e.g., reversine, purmorphamine, 16,16-dimethyl prostaglandin E2, forskolin, QS11, BIO, cyclopamine, neuropathiazol, pluripotin, and Y-27632), and TGF-βRI antagonists (e.g., SB431542). See also U.S. patent application Ser. No. 12/294,344.

Further regarding the immune modulator TGF-β1, this is a group of multi-faceted growth factors that play pivotal roles in mediating proliferation, differentiation, inflammation, and other biological processes. Jobling et al., 166 Radiat. Res. 839 (2006); Li et al., 24 Ann. Rev. Immunol. 99 (2006). There are five known isoforms of the prototypical TGF-β namely, 1, 2 and 3 in mammals while 4 and 5 exist in amphibians. The three mammalian TGF-β isoforms have many similarities in receptor binding and biological functions but show distinct tissue distributions. The major isoform functional in the immune system is TGF-β1. Li et al., 2006.

Figure 4:
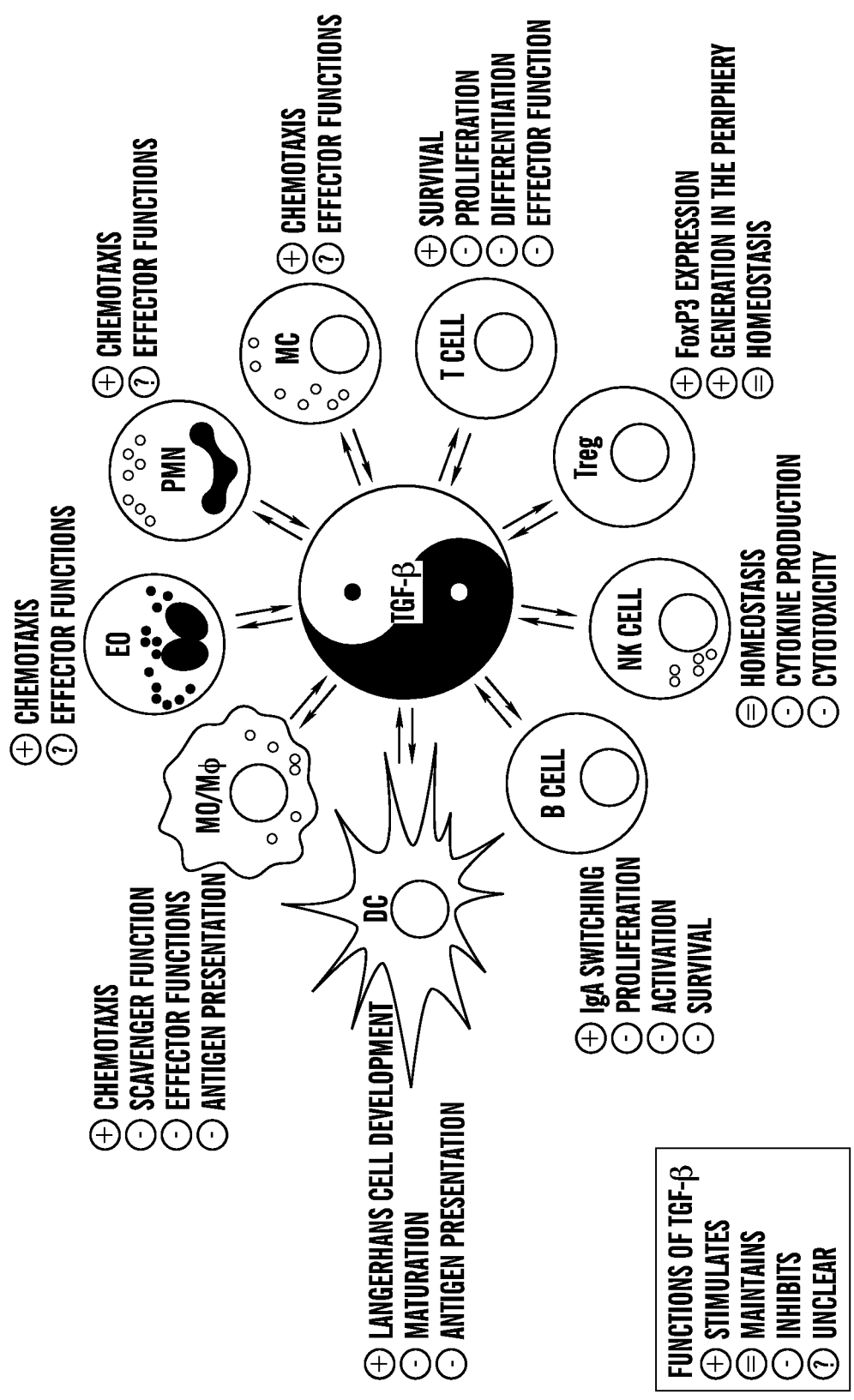
FIG. 4 presents a Summary of TGF-β immunology. Selected immunological processes regulated by TGF-β are depicted (MC, mast cell; EO, eosinophil; MO/Mφ, monocyte/macrophage). The yin-yang symbol illustrates the fact that TGF-β exerts both stimulatory and inhibitory effects on immune cells. Figure taken from Li et al., 24 Ann. Rev. Immunol. 99 (2006).

Previously, it was shown that TGF-β regulated human T cell proliferation in vitro, and this was the first observation of TGF-β regulating and modulating immune cell response. Kehrl et al., 163 J. Exp. Med. 1037 (1986). The primary role of TGF-β in the immune system is to induce tolerance, as well as to contain and resolve inflammation. Li et al., 2006. Unlike other cytokines, TGF-β is produced in both immune and non-immune cells and virtually all cell types can respond to it. Sanjabi et al., 9 Curr. Op. Pharmacol. 447 (2009). The TGF-β superfamily regulates immune cell function, and is known to play a regulatory role in T Lymphocytes, Tregs, B Lymphocytes, Natural Killer (NK) Cells, Dendritic Cells (DCs), Macrophages, Mast Cells (MCs), and Granylocytes. Li et al., 2006. TGF-β1 has been shown to have both pro-inflammatory and anti-inflammatory effects. Early in the immune response, TGF-β1 promotes inflammatory by increasing the expression of cell adhesion molecules, creating a chemotactic gradient, and inducing pro-inflammatory cytokines. On the other hand, in later phases, TGF-β1 downregulates inflammation and promotes wound healing. Aoki et al., 4 Autoimmun. Rev. 450 (2005). FIG. 4 provides a summary of the role of TGF-β as an immunomodulator in various leukocyte lineages.

DCs are antigen-presenting cells (APCs) that initiate and modulate immune response. Banchereau & Steinman, 392 Nature 245 (1998). TGF-β1 regulates the development of Langerhans cells (LCs) and the maturation and function of differentiated DCs. DCs in the presence of TGF-β1 express intracellular MHC class II, low levels of CD1d, and costimulatory molecules. Studies have established that TGF-β1 stimulates the development of LCs from monocytes. TGF-β1 also inhibits maturation of DCs differentiated from bone marrow cells with GM-CSF resulting in DCs with an immature phenotype. Li et al., 2006. In addition, TGF-β inhibits antigen presentation in vitro. Stimulation of DCs with pro-inflammatory cytokines (e.g., IL-1b and TNFα bacterial components (e.g., lipopolysaccharide (LPS), or costimulatory receptors upregulates MHC class II, costimultory molecules, and certain cytokines and promotes their maturation. In LPS, IL-1b, TNF-α-stimulated LCs, TGF-β1 was found to down-regulates IL-12, effectively inhibiting maturation of the LCs and potentially avoiding harmful immune responses. Geissmann et al., 162 J. Immunol. 4567 (1999). LPS-stimulated DCs induce cytokine production via the activation of NF-κB, ERK1/2, and p38, all of which are located upstream of the TLR4 signal pathway. TGF-β1 has been shown to suppress LPS-stimulated NF-κB, ERK1/2, and p38 levels in DCs. Mou et al., 43 Transplant Proc. 2049 (2011).

Macrophages are phagocytes that play a key role in fibrosis and regulate fibrogenesis by secreting chemokines, including TGF-β1, that recruit fibroblasts and other inflammatory cells. Wynn & Barron, 30 Sem. Liver Dis. 245 (2010). TGF-β was first recognized as an inhibitor of macrophage activation in 1988. Tsunawaki et al., 334 Nature 260 (1988). TGF-β has proinflammatory functions by recruiting monocytes to sites of inflammation by acting as a chemoattractant, inducing and enabling adhesion molecules to attach to the extracellular matrix, and inducing matrix metalloproteinases (MMPs). Once monocytes differentiate into macrophages, TGF-β functions primarily as an inhibitory molecule. Li et al., 2006. Macrophages play three major roles in inflammation: antigen presentation, phagocytosis, and immunomodulation through growth factor and cytokine production. Fujiwara & Kobayashi, 4 Curr. Drug Targ. Inflamm. Allergy 281 (2005). When inflammation is induced in macrophages with LPS, TGF-β has been found to inhibit induced inflammatory mediators, such as TNF-α and IL-1b by down-regulating activation protein 1 and CD14 receptor expression. Imai et al., 68 Infect. Immun. 2418 (2000).

In vivo studies have revealed a critical function for TGF-β in regulating leukocyte functions in autoimmune diseases, including systemic lupus erythematosus, rheumatoid arthritis (RA), insulin-dependent (type 1) diabetes mellitus, and multiple sclerosis. TGF-β's also have been found to regulate tumor immunity, athrosclerosis, inflammatory bowel disease, and several infectious diseases. As can be seen, TGF-β plays a key role in modulating immune response, however the application of TGF-β for therapeutic purposes in immune disorders has been largely unexplored. Li et al., 2006.

The term LASER (Light Amplification by Stimulated Emission of Radiation) was first coined by Gordon R Gould in 1959. Gould, The LASER, Light Amplification by Stimulated Emission of Radiation, in Ann Arbor Conf. Optical Pumping (Univ. Michigan, Ann Arbor, 1959). Since then, lasers have found applications in all fields ranging from manufacturing to biology. Clinical and research studies have used low power laser (LPL) therapy for wound healing and tissue repair. More recently, light-based applications have been explored in actuating drug release.

As mentioned herein, drug release is an important component of designing a drug carrier. In drug delivery, there is a need for a "release on demand" controlled delivery system. This controlled release system is commonly triggered in local environments by using changes in pH or temperature, or enzymatic cleavage to release the encapsulated or conjugated payload. Lee et al., 2011. Heat and light have been explored in other delivery systems as alternative methods to control local payload release. De Jong & Borm, 2008. It has been suggested that low power laser (LPL) irradiation generates many reactive oxygen species (ROS), transferring light energy to a chemical energy, which can have a biological effect. Ricci-Junior & Marchetti, 23 J. Microencapsul. 523 (2006).

Researchers have explored light-actuated polymer conformation changes by remote light activation. Lendlein et al., 434 Nature 879 (2005); Kobatake et al., 446 Nature 778 (2007). Moreover, near-infrared wavelengths that can penetrate the tissue have been used for in vivo to induce nanoparticle conformational change. Hribar et al., Conf. Proc IEEE Engin. Med. Biol. Socy. 2409 (2009). More specifically, Ricci-Junior and Marchetti developed a photosensitive ZnPc encapsulated PLGA NP cancer treatment system, which upon laser irradation (600 nm-700 nm) for 120 seconds at 16 J/cm2 released the payload and led to 90% cell death. Ricci-Junior & Marchetti, 2006. Others have developed a photodegradable PEG-based hydrogel, in which light can be harnessed to modulate the physical conformation of the polymer and allow for controlled drug release. Kloxin et al., 324 Science 59 (2009). In order to overcome unfavorable properties of free drugs, researchers have developed photoresponsive prodrugs. These prodrugs are 'caged' by a covalently attached photocleavable group that can be removed upon UV laser irradiation and restore the drug's therapeutic bioactivity. Noguchi et al., 16 Bioorg. Med. Chem. 5380 (2008).

Albumin NP drug delivery systems rely primarily on natural degradation through protease activity in order to release the payload. This limits the ability to control the release of the therapeutic agent. As mentioned herein, laser modulates the physical conformation of BSA. The present embodiments provide for laser irradiation as an actuator to control the bioavailability of a therapeutic agent, in this case TGF-β1 (FIG. 2). This novel system allows for a "release on demand" type of delivery system and can overcome the drug release limitations of current albumin NP systems and allow for a more controlled and targeted delivery mechanism. The present inventions provides for the effects of laser actuation on the bioavailability of TGF-β1 conjugated to BSA NPs.

Figure 7:
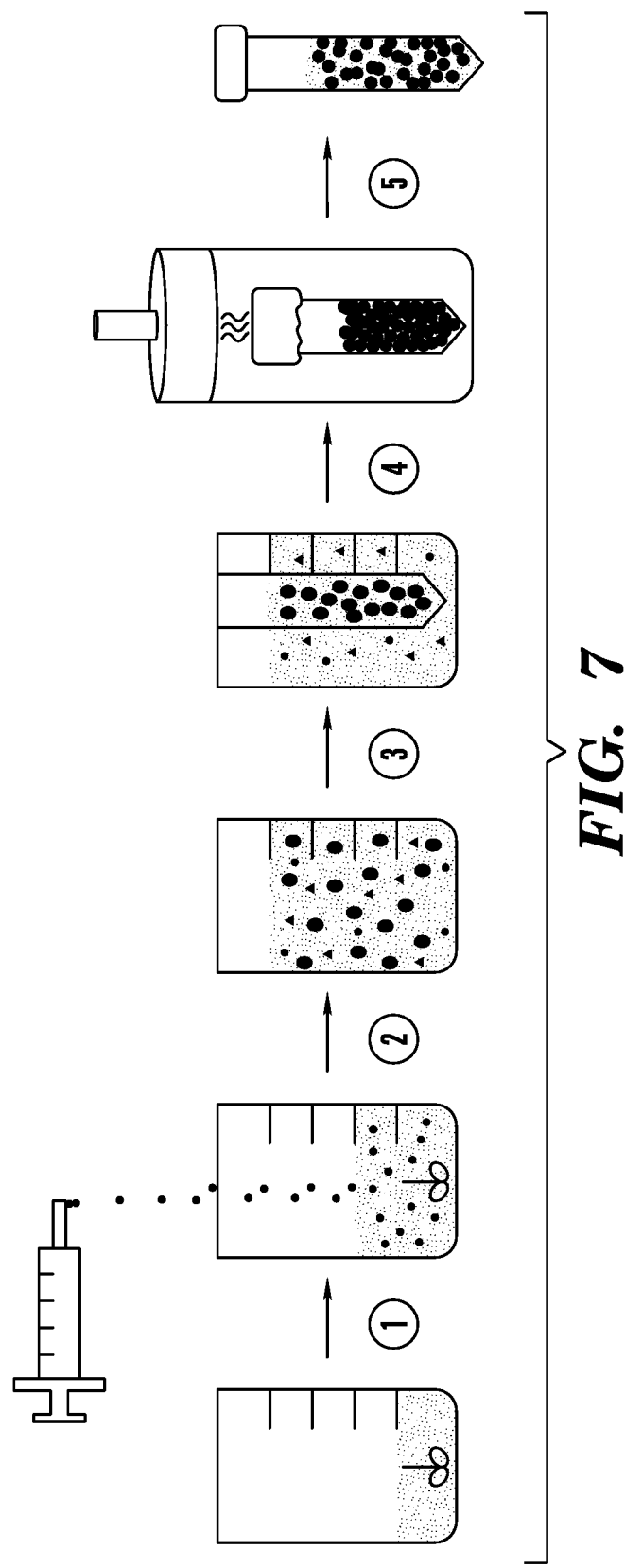
FIG. 7 is a schematic of BSA NP fabrication. The diagram represents the steps in the BSA NP fabrication process: (1) Coacervation, (2) Stabilization, (3) Dialysis, (4) Lyophilization, (5) Reconstitution.

There are five main steps in the BSA NP fabrication process as described herein: coacervation, stabilization, dialysis, lyophilization, and reconstitution (FIG. 7). The coacervation step controls nanoparticle formation because as ethanol is added dropwise to the albumin solution (initial pH 7.1), it forms nanoparticles due to its diminished water solubility. Stabilization ensures that the nanoparticles will remain stable and will not redissolve or aggregate in solution. The dialysis step removes excess stabilizer and ethanol. Lyophilization freeze-dries the BSA NPs into a dry powder for long-term storage until reconstituted for experimental use.

Figure 8:
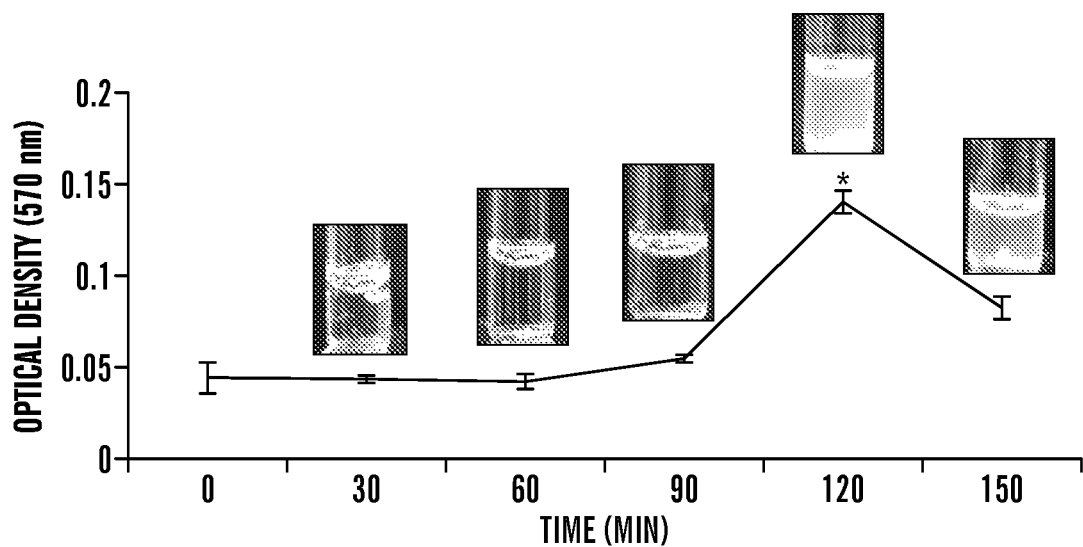
FIG. 8 shows the fabrication of BSA NPs. Measurement of the optical density at 570 nm of BSA NP solution during ethanol coacervation over time (* indicates p<0.05). Inset images show the optical density of NP solution at 30 minute time intervals.
Figure 9:
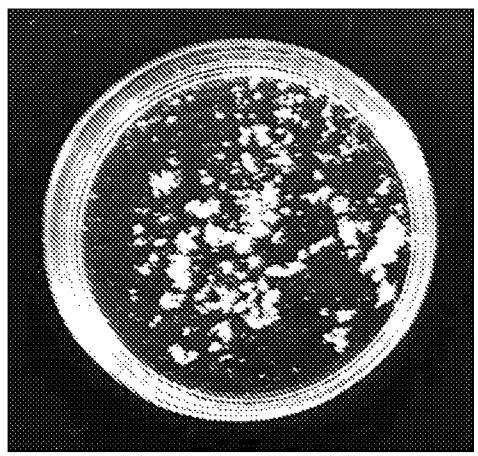
FIG. 9 shows the aggregation of BSA NPs. Image of the large aggregates observed following prolonged ethanol coacervation (2.5 hours).

Regarding coacervation, to optimize the nanoparticle fabrication process, samples were removed during the coacervation step every 30 minutes for 2.5 hours. The optical density at 570 nm was measured at each time point. The highest optical density occurred at the 2-hour time mark (FIG. 8). The images of the solution at each time point show the transition from transparent to cloudy. After 2 hours, large aggregates begin to form and fall out of solution (FIG. 9), corresponding with a decrease in the optical density.

Figure 10:
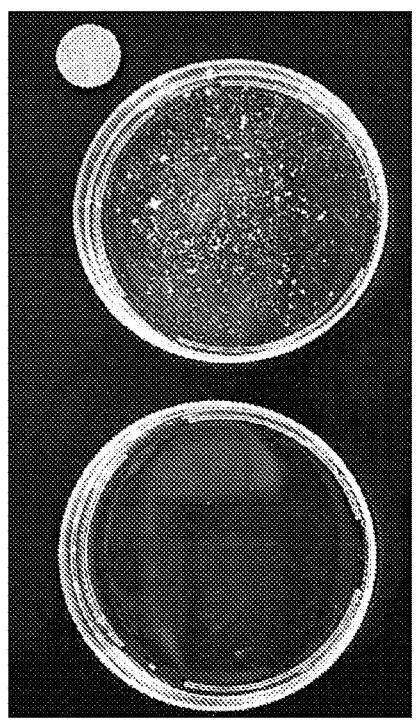
FIG. 10 shows aggregates formed during dialysis of BSA NPs. Aggregates formed during the dialysis of BSA NPs against 1 M NaCl (left) and PBS (right) collected after filtration through a 40 μM cell strainer.
Figure 11A:
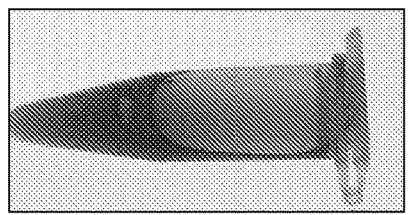
FIGS. 11A-11D show the protein aggregates formed from dialysis of BSA NPs. A BCA was used to determine the presence of protein in sample aggregates. The negative control (FIG. 11A) is PBS and the positive control (FIG. 11D) is a 10 mg/mL solution of BSA. Large aggregates collected from BSA NPs dialyzed against 1 M NaCl (FIG. 11B) and against PBS (FIG. 11C).
Figure 11B:
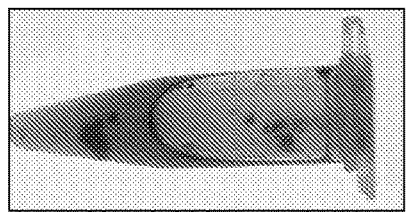
Figure 11C:
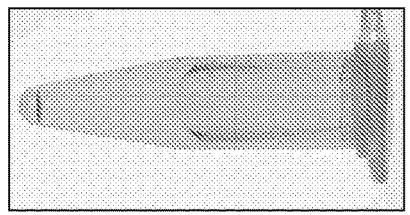
Figure 11D:
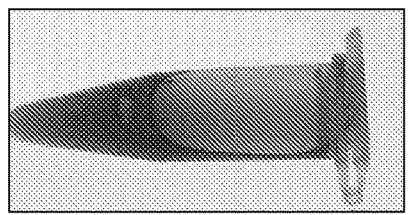

Following a published protocol (Wang et al., 2008) the BSA NPs were dialyzed against 1 mM NaCl solution for 3 days to remove excess ethanol and PLL stabilizer. Dialysis against 1 mM NaCl resulted in precipitation of the albumin, however. To further investigate the role of salt in the stability of NPs during dialysis, BSA NPs were also dialyzed against PBS (137 mM NaCl) and 1 M NaCl. After a 3-day dialysis against PBS or 1 M NaCl, both BSA NP solutions were both filtered through a 40 μm cell strainer to collect any large aggregates. The collected aggregates were resuspended in PBS. There was a significant amount of aggregates collected from the BSA NPs dialyzed against PBS (FIG. 10).

Similar aggregation was seen in BSA NPs dialyzed against 1 mM NaCl. There were no visibly observable aggregates collected from the NPs dialyzed against 1 M NaCl. To investigate whether the aggregates were salt or proteins, a modified Bradford's assay, BCA, was performed. The aggregates collected from the PBS dialyzed BSA NPs turned purple while there was a slight color change in the aggregates collected from the NPs dialyzed against 1 M NaCl (FIG. 11). These results indicate that albumin aggregates are formed following BSA NPs dialysis against PBS, but there is insignificant aggregate formation in the BSA NPs dialyzed against 1 M NaCl.

For nanoparticle characterization after dialyses of BSA NPs, DLS was used to investigate the quality of BSA NPs dialyzed against 1 mM NaCl, PBS, and 1 M NaCl. Due to the presence of salt in the NPs, lyophilized BSA NPs were reconstituted in mgH$_2$O to maintain a "salt-like" background. The DLS measurement indicated good quality for the BSA NPs dialyzed against 1 M NaCl, but poor quality and high polydispersity for the BSA NPs dialyzed against 1 mM NaCl and PBS as shown in Table 1.

TABLE 1

Summary of BSA NP in dialysates.

| Dialysis Buffer | Quality | Polydispersity Index (PdI) | Hydrodynamic Diameter |
|---|---|---|---|
| 1 mM NaCl | Poor | 0.464 | N/A |
| PBS | Poor | 1.0 | N/A |
| 1M NaCl | Good | 0.171 | 232.8 nm |

Figure 12A:
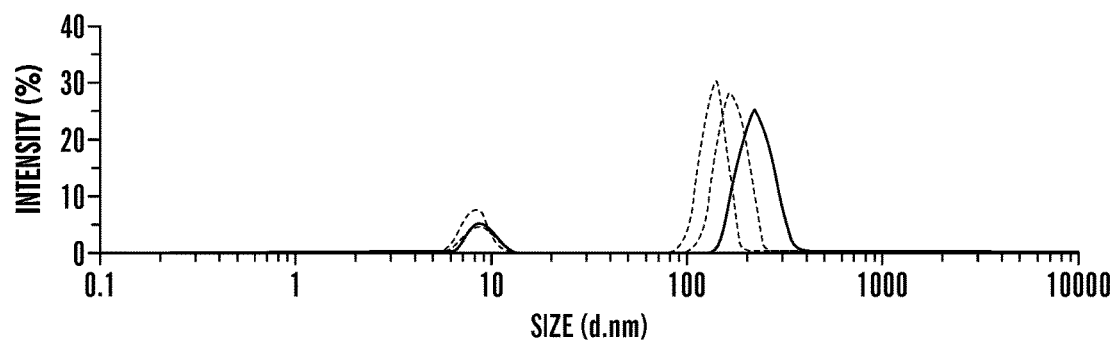
FIGS. 12A-12C show the size distribution of BSA NPs. Measurement of the size distribution of BSA NPs after lyophilization and reconstitution using DLS (n=3). BSA NPs dialyzed against 1 mM NaCl (FIG. 12A), against PBS (FIG. 12B), and against 1 M NaCl ((FIG. 12C).
Figure 12B:
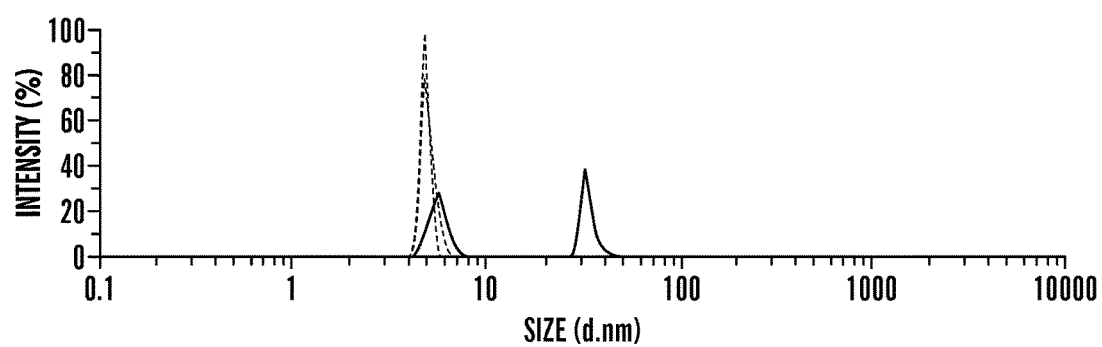
Figure 12C:
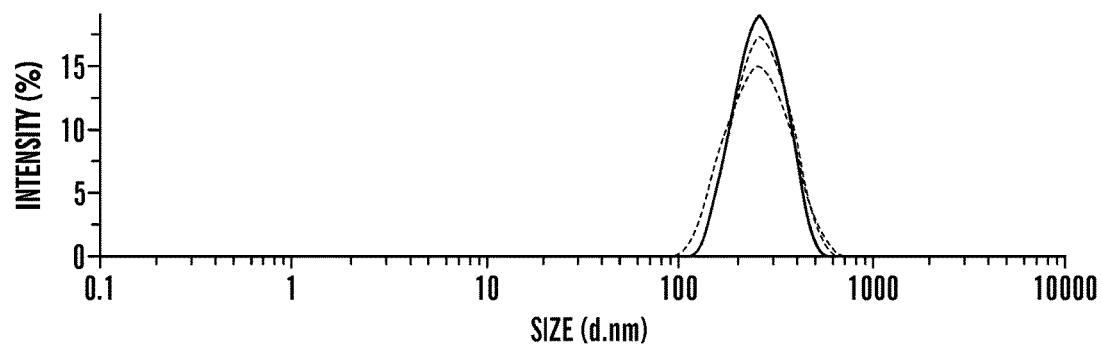

BSA NPs dialyzed against 1 mM NaCl and PBS showed multiple peaks and BSA NPs dialyzed against 1 M NaCl had a single, clean peak at 232.8 nm (FIG. 12). The DLS results indicate that dialysis against 1 M NaCl solution produced the best quality BSA NPs. The remaining experiments used BSA NPs dialyzed against 1 M NaCl, and will be referred to as BSA NPs, unless otherwise noted.

The solvent effect on DLS measurements were studied because BSA NPs are protein-based, and thus the solvent influences protein-packing and the measured hydrodynamic diameter. To examine the effect of the analysis solvent used in DLS on the measured size, samples of BSA NPs were read in PBS and diH$_2$0. The hydrodynamic diameter of BSA NPs in PBS and diH$_2$0 were significantly different, and BSA NPs read in PBS had a consistently smaller hydrodynamic diameter measurement (Table 2). The results of samples read in PBS would be most physiologically relevant; hence, further DLS experiments were carried out in PBS.

TABLE 2

Hydrodynamic diameter of BSA NPs

| Analysis Colvent | Hydrodynamic Diameter (nm) |
|---|---|
| PBS | 241.9 ± 0.42 |
| diH$_2$O | 387.1 ± 36.77 |

Figure 13A:
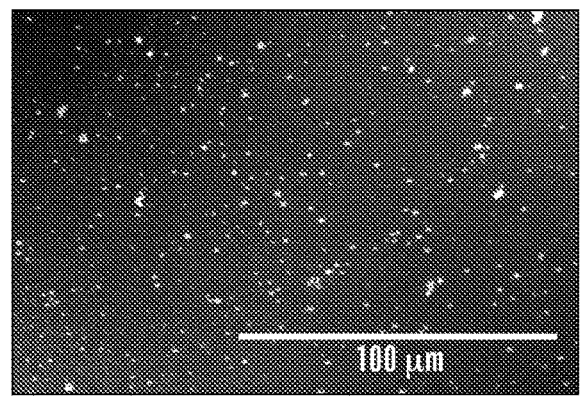
FIGS. 13A and 13B show the data from surface-enhanced ellipsometric contrast. Lyophilized BSA NPs were imaged using SEEC (FIG. 13A) and the average size was determined (FIG. 13B, n=6).
Figure 13B:
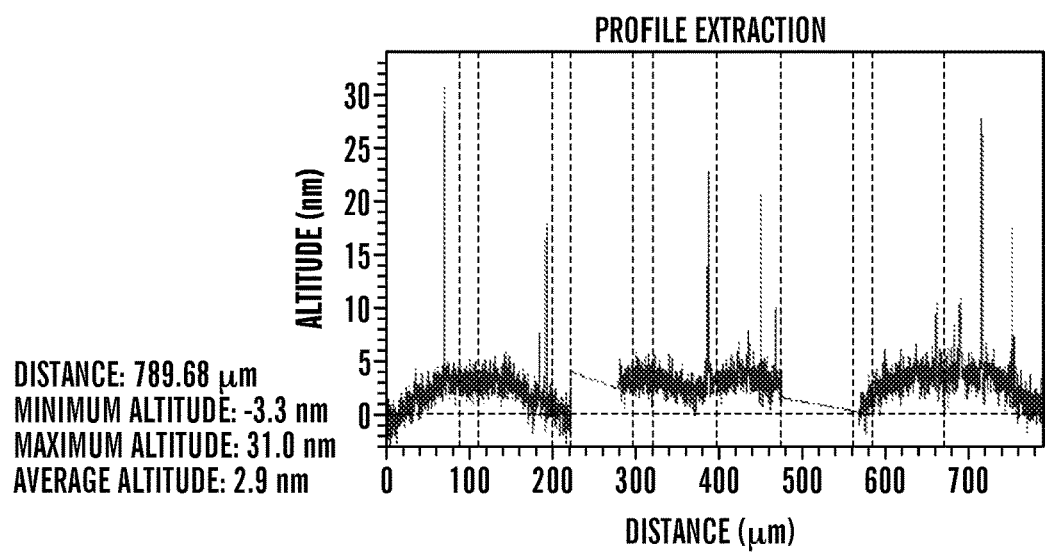

Additionally, because BSA NPs are protein-based it is difficult to use traditional imaging tools (such as transmission electron microscopy) to visualize the NPs: the NPs are destroyed during sample preparation. Therefore, a novel imaging technique was used, Surface Ellipsometeric Enhanced Contrast, that increases contrast between the background by using a specially designed anti-reflective microscope slide surfaces was used to image BSA NPs. See Ausserre & Valignat, 15 Opt. Express 8329 (2007). SEEC and SARFUS Mapping Lite analysis determined that the average NP was approximately 22.8 nm (FIG. 13).

Figure 14:
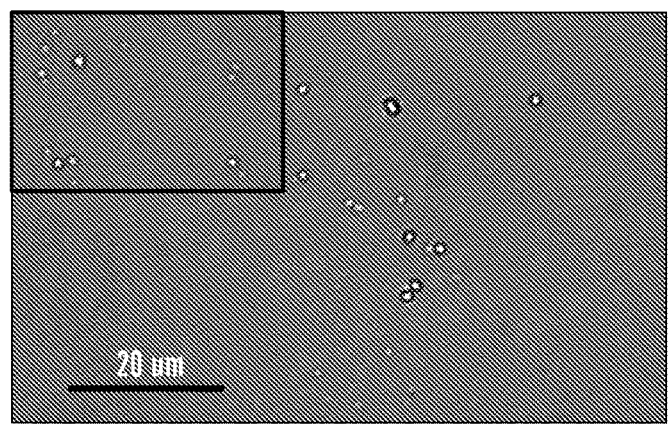
FIG. 14 shows water immersion of BSA NPs. Imaging of BSA NPs used water immersion. Upper left hand box shows HA beads with a known size of approximately 200 nm.

Because the samples used for SEEC visualization needed to be dry during imaging, these measurements can not represent the true radius of BSA NPs. Therefore, alternative imaging techniques were also explored. In order to confirm the DLS measurements, phase contrast microscopy with water immersion lens was used to image the BSA NPs. HA beads with a known size of approximately 200 nm were used as a positive control (FIG. 14, left inset). The analysis indicates comparable size between the BSA nanoparticles and the HA beads, suggesting that the fabricated NPs have a hydrodynamic radius of approximately 200 nm (FIG. 14).

Compositional characterization of NPs was also explored. SEM-EDS was used for elemental analysis of BSA NPs dialyzed against 1 M NaCl and diH2O. This analysis was done in order to confirm the presence of salt (sodium and chloride) in the BSA NPs. SEM images NP samples were taken and the composition was determined by weight percent (FIG. 15).

Regarding the protein nature of BSA NPs, to confirm protein composition of the BSA NPs, BCA was performed and observed for color change. BSA NPs demonstrate a robust color change, confirming the albumin-based nature of these NPs (FIG. 16).

Figure 18:
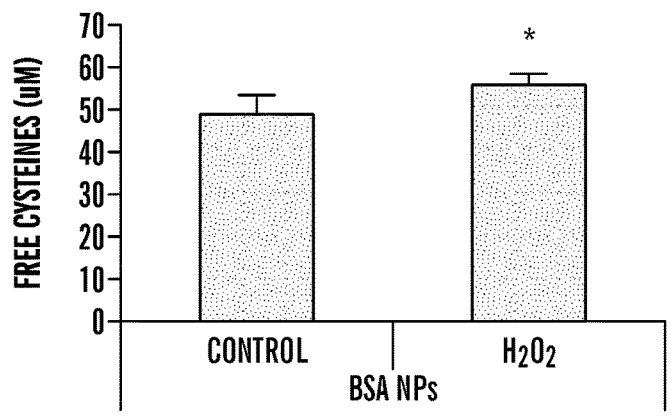
FIG. 18 is a bar graph showing that ROS increases free cysteine concentration in BSA NPs. Treatment of BSA NPs with $H_2O_2$ (10 uM) followed by assessment of free cysteines with IAEDANs dye and quantitation by microplate reader (n=3, * indicates p<0.05.

Investigations also revealed that ROS modulates conformation changes in BSA NPs. Previous work had shown that ROS modulates the conformation of BSA, as seen by the significant increase in the free cysteines in BSA upon the addition of H2O2 (FIG. 17) and following CD analysis. To examine the ability of ROS to modulate BSA NPs conformation, NP solutions were treated with H2O2 (10 µM) and assessed for free cysteine concentration using the IAEDANs dye. There was a significant increase in free cysteine concentration, indicating that ROS can modulate conformational change in BSA NPs (FIG. 18).

Figure 19A:
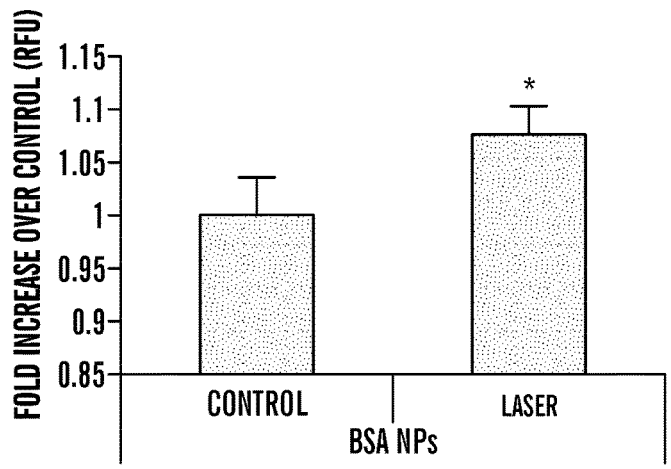
FIGS. 19A and 19B are bar graphs showing laser irradiation generates ROS and modulates free cysteine concentration. BSA NPs irradiated with laser (3 J/cm2) were assessed for H2O2 (FIG. 19A) with Amplex dye and free cysteines (FIG. 19B) with IAEDANs dye and quantitation by microplate reader (n=3, * indicates p<0.05).
Figure 19B:
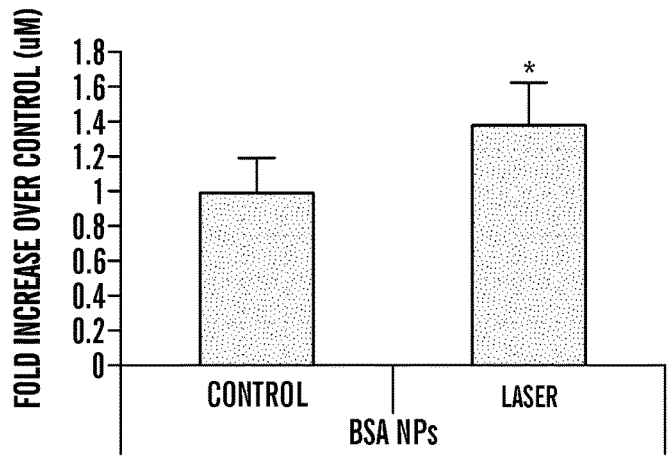
Figure 20A:
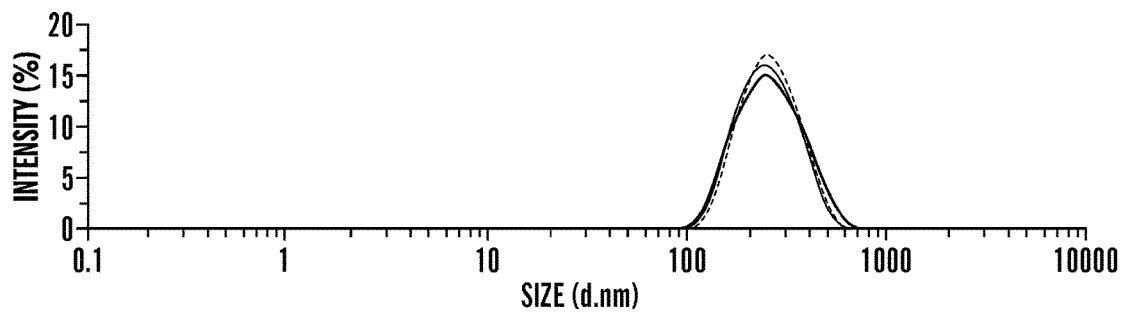
FIGS. 20A-20D show analysos of BSA NP size following activation. Measurement of the size distribution of BSA NPs after activation by laser (FIG. 20B, 3 J/cm$^2$), H2O2 (10 µM) (FIG. 20C, 10 µM), and DTT (FIG. 20D, 500 mM) (all n=3).
Figure 20B:
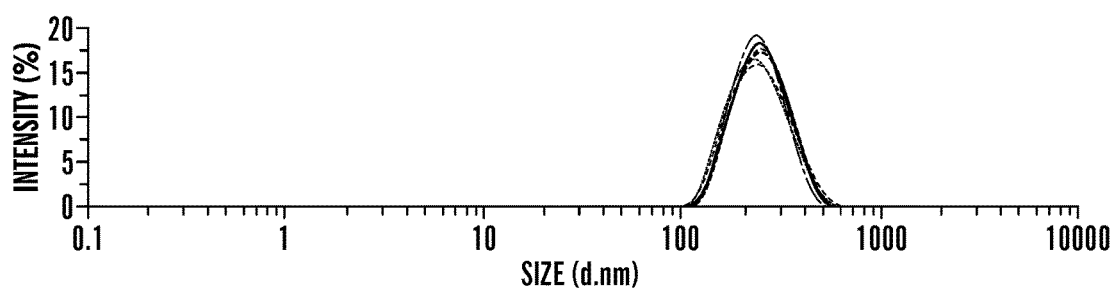
Figure 20C:
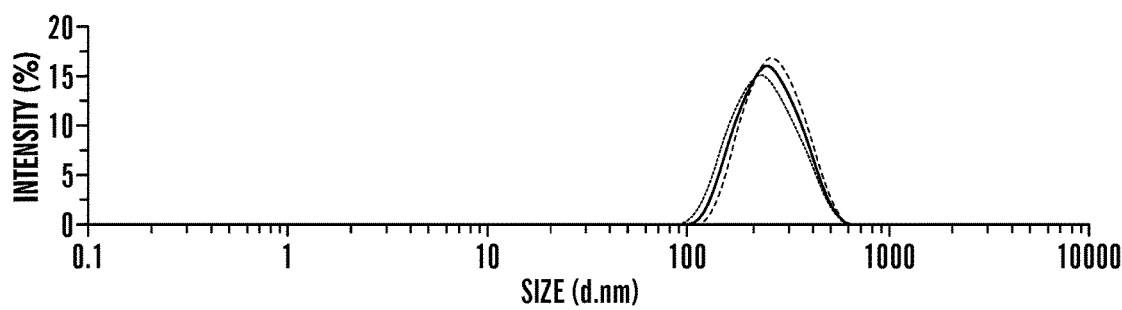
Figure 20D:
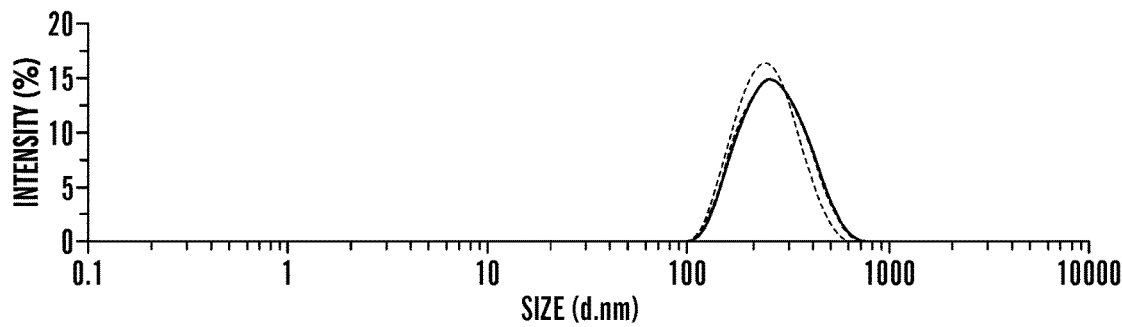

Laser actuation of BSA NP conformation was explored. Biochemical assessment of BSA NP conformational changes reflected the fact that ROS can modulate conformation of BSA NPs, as demonstrated with the increase in free cysteines following exposure to H2O2. BSA-NPs exposed to laser irradiation were assessed for H2O2 generation with the Amplex UltraRed assay and free cysteine concentration with the IAEDANs dyes. A significant increase in the hydrogen peroxide and free cysteine concentration was observed following laser irradiation (FIG. 19).

To further explore the effect of laser modulation on the integrity of the BSA NP, the hydrodynamic diameter was measured using DLS before and after laser actuation (3 J/cm2, for 5 minutes). BSA NPs showed no significant change in diameter following laser actuation and maintained good NP quality, indicating there is no significant change in global NP conformation. (FIG. 20) To further explore the mechanism for laser-mediated BSA NP conformational change, BSA NPs were exposed to H2O2 (10 µM) or DTT (500 mM) and assessed for changes in hydrodynamic diameter. Both of these experimental conditions showed no significant change in hydrodynamic diameter, consistent with the observations following laser actuation indicating that the global conformational and hence NP integrity is preserved (FIG. 20).

Figure 21:
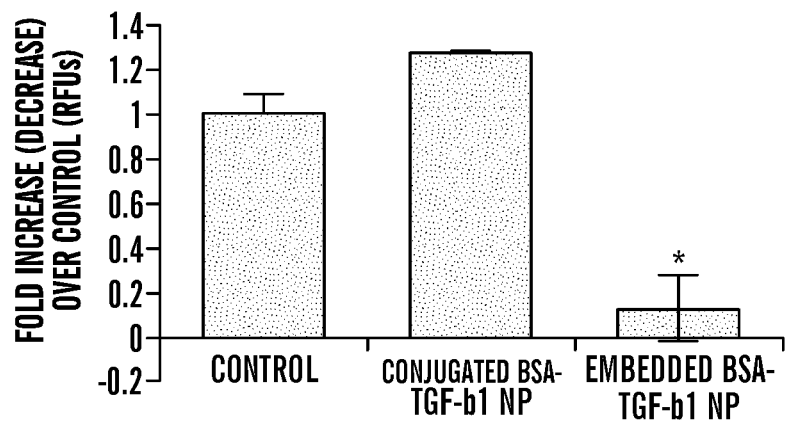
FIG. 21 reflects toxicity of BSA NPs. The toxicity of embedded and conjugated BSA NPs in RAW293 cells using Alamar Blue, quantitation by microplate reader (n=3, indicates p<0.05).
Figure 22:
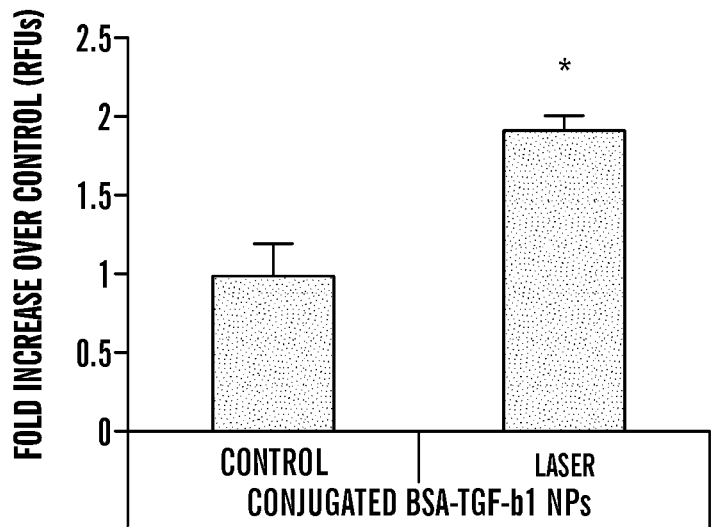
FIG. 22 illustrates that laser irradiation modulates conformation in conjugated BSA-TGF-β1 NPs. BSA:TGF-β1 NPs irradiated with laser (3 J/cm2) were assessed for free cysteines with IAEDANs dye and quantitation by microplate reader (n=3, * indicates p<0.05).

In vitro toxicity of embedded and conjugated BSA NPs is an important pre-clinical consideration. At equal dry weight reconstitution concentrations, BSA NPs embedded with TGF-β1 showed significantly higher toxicity compared to BSA NPs conjugated with TGF-β1 (FIG. 21). As a result, BSA NPs conjugated with TGF-β1 were used for future characterization and in vitro experiments.

The actuation of TGF-β1 either embedded or conjugated with albumin nanoparticles was analyzed. Because laser actuation was capable of modulating albumin nanoparticle conformation without compromising their integrity, the ability to deliver a payload was explored. As a model payload, TGF-β1 was explored as a candidate to incorporate with the BSA NP system because of its well-studied immune-modulatory effects. Two approaches were used for this, either conjugating or embedding BSA NPs with TGF-β1 as described in the Examples.

An IAEDANs assay was performed to demonstrate that the laser modulates the conformation of BSA NPs conjugated to TGF-β1. BSA:TGF-β1 NPs were subjected to laser actuation and assessed for free cysteine levels. BSA:TGF-β1 NPs following laser actuation showed a significant increase in free cysteine availability, which is consistent with previous observations using BSA NPs alone.

Figure 23:
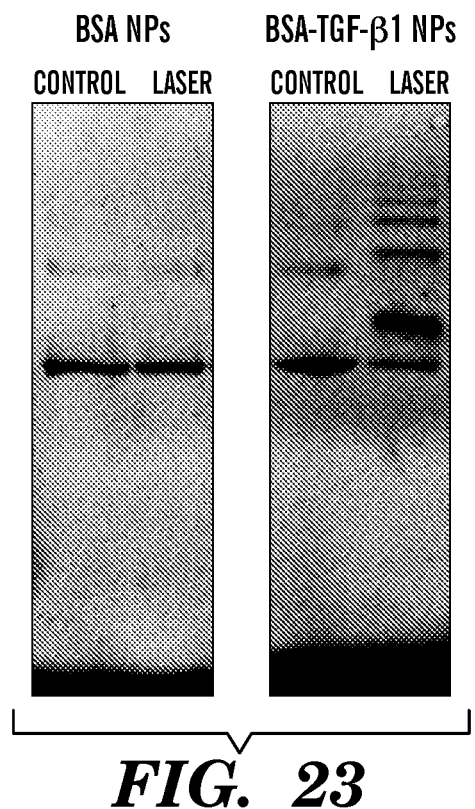
FIG. 23 shows IAEDANs (UV) imaging of NPs after actuation. Fluorescently tagged BSA NPs (left) and BSA:TGF-β1 NPs with and without laser actuation (3 J/cm2) were run in a native gel and assessed using UV imaging.

Further, NPs probed with IAEDANs dye were subjected to native gel electrophoresis and imaged using UV light. Many new bands with decreased mobility were noted following laser actuation, indicating that the changed conformation of BSA NPs with free cysteines were tagged with the IAEDANs dye (FIG. 23). It should be noted that laser actuation did not demonstrate any lower bands, indicating NPs maintained their integrity.

Figure 24:
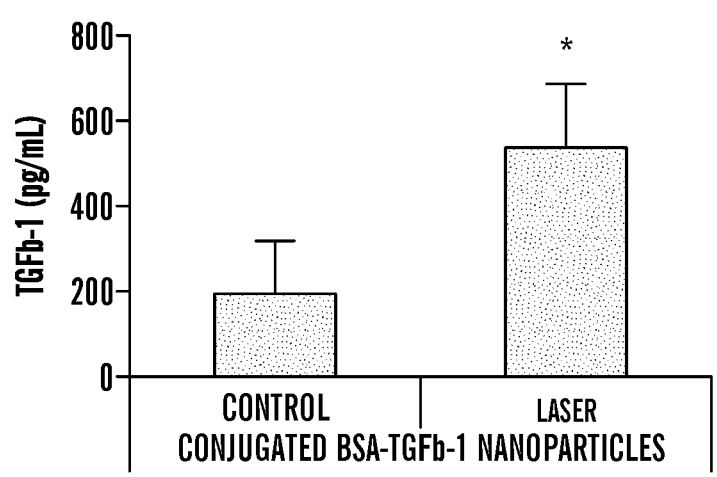
FIG. 24 demonstrates available TGFb-1 in BSA:TGF-β1 NPs after laser actuation. Laser actuation (3 J/cm2) of BSA:TGF-b1 NPs by assessment of bioavailable TGF-β1 using a TGF-β1 ELISA and quantitation by microplate reader (n=4, * indicates p<0.05). Chemical activation was used as a positive control.

Importantly, laser irradiation actuated BSA:TGF-β1 NPs, and increased TGF-β1 bioavailability. ELISA assays were used to investigate the effect of laser irradiation on BSA NP TGF-β1 availability. Nanoparticles were subjected to two conditions: no laser irradiation (control) and laser irradiation at 3 J/cm2 for 5 minutes. A TGF-β1 ELISA was used to measure increased TGF-β1. BSA NPs subjected to laser actuation showed a significant increase in the concentration of active available TGF-β1 (FIG. 24).

Figure 25:
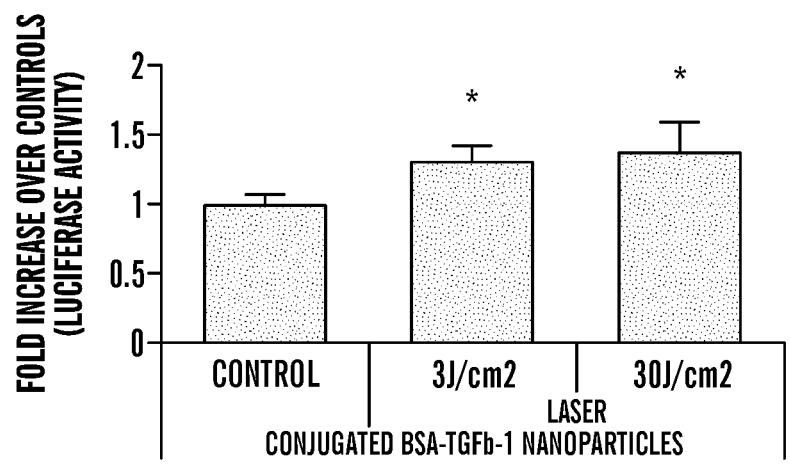
FIG. 25 demonstrates the bioavailability of TGF-β1 in BSA:TGF-β1 nanoparticles upon laser actuation. Measurement of bioavailable TGF-β1 after laser actuation (3 J/cm2) of BSA:TGF-β1 NPs using a Luciferase assay on the condition media of a PAI Reporter Cell line; quantitation by microplate reader (n=3, * indicates p<0.05 compared to control).
Figure 26:
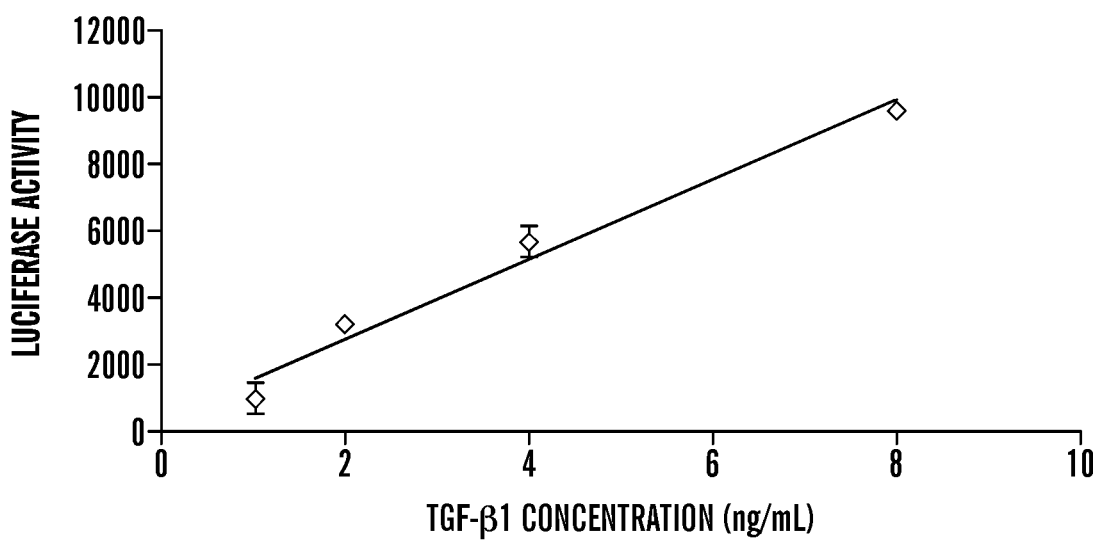
FIG. 26 shows luciferase activity of TGF-β1 reporter cell line treated with various concentrations of TGF-β1. Measurement of luciferase assay on the condition media of a PAI Reporter Cell line treated with different concentrations of recombinant TGF-β1 (n=2); quantitation by microplate reader.

Because laser-actuated BSA:TGF-β1 NPs demonstrated a conformation change and increased TGF-β1, the increased bioavailable TGF-β1 was assessed for biological activity using an epithelial TGF-β1 reporter cell line (Mv1Lu) stably transfected with p3TP-luciferase (Plasminogen Activator Inhibitor gene promoter) [48]. See Abe et al., 216 Anal. Biochem. 276 (1994). Mv1Lu cells treated with laser actuated BSA:TGF-β1 NPs showed significantly higher luciferase activity compared to non-laser actuated controls (FIG. 25). As positive controls, cells were treated with several concentrations of recombinant TGF-β1 and showed a linear increase in luciferase activity (FIG. 26).

Figure 27:
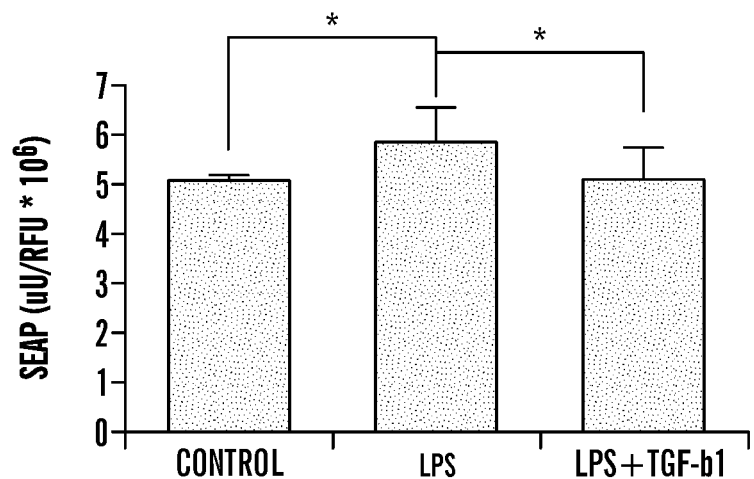
FIG. 27 illustrates the efficacy of in vitro immune modulation model. RAW293 reporter cells were subjected to LPS and TGF-β1 for 24 hours. SEAP was measured in condition media and normalized to Alamar Blue (n=3, * indicates p<0.05).
Figure 28:
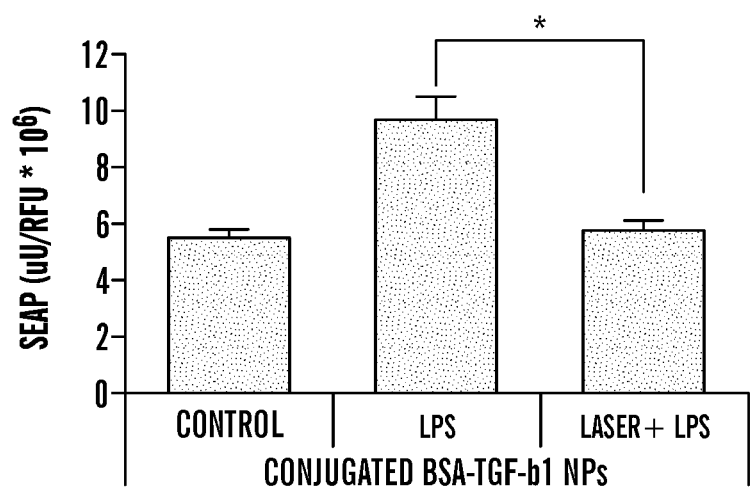
FIG. 28 reflects laser actuated BSA:TGF-β1 NPs in an in vitro immune modulation model. RAW293 reporter cells were subjected to LPS treatment in the presence of BSA:TGF-β1 NPs with or without laser actuation. SEAP in conditioned media was assessed and normalized to Alamar Blue (n=3, * indicates p<0.05).

To explore the ability of BSA:TGF-β1 NPs as immunemodulators, several in vitro assays were performed to assess the efficacy of TGF-β1 delivery via laser actuation of BSA:TGF-β1 NPs. For example, for a NF-κB reporter assay, a murine macrophage cell line, RAW293, stably transfected with NF-κB/AP-1-promoter tagged to secreted alkaline phosphatase (SEAP), was treated with LPS to simulate inflammation. LPS treatment increased amounts of secreted alkaline phosphatase while TGF-β1 co-treatment significantly reduced these levels (FIG. 27). Laser actuated BSA: TGF-β1 NPs were able to significantly reduce levels of LPS stimulated SEAP levels compared to control NPs (FIG. 28). This assay demonstrated the ability of laser actuated BSA: TGF-β1 NPs to reduce an LPS-induced immune response.

Figure 29A:
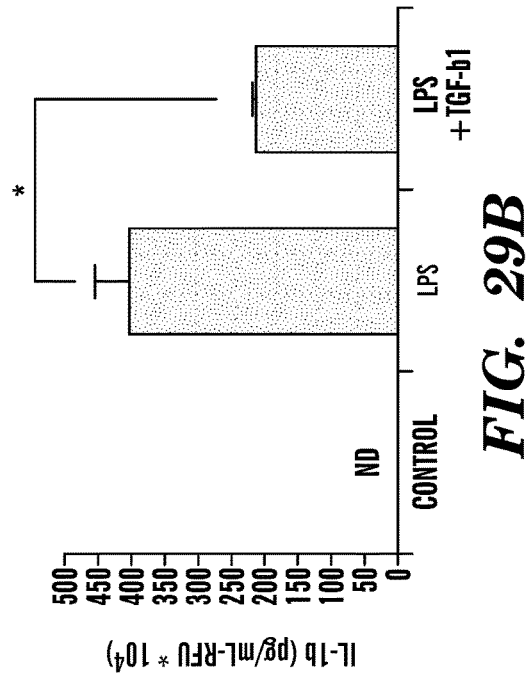
FIG. 29 shows the immune-modulatory effect of TGF-β1 on pro-inflammatory cytokines. Measurement of pro-inflammatory cytokine, TNF-α (FIG. 29A) and IL-1b (FIG. 29B), in primary BMDC after LPS induction and LPS+TGF-β1 following 24 hour incubation. Cytokine concentrations assessed with a TNF-a and IL-1b ELISA, respectively, and normalized to cell metabolic activity with Alamar Blue; quantitation by microplate reader (n=4, * indicates p<0.05). ND indicates levels below detectable range.
Figure 29B:
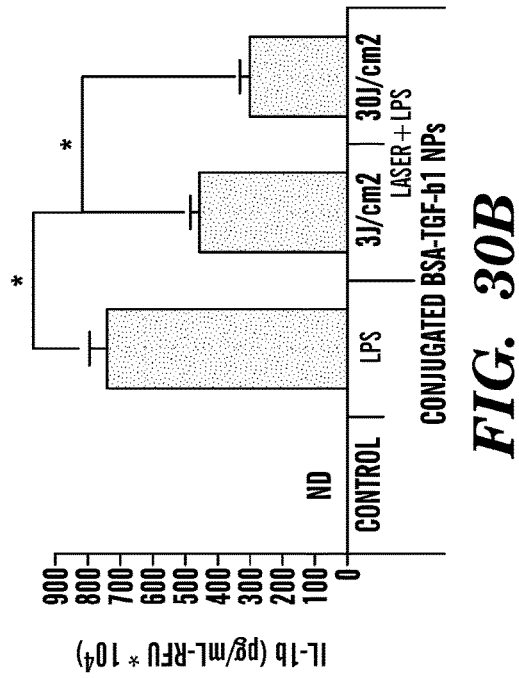

Another assay used TNF-α and IL-1b in primary bone marrow dendritic cells. More specifically, to further examine the role of BSA:TGF-β1 NPs as an immune modulator, BMDCs at day 12 were used. LPS significantly increased the concentration of pro-inflammatory cytokines TNF-α and IL-1b while TGF-β1 co-treatment reduced these levels significantly (FIGS. 29A and 29B, respectively).

Figure 30A:
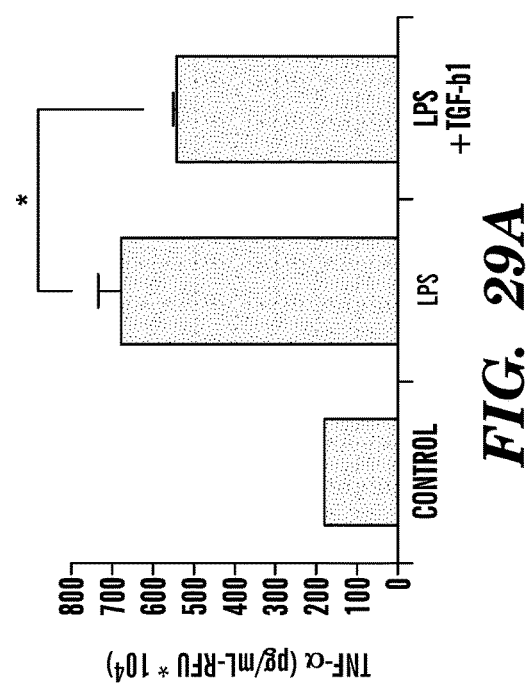
FIG. 30 demonstrates that laser actuated BSA:TGF-β1 NPs modulates TNF-α and IL-1b. Measurement of pro-inflammatory cytokine, TNF-α (FIG. 30A) and IL-1b (FIG. 30B), in primary BMDC after LPS induction and laser irradiation of BSA:TGF-β1 NPs at two doses following 24 hour incubation. Cytokine concentrations assessed with a TNF-α and IL-1b ELISA, respectively, and normalized to cell metabolic activity with Alamar Blue; quantitation by microplate reader (n=4, * indicates p<0.05). ND indicates levels below detectable range.
Figure 30B:
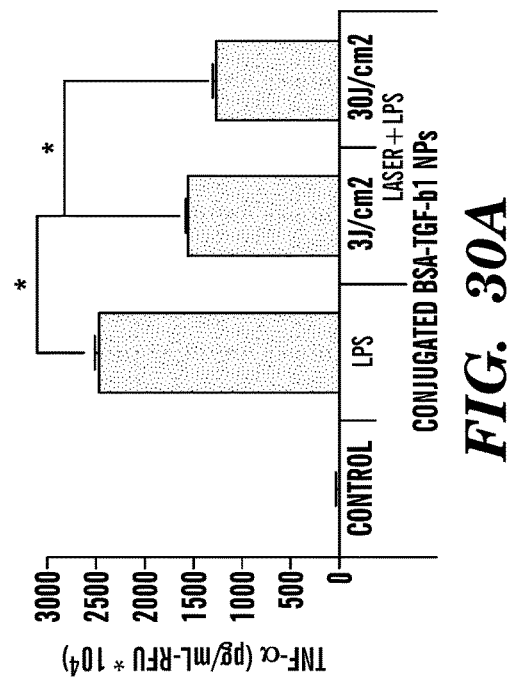

Laser actuated BSA:TGF-β1 NPs were able to significantly reduce levels of LPS stimulated TNF-α and IL-1b compared to control NPs (FIG. 30). It is noteworthy to point out that laser actuated BSA:TGF-β1 NPs at 30 J/cm2 showed greater reduction of LPS stimulated TNF-α and IL-1b compared to 3 J/cm2, demonstrating a dose dependent effect. This assay demonstrates the ability of laser actuated BSA-TGF-β1 NPs to reduce LPS induced immune response.

The present embodiments successfully demonstrate synthesis and characterization of albumin nanoparticles. The optical density measurement showed that BSA solution undergoing coacervation has the highest optical density after 2 hours of dropwise ethanol addition. At that point, there had been an approximately 2.7-fold volume of ethanol relative to initial volume of BSA solution. These results are in agreement with a previous study (Weber et al., 2000) in which particle size is controlled mainly by the amount of desolving agent added and addition of up to a 1.5-fold volume of ethanol relative to the volume of the initial albumin solution achieves optimal NP size, with more ethanol addition resulting in larger albumin NPs. They also conclude that further addition causes no change in particle size and only continued to increase particle concentration. After 2 hours and a 2.7-fold addition of ethanol to initial BSA solution, the optical density began to decrease due to protein aggregate formation that settled to the bottom of the solution, making the solution more transparent. These results demonstrate that ethanol addition (above 2.5-fold) will cause precipitation of the protein and affect particle size. This is likely to be due to the limited solubility of albumin in ethanol that leads to the aggregation and precipitation of albumin.

In addition, it was observed that the presence of salt in the NP solution played a role in the stability of the BSA NPs. Dialyzing the NPs against PBS or 1 mM NaCl resulted in aggregation of the protein and polydispersity of the NPs. The best quality NPs were found to be those dialyzed against 1 M NaCl, contributing to a high concentration of salt in the NPs, as seen by the SEM-EDS analysis. Others have reported a salt dependency on the surface charge of preformed HSA NPs, noting that increased PBS addition reduced their zeta potential. Langer et al., 2003. These observations with dialysis against different salt concentrations indicate an optimal concentration of salt necessary for NP stability. The salt can contribute to shielding surface charges on the BSA NPs and preventing formation of large BSA aggregates. One possibility could be explored in the future is the presence of salt contributing to salt bridging between protein NPs.

DLS and phase contrast microscopy confirmed the fabrication of BSA NPs were approximately 240 nm in PBS, the most physiologically relevant buffer. The reported fabrication of 280 nm HSA NPs was achieved using a similar ethanol coacervation process with an initial albumin solution of pH 7.0. Langer et al., 2003. As seen in Table 1, BSA NPs have different hydrodynamic diameters depending on analysis solution used. The size of the NP is an important design consideration because this parameter greatly influences the rate of elimination of the particle from circulation. In order for BSA NPs to take advantage of its targeting ability to sites of malignant and inflamed tissues through the EPR effect, it is necessary to have the most physiologically relevant in vivo hydrodynamic diameter. SEEC, which currently requires a dried sample, did not allow for accurate size measurements because the protein dehydrated and collapse in the absence of a solvent. An approach to perform SEEC in hydrating samples is currently being explored in the lab.

Biochemical assays confirmed that ROS modulates BSA NP conformation, as observed with BSA, by noting increased amounts of available free cysteines after the addition of $H_2O_2$. The cysteines residue has unique chemical properties that allow it to engage in a variety of redox reactions, making it a key residue in reacting with ROS. Le Moan et al., 476 Meths. Mol. Biol. 175 (2009). It is likely that ROS reduces disulfide linkages, contributing to the observed increase in free cysteines.

The present invention provides for the laser actuation of BSA:TGF-β1 NPs. The biochemical assays presented herein demonstrate the ability of laser actuation to modulate the conformation of BSA NPs through the same ROS mechanism discussed previously. Laser actuated BSA NPs showed a simultaneous increase in $H_2O_2$ and free cysteine levels. Because it is thought that the available cysteine-34 residue on albumin contributes to NP formation (Elzoghby, 2012), these results indicate that laser-mediated ROS generation can play a role in reducing disulfide linkages in the NP structure, allowing for more available free cysteines.

Although ROS can reduce disulfide linkages, there is no significant conformational change in BSA NPs actuated with laser, $H_2O_2$, or DTT. DTT is a known reducer of disulfide bonds, and insignificant change in hydrodynamic radius after DTT treatment supports the mechanism that ROS is responsible for modulating the conformation of the BSA NP by cleaving surface disulfide bonds.

Laser actuated BSA:TGF-β1 NPs demonstrated a similar increase in free cysteines as BSA NPs; and IAEDANs-tagged NPs confirmed low mobilited tagged complexes suggesting laser actuation induces conformational change without comprising the integrity of the NP. Current albumin NP delivery systems rely of biodegredation through enzymatic activity to release a therapeutic agent. The rate of enzymatic degradation is the crucial parameter for drug release, thus many surface modifications are being explored to control the kinetics of biodegradation in efforts to ensure NP stability and controlled drug release. Elzoghby, 2012, Langer et al., 2008. This work suggests a possible approach to overcome current limitations of albumin NP drug delivery systems by demonstrating the potential for laser actuation of the conformation of BSA NPs and BSA:TGF-β1 NPs, which effectively controls the release of a therapeutic agent.

The in vitro biological efficacy of BSA:TGF-β1 NPs as a model payload was developed herein. Initially, it was observed that BSA NPs embedded with TGF-β1 were extremely toxic to a number of cell lines and hence were no longer pursued in further experiments. Because the TGF-β1 was initially mixed in with the BSA solution prior to ethanol coacervation, it is possible that the coacervation had deleterious effects on the TGF-β1 molecule. In addition, TGF-β1 embedded into the NPs underwent extensive processing, including dialysis and lyophilization, compared to conjugated NPs, which can have contributed to the higher toxicity of these NPs.

Further, because ROS-modulated BSA NP conformational change appears to be a surface effect that does not significantly alter the NP structure, surface conjugation of BSA NPs with TGF-β1 was a more ideal strategy. In contrast, conventional NP formulations that rely on enzymatic degradation would embed the therapeutic agent to provide a protective environment for the drug, because there would be a complete breakdown of the NP for release and therapeutic efficacy. For example, research on embedded BMP-2 BSA NPs demonstrated that the amount of stabilizer used to coat the NPs influences the release rate of the growth factor [20, 50]. Wang et al., 2008; Zhang et al., 24 Biotechnol. Prog. 945 (2008). Because surface conformational change may not be enough for to release the embedded therapeutic agent, however, adsorption of the TGF-β1 onto the NP appears to be an ideal strategy to harness the potential of laser-actuated TGF-β1-loaded BSA NPs.

A TGF-β1 ELISA and epithelial TGF-β reporter cell line confirmed that laser-actuated BSA:TGF-β1 NPs significantly increased the bioavailability of the payload. It is noteworthy to mention that in the reporter cell line, a higher laser dose (30 J/cm2) resulted in a higher amount of bioavailable TGF-β1 compared to NPs treated with the standard 3 $J/cm^2$. This dose effect indicates that irradiation with a higher fluency can generate more ROS, which contributes to more reduction of disulfide linkages, and thus making more TGF-β1 bioavailable.

Furthermore, the laser-actuated BSA:TGF-β1 NPs demonstrated the capability of utilizing TGF-β1 to modulate immune response. LPS is a well-known strong activator of inflammatory reactions and up regulates the production of many cytokines. Mou et al., 2011. The NF-κB reporter assay showed that RAW 293 cells treated with laser-actuated BSA:TGF-β1 NPs had significantly lower SEAP activity, indicating TGF-β1 downregulation of immune response.

Further still, primary BMDCs showed increased expression of pro-inflammatory cytokines IL-1b and TNF-α when stimulated with LPS. Treatment with laser-actuated BSA:TGF-β1 NPs showed significant down-regulation of IL-1b and TNF-α compared to BSA:TGF-β1 NPs without laser actuation. Notably, there BSA:TGF-β1 NPs irradiated with 30 J/cm2 showed enhanced ability to down-regulate IL-1b and TNF-α compared to 3 J/cm2 suggesting a dose dependent effect. These observations are consistent with the data from the TGF-β1 reporter cell line demonstrating that higher laser doses increases the amount of bioavailable TGF-β1. Recently, it has been shown by others that LPS-stimulated RAW 264.7 cells express IL-1b and TNF-α in RAW 264.7 cells. Kawata et al., 151 J. Biochem. 205 (2012). Other studies have also found that TGF-β1 modulates LPS-induced cytokine production in DCs and prevents maturation of immature DCs, though the exact mechanism has yet to be fully determined. Geissmann et al., 162 J. Immunol. 4567 (1999); Mou et al., 2011.

The present results, taken together, suggest that laser-actuated BSA: TGF-β1 NPs can be used as a delivery system for TGF-β1 to modulate immune response, particularly as an immune modulator. Nevertheless, more work must be done to optimize the fabrication of NPs. Others have noted that the pH value of the albumin solution prior to the desolvation procedure was a major factor determining particle size and that varying this parameter led to NP sizes ranging from 150 nm to 280 nm, with higher pH values leading to smaller nanoparticles. Langer et al., 2003. It had also been reported that the size distribution and polydispersity of BSA NPs can be manipulated by controlling albumin concentration, pH value, non-solvent/water ratio and stirring rate. Wang et al., 2008. Thus, it is possible to adjust and optimize these parameters to fabricate NPs of a desired size in order to ensure targeting and delivery of the NPs.

The efficiency of drug loading onto the BSA NPs can be quantified further. It would also be interesting to further investigate how the zeta potential influences stability and laser-actuated BSA NP modulation. More work can also be done to understand the role of salt in the stability of BSA NPs both during and after fabrication. Whether the laser-actuation releases TGF-β1 from the NP or simply allows it to become more biologically available while remaining attached to the NPs can be determined. Several attempts have been made to quantify the release fraction by filtering laser-irradiated BSA:TGF-β1 NPs through a spin filter with a molecular weight cutoff of 100K to separate the released fraction from the bound BSA NP. It was observed, however, that there is significant loss when filtering recombinant TGF-β1 through the centrifuge device. Therefore, using this method does not appear to be an accurate way to measure TGF-β1 release at this time.

Figure 31:
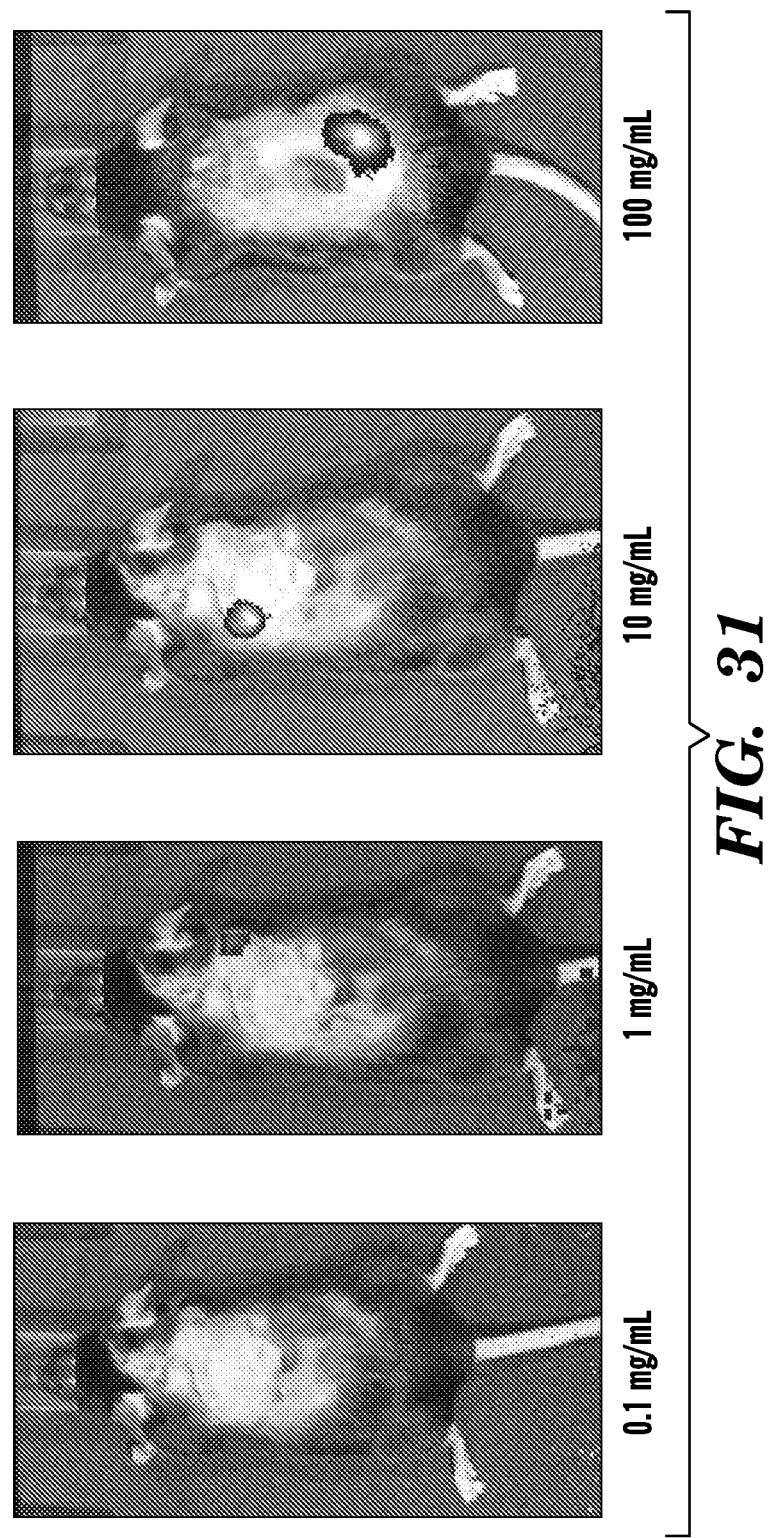
FIG. 31 presents in vivo visualization of BSA NPs tagged with Hylite-750 at different BSA NP concentrations. Imaging done with Xenogen IVIS-200 Imaging System.
Figure 32A:
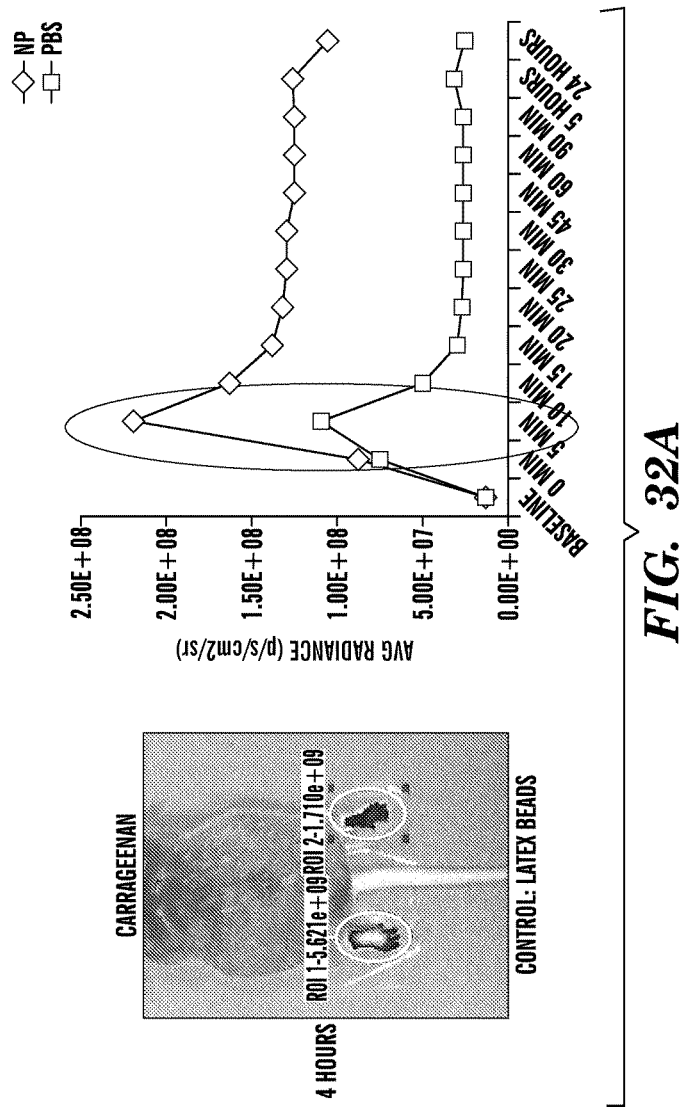
Figure 32C:
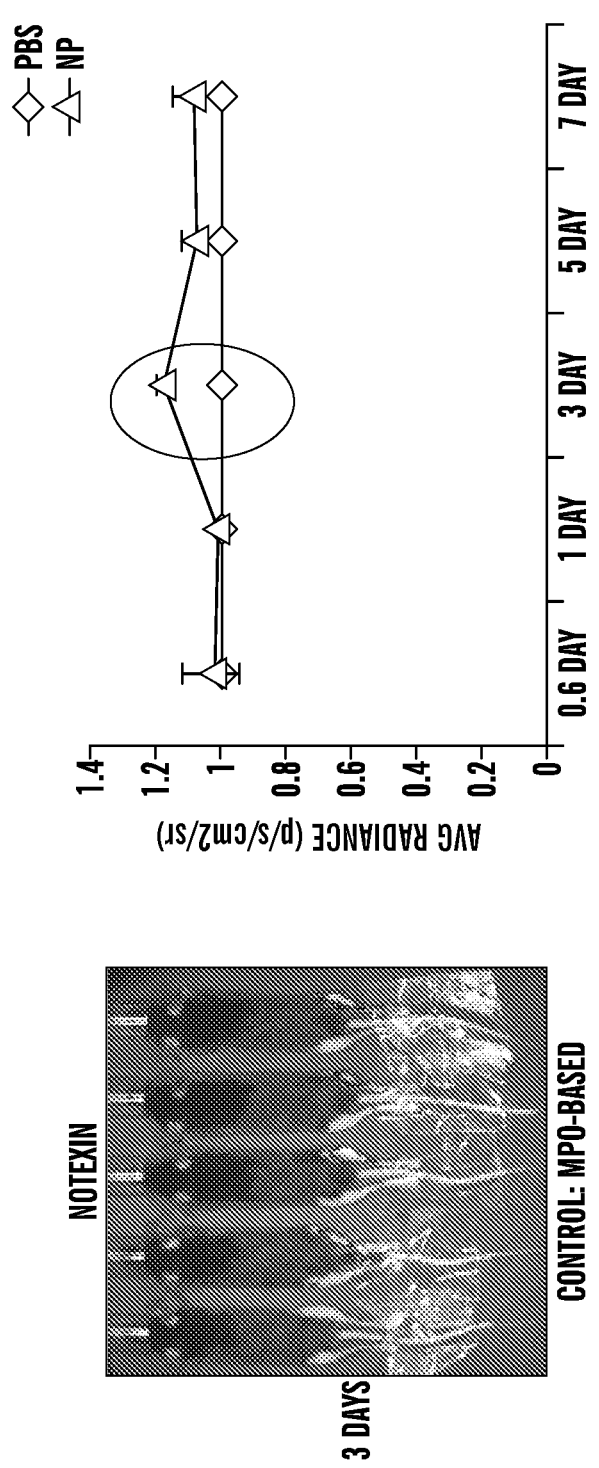
Figure 33A:
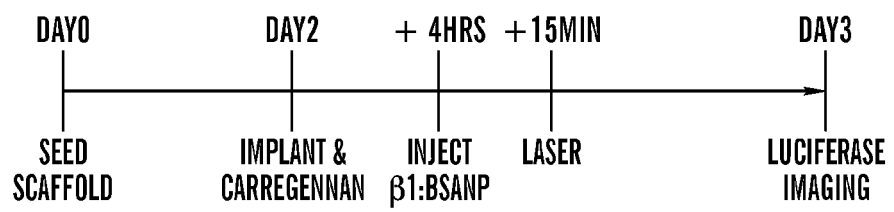
FIGS. 33A-33C shows that BSA NPs can deliver therapeutic payloads to localized sites.
Figure 33B:
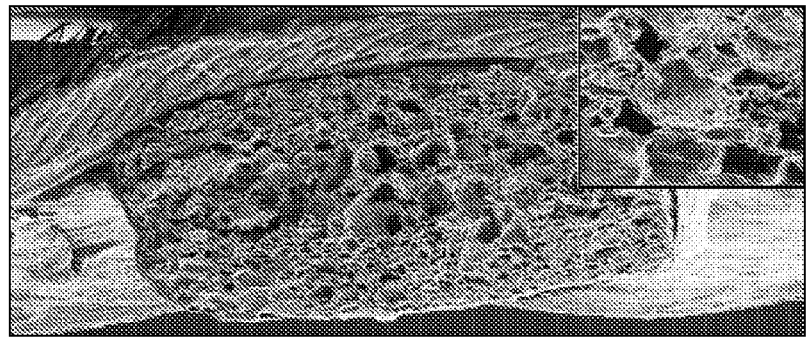
Figure 33C:
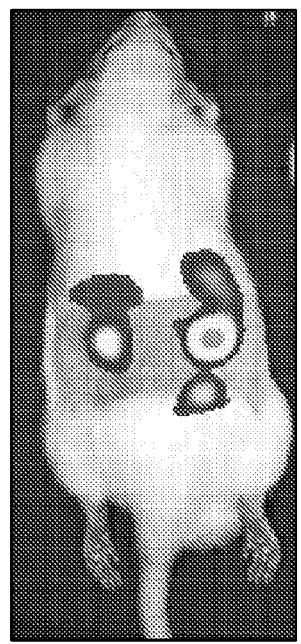
Figure 34A:
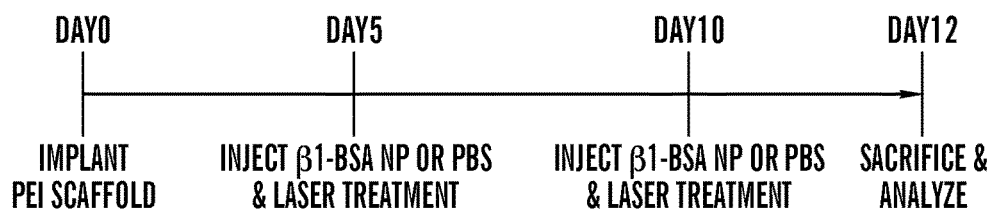
FIGS. 34A and 34B show that laser actuated TGF-β1:BSA NPs can induce FoxP3 $T_{Reg}$ response.
Figure 34B:
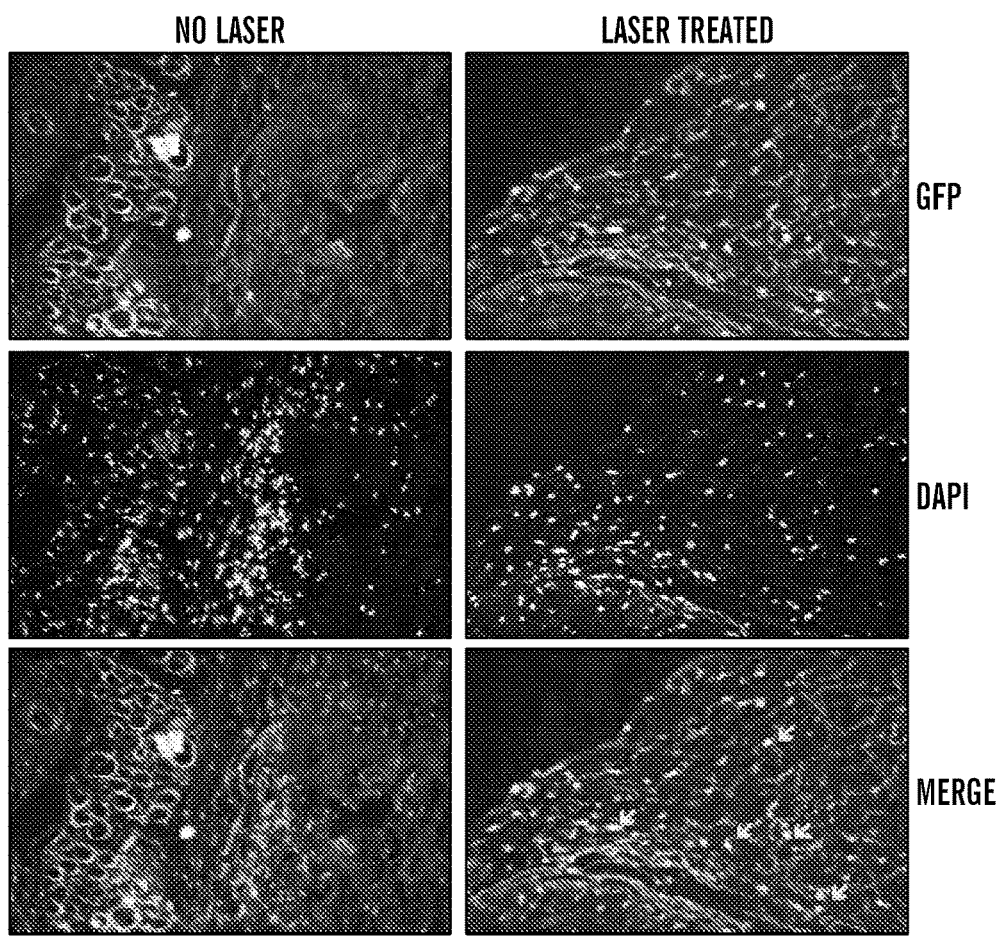

BSA NPs are attractive because of albumin's ideal targeting ability to sites of malignant and inflamed tissue. It has been demonstrated that high rates of albumin accumulation in inflamed paws of mice suffering from collagen-induced arthritis (CIA) (Wunder et al., 2003); however, it has not yet been shown that albumin NPs have the same capabilities. Thus, the next steps can include showing in vivo accumulation of albumin to sites of inflammation in efforts to use this system in a RA model. Preliminary steps have shown in vivo ability to visualize BSA NPs. BSA and BSA NPs were tagged with a fluorescent dye, Hylite 750, and injected subcutaneously into mice to determine skin attenuation and the minimum concentration necessary to visualize the NPs (FIG. 31). In vivo efficacies of the system in mice or other animal models at sites of inflammation are relevant preclinical studies. Local inflammatory sites are created in mice with an immune adjuvant, such as LPS and BSA:TGF-β1 NPs are subcutaneously injected. Upon accumulation of the NP in the inflammatory site, mice are subjected to laser actuation, which is expected to reduce levels of local inflammation.

In addition, due to the presence of functional groups on albumin NPs, surface modifications could be explored in albumin NPs to modify the pharmacokinetic profile of degradation, enhance the stability of the NP, prolong the circulation half-life, slow the drug release, or promote targeting capabilities. See, e.g., Elzoghby et al., 2012. Because the present work indicates an ROS-mediated disulfide reducing mechanism for conformational change, surface modifications by the use of ligands to create disulfide linkages between the therapeutic agent and the NP to be specifically cleaved on laser actuation can be explored further.

An embodiment of the present invention provides for a method for the preparation of an albumin nanoparticle conjugated to an active agent for in vivo delivery and laser actuation of the active agent, comprising (a) obtaining an albumin solution; (b) preparing NPs from the albumin by ethanol coacervation; (c) contacting the albumin NPs with the active agent and allowing the biomolecule to adsorb to the albumin NPs, thereby creating an albumin NP-biomolecule conjugate; wherein said albumin NPs have a diameter ranging from about 150 nm to about 350 nm, inclusive, and said NPs comprise about 1% to about 80% of active agent by total weight of the nanoparticle. In use, the conjugate is administered to a subject, and the subject is irradiated with low-level laser irradiation to induce conformational change in the conjugate and increase bioavailability of the active agent. The laser irradiation can be targeted to a specific tissue where therapeutic benefit is desired.

The active agents can include antineoplastic agents, cardiovascular agents, anti-inflammatory agents, antidiabetic agents, central nervous system agonists, central nervous system antagonists, immunosuppressants, tissue regeneration promoting factors, and antivirals. Specific active agents that can be incorporated into the methods of the current invention include, but are not limited to, paclitaxel, docetaxel, irinotecan, carmustine, doxorubicin, phenesterine, piposulfan, tamoxifen, lomustine, gambogic acid, oridonin, podophyllotoxin, atorvastatin, simvastatin, fenofibrate, nifedipine, ibuprofen, indomethacin, piroxicam, glyburide, diazepam, risperidone, ziprasidone, tacrolimus, rapamycin, indinavir, ritonavir, telaprevir, lopinavir, transferrin, insulin, endostatin, hemoglobin, myoglobin, lysozyme, immunoglobulins or portions thereof, α-2-macroglobulin, fibronectin, lamin, collagen, gelatin, artificial peptides and proteins, derivatives, variants, and analogues of the compounds listed herein, and combinations thereof. For example, the active agent comprises antineoplastic compounds, such as paclitaxel, docetaxel, irinotecan, carmustine, doxorubicin, phenesterine, piposulfan, tamoxifen, lomustine, gambogic acid, oridonin, or podophyllotoxin. It is also recognized that the pharmacologically active agents can include crystalline or amorphous forms of the compounds listed herein, including the solvate and non-solvate forms.

The albumin:active agent NP conjugates of the present invention are suitable for in vivo delivery As used herein, the term "in vivo delivery" refers to delivery of the conjugate by such routes of administration as oral, intravenous, subcutaneous, intraperitoneal, intrathecal, intranasal, intramuscular, inhalational, topical, transdermal, rectal (suppositories), vaginal, and the like. The present invention provides for laser-actuated albumin as a mechanism for conformational change and to increase the bioavailability of the conjugated active agent after its administration to a subject in need thereof. The novel ability for laser actuation provides a precisely modulated therapeutic delivery system.

Thus in one aspect, the present disclosure provides a method of actuating the delivery of an active agent to a cell comprising contacting the cell with a serum albumin nanoparticle active agent conjugate disclosed herein and irradiating the conjugate with low level laser irradiation such that the active agent becomes bioavailable to the cell.

In another aspect, the present disclsosure provides a method of increasing bioavailability of an active agent in a subject. The method comprising administering to the subject a serum albumin nanoparticle active agent conjugate disclosed herein and exposing the subject to low-level laser irradiation, wherein the exposure increases the bioavailability of the active agent.

The method of the invention can be used to increase the bioavailability of the active agent at a desired anatomic site of a subject by only irradiating the anatomic site where an increase in the bioavailability is desired. According, in on aspect, the present disclosure provides a method for increasing bioavailability of an active agent at an anatomic site of a subject. The method comprising administering to the subject a serum albumin nanoparticle active agent conjugate and exposing the anatomic site to low-level laser irradiation. As used herein, an "anatomic site" is predetermined site in a subject where the active agent is needed for action. Without wishing to be bound by a theory, the exposure of the anatomic site to the low-level laser irradiation increases the bioavailability of the active agent at the anatomic site relative to a site that is not exposed to the laser. This increases the activity the active agent at the desired site while remaining substantially inactive at sites not exposed to the laser. It is believed that increasing the local bioavailability of the active agent at a desired site can allow larger doses of active agents to be delivered, more bioactivity to result from lower doses, and a reduction in side effects of the active agent.

The disclosure also provide a method of decreasing NFκB reporter activity, suppressing IL-1b, or suppressing TNF-α levels in a cell, comprising contacting the cell with the serum albumin nanoparticle cytokine conjugate and irradiating the conjugate. In some embodiments, the cytokine is TGF-β1.

The methods disclosed herein can also be used for treating a subject suffering from an immune disorder comprising administering a serum albumin nanoparticle TGF-β1 conjugate and exposing the subject to low-level laser irradiation. Exposure to the laser irradiation increases the bioavailability of TGF-β1. The laser irradiation can be applied to a desired anatomic site to increase the bioavalibility of TGF-β1 at a desired site of action.

Exemplary immune disorders include, but are not limited to, rheumatoid arthritis, diabetes, Lupus, eczema, asthma, psoriasis, multiple sclerosis, myopathy, nephropathy, a neurodegenerative disorder, graft-versus-host-disease (GVHD), inflammatory bowel disease (IBD), Crohn's disease, or necroinflammatory liver disease.

Generally, the term "treatment" or "treating" is defined as the application or administration of a therapeutic agent to a patient, or application or administration of a therapeutic agent to an isolated tissue or cell line from a patient, said patient having a disease, a symptom of disease or a predisposition toward a disease, with the purpose to cure, heal, alleviate, relieve, alter, remedy, ameliorate, improve or affect the disease, the symptoms of disease or the predisposition toward disease. Thus, treating can include suppressing, inhibiting, preventing, treating, or a combination thereof. Treating refers, inter alia, to increasing time to sustained progression, expediting remission, inducing remission, augmenting remission, speeding recovery, increasing efficacy of or decreasing resistance to alternative therapeutics, or a combination thereof. "Suppressing" or "inhibiting", refers, inter alia, to delaying the onset of symptoms, preventing relapse to a disease, decreasing the number or frequency of relapse episodes, increasing latency between symptomatic episodes, reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof. In one embodiment the symptoms are primary, while in another embodiment symptoms are secondary. "Primary" refers to a symptom that is a direct result of a disorder, e.g., diabetes, while, secondary refers to a symptom that is derived from or consequent to a primary cause. Symptoms can be any manifestation of a disease or pathological condition. Also encompassed by "treatment" is a reduction of pathological consequence of a disease. The methods of the invention contemplate any one or more of these aspects of treatment.

Accordingly, as used herein, the term "treatment" or "treating" includes any administration of albumin:active agent NP and includes: (i) preventing the disease from occurring in a subject which can be predisposed to the disease but does not yet experience or display the pathology or symptomatology of the disease; (ii) inhibiting the disease in an subject that is experiencing or displaying the pathology or symptomatology of the diseased (i.e., arresting further development of the pathology and/or symptomatology); or (iii) ameliorating the disease in a subject that is experiencing or displaying the pathology or symptomatology of the diseased (i.e., reversing the pathology and/or symptomatology).

By "treatment", "prevention" or "amelioration" of a disease or disorder is meant delaying or preventing the onset of such a disease or disorder, reversing, alleviating, ameliorating, inhibiting, slowing down or stopping the progression, aggravation or deterioration the progression or severity of a condition associated with such a disease or disorder. In one embodiment, the symptoms of a disease or disorder are alleviated by at least 5%, at least 10%, at least 20%, at least 30%, at least 40%, or at least 50%.

Efficacy of treatment can be determined in association with any known method for diagnosing the disorder. Alleviation of one or more symptoms of the disorder indicates that the compound confers a clinical benefit. Any of the therapeutic methods described to above can be applied to any suitable subject including, for example, mammals such as dogs, cats, cows, horses, rabbits, monkeys, and most preferably, humans.

Upon laser actuation, the bioavailability of the active agent is increased, for example, about 10% to 20%, 20% to 30%, 30% to 40%, 40% to 50%, 50% to 60%, 60% to 70%, 70% to 80%, 80% to 90%, 90% to 100%, or 100% to 200%, compared to the bioavailability of the active agent without laser actuation. Additionally, the effectiveness of the active agent can be enhanced by at least about 10%, including for example at least about any of 20%, 30%, 40%, 50%, 60%, 70%, 80%, 90%, 100%, 200%, or more, inclusive, compared to the effectiveness without laser actuation.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein. The terms, "patient" and "subject" are used interchangeably herein. A subject can be male or female.

Preferably, the subject is a mammal. The mammal can be a human, non-human primate, canine, rodent (e.g., mouse or rat), feline, horse, or bovine, but are not limited to these examples.

Mammals other than humans can be advantageously used as subjects that represent animal models of human diseases and disorders. In addition, albumin:active agent NP compositions and methods described herein can be used to treat domesticated animals and/or pets.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of albumin:active agent NP includes both methods practiced on the human body and also the foregoing activities.

As used herein, the term "administer" refers to the placement of a composition into a subject by a method or route which results in at least partial localization of the composition at a desired site such that desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are administered by intravenous infusion or injection.

Administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the compounds are formulated into ointments, salves, gels, or creams as generally known in the art.

The phrase "therapeutically-effective amount" as used herein means that amount of a compound, material, or composition which is effective for producing some desired therapeutic effect in at least a sub-population of cells in a subject at a reasonable benefit/risk ratio applicable to any medical treatment. Thus, "therapeutically effective amount" means that amount which, when administered to a subject for treating a disease, is sufficient to effect such treatment for the disease.

The term "effective amount" used herein in the context of treatment refers to an amount of a compound or composition sufficient to treat a specified disorder, condition or disease such as ameliorate, palliate, lessen, and/or delay one or more of its symptoms. In the context of enhancing delivery, access, and other effectiveness aspects facilitated/mediated by the laser actuation of the albumin:active agent NP compositions, effective amount refers to amount sufficient to obtain these goals, such as an amount of composition and application of laser irradiation effective to increase bioavailability of the therapeutic agent to a target tissue.

By "an amount sufficient to treat" is meant the amount of a compound required to improve, inhibit, or ameliorate a condition of a subject, or a symptom of a disease, in a clinically relevant manner. Any improvement in the subject is considered sufficient to achieve treatment.

Determination of an effective amount is well within the capability of those skilled in the art. Generally, the actual effective amount can vary with the specific compound, the use or application technique, the desired effect, the duration of the effect and side effects, the subject's history, age, condition, sex, as well as the severity and type of the medical condition in the subject, and administration of other pharmaceutically active agents. Accordingly, an effective dose of compound described herein is an amount sufficient to produce at least some desired therapeutic effect in a subject.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of use or administration utilized.

The effective dose can be estimated initially from cell culture assays. A dose can be formulated in animal models to achieve a circulating plasma concentration range that includes the $IC_{50}$ (i.e., the concentration of the therapeutic which achieves a half-maximal inhibition of symptoms) as determined in cell culture. Levels in plasma can be measured, for example, by high performance liquid chromatography. The effects of any particular dosage can be monitored by a suitable bioassay. The effective plasma concentration for a compound as disclosed herein can be about 0.01 µM to about 10 µM, about 0.2 µM to about 5 µM, or about 0.8 to about 3 µM in a subject, such as a rat, dog, or human.

Generally, the albumin:active agent NP are administered so that the active agent is used or given at a dose from 1 µg/kg to 1000 mg/kg; 1 µg/kg to 500 mg/kg; 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. Further contemplated is a dose (either as a bolus or continuous infusion) of about 0.1 mg/kg to about 10 mg/kg, about 0.3 mg/kg to about 5 mg/kg, or 0.5 mg/kg to about 3 mg/kg. It is to be further understood that the ranges intermediate to those given above are also within the scope of this disclosure, for example, in the range 1 mg/kg to 10 mg/kg, for example use or dose ranges such as 2 mg/kg to 8 mg/kg, 3 mg/kg to 7 mg/kg, 4 mg/kg to 6 mg/kg, and the like.

Not only is albumin considered an ideal drug carrier, the availability of many surface residues contributes to albumin's high binding capacity for many drugs; thus, it is possible to incorporate a wide variety of active agents and surface modifications with this novel delivery system to provide controlled therapeutic benefits. Albumin-based NP drug delivery systems continue to grow as an area of biomedical research. The present work demonstrates a reproducible coacervation procedure for the preparation of BSA NPs between 150 nm-350 nm, inclusive, such as 200 nm-300 nm, inclusive. It is possible to adjust and optimize these parameters to fabricate NPs of a desired size in order to ensure targeting and delivery of the NPs, as noted herein and elsewhere. The present invention provides for laser-actuated BSA: TGF-β1 NP as a mechanism for conformational change and to increase the bioavailability and immune-modulatory effects of TGF-β1. The novel ability for laser actuation to provide a precisely modulated therapeutic delivery system opens exciting avenues of application.

Albumin

Albumin is a simple protein found in serum and has a molecular weight of about 66,000 Daltons. Albumin is produced in the liver and is the most abundant blood plasma protein. Albumin polypeptides are important in regulating blood volume by maintaining appropriate colloid osmotic pressure. Human serum albumin is a monomer of 585 amino acid residues, and includes three homologous a-helical domains: domain I, domain II and domain III. Each domain contains 10 helices and is divided into antiparallel six-helix and four-helix subdomains. Deletion studies suggest that domain III alone is sufficient for binding to FcRn (Chaudhury et al., Biochemistry 2006, 45:4983-4990). A truncated human albumin that does not bind FcRn and has a low serum level has been identified (Andersen et al., Clin Biochem., 2010, 43(45):367-72. Epub 2009 Dec. 16).

Albumin is known to bind and carry a Wide variety of small molecules, including lipid soluble hormones, bile salts, unconjugated bilirubin, fatty acids, calcium, ions, transferrin, hemin, and tryptophan. Albumin also binds various drugs such as Warfarin, phenobutazone, clofibrate and phenyloin, and its binding can alter the drugs' pharmacokinetic properties.

The albumin can be a naturally occurring albumin, an albumin related protein or a variant thereof such as a natural or engineered variant. Variants include polymorphisms, fragments such as domains and subdomains, fragments and/or fusion proteins. An albumin can comprise the sequence of an albumin protein obtained from any source. Typically the source is mammalian such as human or bovine. In some embodiments, the serum albumin is human serum albumin ("HSA").

The term "human serum albumin" includes a serum albumin having an amino acid sequence naturally occurring in humans, and variants thereof. The HSA coding sequence is obtainable by known methods for isolating cDNA corresponding to human genes, and is also disclosed in, for example, EP 0 073 646 and EP 0 286 424, content of both of which is incorporated by reference in their entirety. A fragment or variant can be functional or non-functional. For example, a fragment or variant can retain the ability to bind to an albumin receptor such as FcRn to at least 10, 20, 30, 40, 50, 60, 70, 80, 90 or 100% of the ability of the parent albumin (from which the fragment or variant derives) to bind to the receptor. Relative binding ability can be determined by methods known in the art such as surface plasmon resonance studies.

The albumin can be a naturally-occurring polymorphic variant of human albumin or of a human albumin analogue. Generally, variants or fragments of human albumin will have at least 5%, 10%, 15%, 20%, 30%, 40%, 50%, 60%, 70%, (preferably at least 80%, 90%, 95%, 100%, 105% or more) of human albumin's ligand binding activity (for example FcRN-binding), mole for mole.

The albumin can comprise the sequence of bovine serum albumin. The term "bovine serum albumin" includes a serum albumin having an amino acid sequence naturally occurring in cows, for example as taken from Swissprot accession number P02769, and variants thereof as defined herein. The term "bovine serum albumin" also includes fragments of full-length bovine serum albumin or variants thereof, as defined herein.

A number of proteins are known to exist within the albumin family. Accordingly, the albumin can comprise the sequence of an albumin derived from one of serum albumin from African clawed frog (e.g., see Swissprot accession number P08759-1), bovine (e.g., see Swissprot accession number P02769-1), cat (e.g., see Swissprot accession number P49064-1), chicken (e.g., see Swissprot accession number P19121-1), chicken ovalbumin (e.g., see Swissprot accession number P01012-1), cobra ALB (e.g., see Swissprot accession number Q91134-1), dog (e.g., see Swissprot accession number P49822-1), donkey (e.g., see Swissprot accession number QSXLE4-1), European water frog (e.g., see Swissprot accession number Q9YGH6-1), blood fluke (e.g., see Swissprot accession number AAL08579 and Q95VB7-1), Mongolian gerbil (e.g., see Swissprot accession number O35090-1 and JC5838), goat (e.g., see Swissprot accession number B3VHM9-1 and as available from Sigma as product no. A2514 or A4164), guinea pig (e.g., see Swissprot accession number Q6WDN9-1), hamster (see DeMarco et al. (2007). International Journal for Parasitology 37(11): 1201-1208), horse (e.g., see Swissprot accession number P35747-1), human (e.g., see Swissprot accession number P02768-1), Australian Lung-fish (e.g., see Swissprot accession number P83517), macaque (*Rhesus* monkey) (e.g., see Swissprot accession number Q28522-), mouse (e.g., see Swissprot accession number P07724-1), North American bull frog (e.g., see Swissprot accession number P21847-1), pig (e.g., see Swissprot accession number P08835-1), pigeon (e.g. as defined by Khan et al, 2002, 1112. J. Biol. Macromol, 30(3-4), 171-8), rabbit (e.g., see Swissprot accession number P490 65-1), rat (e.g., see Swissprot accession number P02770-1), salamander (e.g., see Swissprot accession number Q8UW05-1), salmon ALB1 (e.g., see Swissprot accession number P21848-1), salmon ALB2 (e.g., see Swissprot accession number Q03156-1), sea lamprey (e.g., see Swissprot accession number Q91274-1 and O42279-1) sheep (e.g., see Swissprot accession number P14639-1), Sumatran orangutan (e.g., see Swissprot accession number Q5NVH5-1), tuatara (e.g., see Swissprot accession number Q8JIA9-1), turkey ovalbumin (e.g., see Swissprot accession number O73860-1), Western clawed frog (e.g., see Swissprot accession number Q6D.I95-1), and includes variants and fragments thereof as defined herein.

Many naturally occurring mutant forms of albumin are known. Many are described in Peters, (1996, All About Albumin: Biochemistry, Genetics and Medical Applications, Academic Press, Inc., San Diego, Calif., p. 170-181), content of which is incorporated herein by reference. A variant as defined herein can be one of these naturally occurring mutants such as those described in Minchiotti et al. (2008). Hum Mutat 29(8): 1007-16, content of which is incorporated herein by reference in its entirety.

A "variant albumin" refers to an albumin protein wherein at one or more positions there have been amino acid insertions, deletions, or substitutions, either conservative or non-conservative, provided that such changes result in an albumin protein for which at least one basic property, for example binding activity (type of and specific activity e.g. binding to bilirubin or a fatty acid such as a long-chain fatty acids, for exampleoleic (C18:1), palmitic (C16:0), linoleic (C18:2), stearic (C18:0), arachidonic (C20:4) and/or palmitoleic (C16:1)), osmolarity (oncotic pressure, colloid osmotic pressure), behaviour in a certain pH-range (pH-stability) has not significantly been changed. "Significantly" in this context means that one skilled in the art would say that the properties of the variant can still be different but would not be unobvious over the ones of the original protein, e.g. the protein from which the variant is derived. Such characteristics can be used as additional selection criteria in the invention.

The term albumin also encompasses albumin variants, such as genetically engineered forms, mutated forms, and fragments etc. having one or more binding sites that are analogous to a binding site unique for one or more albumins as defined above. By analogous binding sites in the context of the invention are contemplated structures that are able to compete with each other for binding to one and the same ligand structure.

In some embodiments, the albumin can be human serum albumin extracted from serum or plasma, or recombinant human albumin (rHA) produced by transforming or transfecting an organism with a nucleotide coding sequence encoding the amino acid sequence of human serum albumin, including rHA produced using transgenic animals or plants.

In one embodiment, albumin is bovine serum albumin and includes variants and fragments thereof.

Nanoparticles

As used herein, the term "nanoparticle" refers to particle having a particle size of about 0.1 nm to about 1000 nm. For example, a nanoparticle can have a particle size of about 50 nm to about 750 nm, about 100 nm to about 500 nm, about 150 nm to about 450 nm, or about 200 nm to about 350 nm. In some embodiments, a nanoparticle can have a size of 150 nm-350 nm, inclusive, such as 200 nm-300 nm, inclusive.

It will be understood by one of ordinary skill in the art that particles usually exhibit a distribution of particle sizes around the indicated "size." Unless otherwise stated, the term "particle size" as used herein refers to the mode of a size distribution of particles, i.e., the value that occurs most frequently in the size distribution. Methods for measuring the particle size are known to a skilled artisan, e.g., by dynamic light scattering (such as photocorrelation spectroscopy, laser diffraction, low-angle laser light scattering (LALLS), and medium-angle laser light scattering (MALLS)), light obscuration methods (such as Coulter analysis method), or other techniques (such as rheology, and light or electron microscopy).

In some embodiments, the particles can be substantially spherical. What is meant by "substantially spherical" is that the ratio of the lengths of the longest to the shortest perpendicular axes of the particle cross section is less than or equal to about 1.5. Substantially spherical does not require a line of symmetry. Further, the particles can have surface texturing, such as lines or indentations or protuberances that are small in scale when compared to the overall size of the particle and still be substantially spherical. In some embodiments, the ratio of lengths between the longest and shortest axes of the particle is less than or equal to about 1.5, less than or equal to about 1.45, less than or equal to about 1.4, less than or equal to about 1.35, less than or equal to about 1.30, less than or equal to about 1.25, less than or equal to about 1.20, less than or equal to about 1.15 less than or equal to about 1.1. Without wishing to be bound by a theory, surface contact is minimized in particles that are substantially spherical, which minimizes the undesirable agglomeration of the particles upon storage. Many crystals or flakes have flat surfaces that can allow large surface contact areas where agglomeration can occur by ionic or non-ionic interactions. A sphere permits contact over a much smaller area.

In some embodiments, the particles have substantially the same particle size. Particles having a broad size distribution where there are both relatively big and small particles allow for the smaller particles to fill in the gaps between the larger particles, thereby creating new contact surfaces. A broad size distribution can result in larger spheres by creating many contact opportunities for binding agglomeration. The particles described herein are within a narrow size distribution, thereby minimizing opportunities for contact agglomeration. What is meant by a "narrow size distribution" is a particle size distribution that has a ratio of the volume diameter of the 90th percentile of the small spherical particles to the volume diameter of the 10th percentile less than or equal to 5. In some embodiments, the volume diameter of the 90th percentile of the small spherical particles to the volume diameter of the 10th percentile is less than or equal to 4.5, less than or equal to 4, less than or equal to 3.5, less than or equal to 3, less than or equal to 2.5, less than or equal to 2, less than or equal to 1.5, less than or equal to 1.45, less than or equal to 1.40, less than or equal to 1.35, less than or equal to 1.3, less than or equal to 1.25, less than or equal to 1.20, less than or equal to 1.15, or less than or equal to 1.1.

Geometric Standard Deviation (GSD) can also be used to indicate the narrow size distribution. GSD calculations involved determining the effective cutoff diameter (ECD) at the cumulative less than percentages of 15.9% and 84.1%.

GSD is equal to the square root of the ratio of the ECD less than 84.17% to ECD less than 15.9%. The GSD has a narrow size distribution when GSD<2.5. In some embodiments, GSD is less than 2, less than 1.75, or less than 1.5. In one embodiment, GSD is less than 1.8.

In some embodiments, the nanoparticle comprises the active agent adsorbed on the albumin particle.

Amount of the active agent in the albumin:active agent NP can range from about 0.01% to about 99% (w/w) of the nanoparticle. For example, albumin:active agent NP can comprise from about 0.1 to about 95%, from about 0.5% to about 85%, from about 1% to about 80%, from about 5% to about 75%, from about 10% to about 70%, or from about 15% to about 60% of active agent by total weight of the nanoparticle.

Active Agent

Without limitations, the active agent can be a compound selected from the group consisting of small organic or inorganic molecules; saccharines; oligosaccharides; polysaccharides; biological macromolecules, e.g., peptides, proteins, and peptide analogs and derivatives; peptidomimetics; antibodies, antigen binding fragments of antibodies, nucleic acids, e.g., oligonucleotides, antisense oligonucleotides, siRNAs, shRNAs, ribozymes, aptamers, microRNAs, pre-microRNAs, plasmid DNA, etc. . . . ; nucleic acid analogs and derivatives; an extract made from biological materials such as bacteria, plants, fungi, or animal cells; animal tissues; naturally occurring or synthetic compositions; and any combinations thereof.

Exemplary active agents include pharmaceutically active agent described in, but are not limited to, those found in *Harrison's Principles of Internal Medicine,* 13$^{th}$ Edition, Eds. T. R. Harrison et al. McGraw-Hill N.Y., NY; Physicians' Desk Reference, 50$^{th}$ Edition, 1997, Oradell N.J., Medical Economics Co.; Pharmacological Basis of Therapeutics, 8$^{th}$ Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete contents of all of which are incorporated herein by reference.

In some embodiments, the active agent can be selected from the group consisting of 1018-iss, 1311-hua33, 13-cis-retinoic acid, 18f-fdg, 1d09c3, 2-pentenylpenicillin, 825780 dna antiviral vaccine, a/t/s, erythromycin, a-1 antitrypsin, abacivir; lamivudine, abarelix, abatacept, abciximab, abetimus sodium, abn 912, abt 325/abt 874, abt 874, abx-i18, ac vaccine, ac162352, ac2592, acadesine, acamprosate, acarbore, acarbose, acatophenazine, acc-001, acebutolol, acebutolol hydrochloride, aceclofenac, acetamide, acetaminophen, acetaminophen; aspirin; caffeine, acetaminophen; butalbitol, acetaminophen; codeine phosphate, acetazolamide, acetazolamide sodium, acetic acid, acetic acid; hydrocortisone, acetohexamide, acetohydroxamic acid, acetophenazine, acetyl sulfisoxazole, acetylcholine chloride, acetylcysteine, acetylsalicylic acid, acid glycoprotein, acitretin, aclometasone, acrivastine; pseudoephedrine, actemra, acth, activated recombinant factor vii, acyclovir, acyclovir sodium, adalimumab, adapalene, adefovir dipivoxil, ademetionine, adenine, adeno associated viral vector, adenosine, adenoviral vector, adenovirus, adenovirus p53, adinazolam, adiponectin, adpedf, adrafinil, adrenaline, adrenocorticotropic hormone, advate antihemophilic factor plasma/albumin-free method, advexin, aeg 35156, afelimomab, ag-707, agalsidase alpha, agalsidase beta, aglucosidase alpha, ags-psca mab, agtc 0106, ahnotriptan, albendazole, albumin iodinated i-125 serum, albumin iodinated i-131 serum, albumin, human, albuterol, albuterol sulfate, albuterol; ipatropium, alclometasone dipropionate, alcohol, aldesleukin, aldesleukin, il2, aldosterone, alefacept, alemtuzumab, alendronate, alendronic acid; colecalciferol, alfentanil, alfentanil hcl, alfentanil hydrochloride, alferon n injection, alfimeprase, alfuzosin, alfuzosin hcl, alglucerase, alicaforsen, alitretinoin, alizapride, allopurinol, allopurinol sodium, allovectin-7, allylprodine, alminoprofen, almotriptan, alosetron hcl, alperopride, alpha-1 antitrypsin, alpha-1 proteinase inhibitor, alpha-galactosidase a, alphaprodine, alpidem, alprazolam, alprostadil, alseroxion, alteplase (tpa), altretamine, altu-238, aluminum hydroxide, aluminum hydroxide; magnesium carbonate, alvac el2otmg, alvac gp100, alvac mn120 tmgmp, alvac-cea/b7.1, amantadine, amantadine hydrochloride, ambenonium chloride, ambrisentan, amcinonide, ame 527, amerscaen medronate ii, amerscam stannous agent, amerscan hepatate ii, amesergide, amfenac, amg 108/amg 531/amg 623/amg 714, amg 221, amg 317, amg 403, amg 517, amg102/amg 386/amg 479/amg 623/amg 655/amg 706, amifostine, amikacin sodium, amikacin sulfate, amiloride hydrochloride, amiloride hydrochloride dihydrate, amino acids, amino acids; glycerin; electrolytes, amino alcohol, aminoacetic acid, aminocaproic acid, aminoglutethimide, aminohippurate sodium, aminolevulinic acid, aminolevulinic acid hydrochloride, aminophylline, aminopropylon, aminosalicylic acid, amiodarone, amiodarone hcl, amiodarone hydrochloride, amisulpride, amitriptyline, amitriptyline hydrochloride, amitriptyline; chlordiazipoxide, amixetrine, amlexanox, amlodipine, amlodipine besylate, amlodipine; atorvastatin, amlodipine; benazepril, ammonium chloride, ammonium lactate, amobarbital sodium; ecobarbital sodium, amoxapine, amoxicillin, amoxicillin; clarithromycin; lansoprazole, amperozide, amphenidone, amphetamine, amphetamine; dextroamphetamine, amphotericin b, ampicillin, ampicillin and sulbactam, ampicillin sodium, ampicillin trihydrate, ampicillin; clavulonate, amprenavir, aminone lactate, amylin, amylpenicillin, amytal sodium, anagrelide hydrochloride, anakinra, anastrazole, andropinirole, androstenedione, angiocol, angiotensinogen, anidulafungin, anileridine, anisindione, an-sulfur colloid, anti-cd16 mab, anti-cd23 mab, anti-cd3 mab, anti-cd80 mab, antidiuretic hormone, antihemophelic factor (factor viii), antihemophilic factor (recombinant), anti-hiv-1 mab, anti-hsp90 mab, anti-idiotype cancer vacccine, anti-ige, anti-il-4, anti-inhibitor coagulant complex, anti-interferon-gamma, anti-lfa-1, mouse, anti-human, monoclonal antibody, anti-lymphotoxin beta receptor mab, antimullerian hormone, anti-pem mab, antisense oligonucleotide, anti-staph mab, anti-tac(fv)-pe38 immunotixin, antivenin crotalidae polyvalent injection, antivenin lactrodectus mactans, antivenin micrurus fulvius, apazone, apc8024, aplidine, apo21/trial (amg 951), apo-cilazapril/hctz, apo-digoxin, apo-etidronate, apo-feno-super, apo-flecamide, apokyn, apo-levetiracetam, apo-medroxy, apo-meloxicam, apo-methotrexate, apo-metoprolol sr, apo-midodrine, apo-mirtazapine, apomorphine, apomorphine hydrochloride, apomorphinediacetate, apo-omeprazole, apo-ondansetron, apo-oxcarbazepine, apo-ramipril, apo-ranitidine, apo-risperidone, apo-sumatriptan, apo-topiramate, apraclonidine, aprepitant, aprotinin bovine, argatroban, arginine hydrochloride, arimoclomol, aripiprazole, arsenic trioxide, articaine hydrochloride/epinephrine, asparaginase, aspirin, aspirin; caffeine; orphenadrine citrate, aspirin; dipyridamole, aspirin; hydrocodeine; caffeine, aspirin; hydrocodone, aspirin; meprobamate, aspirin; pravastatin, at-1001, atazanivir sulfate, atenolol, atenolol; chlorthalidone, atl 1101, atl 1102, atomoxetine, atorvastatin calcium, atovaquone, atovaquone; proguanil hcl, atracurium besylate, atrial natriuretic peptide, atropine sulfate, atropine sulfate/edrophonium chloride, attenuated live measles vaccine, attenuated rotavirus vaccine, auranofin, aurexis tefibazumab, autologous renal cell tumor vaccine, autologous tumor, autologus gp100-reactive pbl and til plus rf-gp100p209, ave 0005, ave 9633 maytansin-loaded anti-cd 33 mab, avi-4065, aviptadil, avr 118, avx101, azacitidine, azacyclonol, azatadine, azathioprine, azathioprine sodium, azelaic acid, azelastine, azelastine hcl, azidocillin, azithromycin, azt; 3tc; abacavir, aztreonam, aztreonam lysinate, bacampicillin, bacille calmette-guerin, bacitracin, bacitracin zinc, bacitracin; polymyxin b sulfate, baclofen, bacterial lipase, bacteriostatic sodium chloride, bacteriostatic water, bapineuzumab, barium sulfate, basiliximab, bavituximab, bcl-2 antisense oligonucleotide, g-3139, becaplermin, becatecarin, beclomethasone dipropionate, belatacept, benactyzine, benazepril hydrochloride, benazepril; hydrochlorothiazide, bendroflumethiazide, bendroflumethiazide; nadolol, benmoxine, benoxaprofen, benperidol, benserazide, bentoquatam, benzamycin, benzoic acid, benzonatate, benzoyl peroxide, benzoyl peroxide; clindamycin, benzphetamine, benzphetamine; diethylpropion, benzpiperylon, benzquinamide, benzquinamide hydrochloride, benztropine, benztropine mesylate, benzydramine, benzylmorphine, benzylpenicillin, beractant, bertezomib, beta-2, betahistine, betaine, betaine anhydrous, betamethasone acetate, betamethasone dipropionate, betamethasone sodium phosphate, betamethasone valerate, betaseron, betaxolol, betaxolol hydrochloride, bethanechol chloride, bevacizumab, bexarotene, bezitramide, bicalutamide, bimatoprost, bimosiamose disodium, binedaline, biperiden, biphasic insulin aspart, bisoprolol fumarate, bitolterol, bitolterol mesylate, bivalirudin, bivatuzumab, bleomycin, bleomycin sulfate, blx 883, bortezomib, bosentan, botulinum toxin type a+b, bovine bile extract, br3-fc, bretylium tosylate, brimonidine tartrate, brinzolamide, brofaromine, bromelain; vit c; I glutamine; msm; quercetin, bromfenac, bromisovalum, bromocriptine, bromocriptine mesylate, bromodiphenhydramine; codeine, brompheniramine; dextromethorphin; pseudoephedrine, brompheniramine; pseudophedrine, brompheniramine; pseuodophedrine, bromopride, bromperidol, brompheniramine, brompheniramine maleate, brucine, buclizine, budesonide, budesonide; formoterol fumarate, budesonide; formoterol, budipine, bufexamac, buffered intrathecal electrolytes/dextrose, bumetanide, bupivacaine hydrochloride, bupivacaine hydrochloride/epinephrine, bupivacaine hydrochloride/epinephrine bitartrate, bupivocaine; lidocaine, buprenorphine, buprenorphine hydrochloride, buprenorphine hydrochloride/naloxone hydrochloride, bupropion, bupropion hydrochloride, buramate, busalazide disodium, buserelin, buspirone, buspirone hydrochloride, busulfan, butabarbital, butaclamol, butalbital, butalbital; acetaminophen, butalbital; acetaminophen; caffeine, butalbital; apap, butalbital; asa, butanamide, butaperazine, butenafine hcl, butoconazole nitrate, butorphanol, butorphanol tartrate, butriptyline, ca4p, cabergoline, caffeine, caffeine citrate, caffeine; ergotamine, caiv-t, calciferol, calcipotriene, calcitonin, calcitonin, salmon, calcitriol, calcium acetate, calcium carbonate; residronate, calcium chloride, calcium disodium versenate, calcium gluconate, calcium-n-carboamoylaspartate, calfactant, candesartan, cannobinoids, capecitabine, capreomycin sulfate, capromab pendetide, captodiamine, captopril, captopril; hctz, capuride, carbachol, carbamazepine, carbamic acid, carbcloral, carbenicillin, carbidopa, carbidopa; levodopa, carbinoxamine maleate, carbiphene, carbocaine, carbon 13 urea, carbon 14 urea, carboplatin, carboprost tromethamine, carboxylic acid, carboxypeptidase, carbromal, cardioplegic solution, cardiotrophin-1, carfecillin, carindacillin, carisoprodol, carmustine, caroxazone, carphenazine, carpipramine, carprofen, carteolol hydrochloride, carvedilol, caspofungin acetate, caspofungin msd, cat 3888, catumaxomab, cb 001, cc10, ccr5 mab, cdp 791, cea, cefaclor, cefadroxil, cefamandole, cefazolin, cefazolin sodium, cefdinir, cefditoren pivoxil, cefepime hydrochloride, cefibutin, cefinetazole, cefixime, cefinetazole, cefoperazone, cefotaxime, cefotaxime sodium, cefotetan, cefoxitin, cefoxitin sodium, cefpodoxime proxetil, cefprozil, ceftazidime, ceftazidime sodium, ceftriaxone, ceftriaxone sodium, cefuroxime, cefuroxime axetil, cefuroxime sodium, celecoxib, cell therapy, cellular implant therapy, cephacetrile, cephalexin, cephaloglycin, cephaloridine, cephalosporin c, cephalosporins, cephalotin, cephamycin a, cephamycin b, cephamycin c, cephamycins, cepharin, cephradine, cere-110, cere-120, cerebro, ceredase, ceretec, cericlamine, certolizumab pegol, ceti-1 vaccine, cetrizine, cetrorelix, cetuximab, cevimeline hcl, cevimeline hcl, chimeric mab, chimeric monoclonal antibody, chimeric tumornecrosis therapy (tnt), chimeric-anti-interleukin-6 monoclonal antibody, chir-12.12, chloralbetaine, chlorambucil, chloramphenicol, chloramphenicol sodium succinate, chlordiazepoxide, chlorhexidine gluconate, chlorobutinpenicillin, chloromycetin, chloroprocaine, chloroprocaine hydrochloride, chloroquine phosphate, chlorothiazide, chlorothiazide sodium, chloroxine, chlorpheniramine, chlorpheniramine; hydrocodone, chlorpromazine, chlorpromazine hydrochloride, chlorpromazine hydrochloride intensol, chlorpropamide, chlorprothixene, chlorthalidone, chlorthiazide; reserpine, chlorzoxazone, cholecystokinin, cholest-4-en-3-one, oxime, cholestyramine, cholic acid, choline, choriogonadotropin alfa, chorionic gonadotropin, chromic chloride, chromic phosphate p32, chromitope sodium, ciclesonide, ciclopirox, ciclopirox olamine, cicloprilax, ciclosporin, cidofovir, cilazaprol, cilengitide, cilostazol, cimetidine, cimetidine hydrochloride, cinacalcet, cinchophen, cinmetacin, cinnarizine, cipramadol, ciprofloxacin, ciprofloxacin hydrochloride, ciprofloxacin; dexmtheasone, cisatracurium besylate, cis-mdp, cisplatin, cisplatin/5-fu therapy, citalopram, citalopram hydrobromide, cladribine, clarithromycin, clebopride, clemastine, clemastine fumarate, clindamycin hydrochloride, clindamycin injection, usp, clindamycin phosphate, clindamycin; benzoyl peroxide, clioquinol, clioquinol; hydrocortisone, clobenzepam, clobetasol, clobetasol propionate, clocapramine, clocortolone pivalate, clofarabine, clofibrate, clomacran, clometacin, clometocillin, clomiphene citrate, clomipramine, clomipramine hydrochloride, clonazepam, clonidine, clonidine hydrochloride, clonidine; chlorthalidone, clonitazene, clonixin, clopenthixol, clopidogrel, clopriac, clorazepate dipotassium, clospirazine, clothiapine, clotrimazole, clotrimazole; betamethasone, clovoxamine, cloxacillin, cloxacillin sodium, clozapine, cmc-544, cmd-193, cnto 1275, cnto 328, co bicalutamide, co cilazapril, co fluconazole, co fosinopril, co ipra-sal, co risperidone, co salbut-iprat inhalation solution, co topiramate, cobalt chloride, codeine, codeine phosphate, codeine; chlorpheniramine, colchicines; probenicid, colesevelam hcl, colestipol hcl, colfosceril palmitate, colistimethate, colistimethate sodium, collagenase, compazine, conivaptan hydrochloride, copper, corticorelin ovine triflutate, corticotropin, corticotropin-releasing hormone, cortisone acetate, co-sertraline, cotinine, cp-547,632, cp-751, 871, cpg 7909, cr0002, crisantaspase, cromolyn sodium, cromolyn sulfate, crotamiton, cs 1008, ctg cca cgt tct cct gc-, cupric chloride, cyamemazine, cyanocobalamin, cyclacillin, cyclizine, cyclobenzaprine, cyclobenzaprine hydrochloride, cyclopentolate hydrochloride, cyclopentolate; phenylephrine, cyclophosphamide, cyclosporin, cyclosporin a, cyclosporine, cyproheptadine, cyproheptadine hydrochloride, cysteinyl leukotrienes, cytarabine, cytomegalovirus immune globulin (cmv-igiv), dacarbazine, daclizumab, dactinomycin, dalteparin sodium, danazol, dantrolene sodium, dapsone, daptomycin, darbepoetin alpha, darifenacin hcl, darunavir, dasatinib, daunorubicin citrate, daunorubicin hydrochloride (plus liposomal), ddavp, decitabine, deferiprone, deferoxamine mesylate, defibrotide, dehydroepiandrosterone, delavirdine mesylate, demeclocycline hydrochloride, dendritic cell vaccine, denileukin diftitox, denosumab, denufosol tetrasodium, deoxygalactonojirimycin hydrochloride, deoxyribose phosphorothioate, deprenyl, desflurane, desipramine, desipramine hydrochloride, desirudin, desirudin recombinant, desloratadine, desmodus rotundus salivary plasminogen activator (dspa), desmopressin acetate, desogestrel, desogestrel; ethinyl estradiol, desonide, desoximetasone, deuterium oxide, dexamethasone, dexamethasone intensol, dexamethasone sodium phosphate, dexchlorpheniramine maleate, dexfenfluramine, dexmedetomidine, dexmethylphenidate hcl, dexrazoxane, dexrazoxane hydrochloride, dextramethorphan; guafenisin; pseudophedrine, dextroamphetamine, dextroamphetamine saccharate, dextroamphetamine sulfate, dextromethorphan, dextromoramide, dextropropoxyphene, dextrose, dextrose dialysis solution, diaminopyridine phosphate, diamorphine, diatrizoate meglumine, diatrizoate sodium, diazepam, diazoxide, dibenzyline, diboterminalpha, diclofenac, diclofenac; misoprostol, dicloxacillin, dicloxacillin sodium, dicyclomine hydrochloride, didanosine, diethylpropion, difenoxin; atropine, diflorasone diacetate, diflunisal, digoxin, dihydrocodeine, dihydroergokryptine, dihydroergotamine, dihydroergotamine mesylate, diltiazem, diltiazem hydrochloride, dimenhydrinate, dimercaprol, dimethyl sulfoxide, dimethylphenidate, dinaprostone, dinoprostone, diphenhydramine, diphenhydramine hydrochloride, diphenicillin, diphenidol, diphenoxylate, diphenoxylate; atropine, diphenylcyclopropenone, diphtheria/tetanus/pertussis/hepatitis b vaccine, diphtheria/tetanus/pertussis/hepatitis b/poliomylelitis vaccine, diphylline, dipipanone, dipivefrin hydrochloride, diptheria/tetanus/hepatitis b/poliomyelitis/hib/perutssis vaccine, dipyridamole, disopyramide phosphate, disulfuram, dmsa, dna nanoparticle gene therapy, dna vaccine, dnase, dobutamine hydrochloride, docetaxel, docosahexaenoic acid, docosanol, dofetilide, dolasetron mesylate monohydrate, dolasetronmethanesulfonate, dolophine hydrochloride, dom-alendronate, dom-alendronate, dom-anagrelide, dom-bicalutamide, dom-citalopram, dom-doxycycline, domeridone, dom-hydrochlorothiazide, dom-mirtazapine, dom-ondanssetron, dom-risperidone, dom-simvastatin, dom-ursodiol c, donepezil, dopamine, dopamine hydrochloride, dornase alfa, dorzolamide, dorzolamide; timolol, dosulepin, doxacalciferol, doxapram hydrochloride, doxazosin mesylate, doxepin, doxepin hydrochloride, doxorubicin, doxorubicin carbon/iron, doxorubicin hydrochloride, doxorubicin polyisohexylcyanoacrylate nanoparticles, doxycycline, doxycycline hyclate, doxylamine, doxylamine succinate, dronabinol, droperidol, droprenilamin hcl, drospirenone; estradiol, drosporenone; ethinyl estradiol, drotrecogin alpha, dtp vaccine, dtpa, duloxetine, duramycin, dutasteride, dx-88, dx-890, dyphylline, e. coli heat-shock protein 70 with bovine retinal s-antigen, e.e.s. erythromycin, ethylsuccinate, econazole nitrate, ecromeximab, ecteinascidin 743, eculizumab, edetate calcium disodium, edetate disodium, edrophonium chloride, efalizumab, efavirenz, eflornithine, egen-001, electrolyte irrigation solution, eletriptan, eliprodil, emd 273063, emedastine difumarate, emtricitabine, enalapril, enalapril maleate, enalapril maleate; felodipine, enalapril; diltiazem, enalaprilat, enciprazine, endrophonium chloride, enflurane, enfuvirtide, engineered protein inhibitor of human neutrophil elastase, enoxaparin sodium, entacapone, entecavir, enzastaurin hydrochloride, ephedrine, epinastine hcl, epinephrine, epinephrine, epirubicin hydrochloride, eplerenone, epoetin alfa, epo-fc, epoprostenol sodium, epothilone b, eprosartan, epstein-barr virus vaccine, eptacog alfa, eptastigmine, eptifibatide, eptoterminalpha, ergocalciferol, ergolinepramipexole, ergoloid mesylates, ergotamine, ergotamine tartrate, ergotamine; caffeine, erlotinib, ertapenem sodium, erythrocin stearate, erythromycin, erythromycin base, erythromycin estolate, erythromycin ethylsuccinate, erythromycin lactobionate, erythromycin stearate, erythromycin; sulfisoxazole, erythropoietin, erythropoietin b, escitalopram, escitalopram oxalate, esmolol hydrochloride, esomeprazole sodium, estazolam, estradiol, estradiol acetate, estradiol cypionate, estradiol hemihydrate and progesterone, estradiol valerate, estradiol; norethindrone, estramustine phosphate, estriol, estrogen; progesterone, estrogens, conjugated, estrogens; medroxyprogesterone, estrone, estropipate, eszopiclone, etamiphyllin, etanercept, etaqualone, ethacrynate sodium, ethacrynic acid, ethambutol, ethambutol hydrochloride, ethanol, ethanolamine oleate, ethiinyl estradiol; ethynadiol acetate, ethinyl estradil; levonorgestrel, ethinyl estradiol, ethinyl estradiol; norethindrone, ethinyl estradiol; levonorgestrel, ethinylestradiol; levonogestrel, ethiodized oil, ethionamide, ethoheptazine, ethosuximide, ethotoin, ethyl eicosopentaenoate, ethynylcytidine, eti-201, etidronate disodium, etilefrin, etodolac, etoposide, etoposide phosphate, eu/3/04/247, exemestane, exenatide lar, exenatide synthetic, extended phenyloin sodium, ezetimibe, factor ix complex (konyne 80, profilnine heat-treated, proplex sx-t, proplex-t), factor vii, factor viii, factor xi, famciclovir, famotidine, felbamate, felodipine, fenfluramine, fenofibrate, fenoldopam mesylate, fenoprofen calcium, fentanyl, fentanyl citrate, ferumoxides, ferumoxsil, fexofenadine, fexofenadine hydrochloride, fgf-1, fgf-5 peptides, fibrin sealant, fibroblast growth factor 1, fientanyl, filgrastim, finasteride, flavoxate hydrochloride, flecamide acetate, flesinoxan, floxuridine, fluconazole, flucytosine, fludarabine phosphate, fludeoxyglucose, fludeoxyglucose f-18, fludrocortisone acetate, flumazenil, flunisolide, fluocinolone acetonide, fluocinolone; tetrinoin; hydroquinone, fluocinonide, fluoromethalone acetate, fluorometholone, fluorouracil, fluoxetine, fluoxetine hydrochloride, fluoxymesterone, flupenthixol, fluphenazine, fluphenazine decanoate, fluphenazine hydrochloride, flupirtine, flurandrenolide, flurazepam, flurazepam hydrochloride, flurbiprofen, flurbiprofen sodium, fluspirilene, flutamide, fluticasone propionate, fluvastatin, fluvoxamine, fluvoxamine maleate, folic acid, follicle-stimulating hormone, follitropin alfa/beta, fomepizole, fondaparinux sodium, formivirsen, formoterol fumarate, fosamprenavir, fosamprenavir calcium, foscavir, fosfomycin; tromethamine, fosinopril, fosinopril sodium, fosphenyloin sodium, frovatriptan, fulvestrant, fumagillin, furosemide, g17(9) gastrin-diphtheria toxoid conjugate, gabapentin, gadobenate dimeglumine, gadodiamide, gadopentetate dimeglumine, gadoteridol, gadoversetamide, ga-gcb, galanthamine, gallium citrate ga 67, gallium nitrate, galsulfase, gamunex, ganciclovir, ganciclovir sodium, ganirelix acetate, garamycin, gastrin, gatifloxacin, gefitinib, gemcitabine hydrochloride, gemfibrozil, gemifloxacin mesylate, gemtuzumab ozofamicin, gene therapy, gentamicin, gentamicin sulfate, gepirone, ghrelin, gimatecan, g-interferon, glatiramer acetate, gliatak, gliclazide, glimepiride, glimepiride, glipizide, glipizide; mefformin, glucagon, glucocorticoids, glutathione, glyburide, glyburide; metformin, glyceryl trinitrate, glycine, glycopyrrolate, gm-csf, gmk, golimumab, gonadotropic, chorionic, gonadotropin-releasing hormone, goserelin acetate, gramicidin; neomycin; polymyxin b sulfate, granisetron, granisetron hydrochloride, griseofulvin, group c meningococcal conjugate vaccine, growth hormone, gti2040, guaifenesin, guaifenesin; pseuodoephedrine, guanabenz acetate, guanfacine hydrochloride, guanidine hydrochloride, gusperimus trihydrochloride, gvak (leukemia, pancreatic, prostate), *h. pylori* urease breathe test, halcinonide, halobetasol propionate, halofuginone hydrobromide, haloperidol, haloperidol decanoate, haloperidol lactate, haloperidole, halothane, hctz; irbesartan, hctz; olmesartan, hctz; quinipril, hctz; spironolactone, heliox, heparin sodium, hepatitis a & b vaccine, hepatitis a vaccine inactivated, hepatitis b immune globulin, hepatitis b vaccine, hepatitis c immunoglobulin, hepatocyte growth factor gene therapy, heptylpenicillin, herpes dna vaccine, herpes simplex virus, hetacillin, hexachlorocyclohexane, hexachlorophene, hexavalent vaccine, hgs-etr1/hgs-etr2, hgs-tr2j, hgtv43 gene medicine, hib vaccine, hib; neisseria mening; hep b antigen vaccine, histamine dihydrochloride, histrelin, hiv dna vaccine, hiv recombinant vaccine, hla-b27 derived peptide, homatoprine methylbromide, homoharringtonine, homoharringtonine, hrecombinant atiii, h-tyrosine-glycine-phenylalanine-glycine-glycine-oh, huc242-dm4, human alpha1-proteinase inhibitor, human chorionic gonadotropin, human cytomegalovirus immunoglobulin, human hpv vaccine, human immunoglobulin, human interleukin-2, human liver cell therapy, human menopausal gonadotropin, human monoclonal antibody, human monoclonal antibody ab88bv59, human monoclonal antibody against hla-dr, human monoclonal hepatitis b immunoglobulins, human normal immunoglobulin (ivig, human placental lactogen, human *staphylococcus aureus* immunoglobulin, human telomerase reverse transcriptase peptide, humanized agonistic anti-cd28 monoclonal antibody, humax-cd20, humax-cd4, humax-egfr, hun901-dml, huzaf, hyaluronidase, hydralazine hydrochloride, hydralazine; hctz, hydralazine; hydrochlorothiazide, hydralazine; isdn, hydrazine, hydrochlorothiazide, hydrocodone bitartrate, hydrocodone; acetaminophen, hydrocodone; homatropine, hydrocodone; ibuprofen, hydrocortisone, hydrocortisone sodium succinate, hydrocortisone valerate, hydrocortisone; neomycin; polymixin b, hydrocortisone; pramoxine, hydroflumethiazide, hydrogenated ergot alkaloids, hydromorphone, hydromorphone hydrochloride, hydroxocobalamin, hydroxyamphetamine; tropicamide, hydroxychloroquine sulfate, hydroxyethyl starch, hydroxypropyl cellulose, hydroxyurea, hydroxyzine, hydroxyzine hydrochloride, hydroxyzine pamoate, hyoscine, ibandronic acid, ibuprofen, ibuprofen; pseudoephedrine, ibutilide fumarate, icatibant acetate, icodextrin, idarubicin hydrochloride, idazoxan, idebenone, idoxuridine, iduronate-2-sulfatase, idursulfase, ifosfamide, ign101, ign311, il 13-pe38qqr, il-1r, il-2, il-2/ep, il-21, il-4r, iloprost, ima-638, imatinib, imatinib mesilate, imatinib mesylate, imc-3g3/imc-11f8/imc-18f1/imc-1121b/imc-a12, imexon, imiglucerase, imipramine, imipramine hydrochloride, imiquimod, immu-100/immu-101/immu-102/immu-105/immu-106/immu-107, immune globulin, inactivated hepatitis a virus; hepatitis b surface antigen suspension, inactivated hepatitis b vaccine, inactivated polio virus vaccine, inactivated rabies virus vaccine, inaminone lactate, indapamide, indiclor, indinavir, indium dtpa in 111, indium in 111 chloride, indium in 111 oxyquinoline, indium in 111 pentetate disodium, indium in 111 pentetreotide, indocyanine green, indomethacin, indomethacin sodium, indoprofen, infliximab, ing 1, ingap peptide, ingn 225/ingn 234/ingn 241/ingn 401, inhibin, inn-carglumic acid, inn-ivabradine, inno 102, inno-105/inno-305/inno-406, inn-protein c, inolimomab, ins37217, insulin (r dna origin), insulin (recombinant human), insulin aspart, insulin aspart recombinant, insulin detemir recombinant, insulin glargine recombinant, insulin glusine, insulin lispro protamine recombinant, insulin purified pork, insulin zinc, insulin-like growth factor, interferon alfa-2a, interferon alfason-1, interferon alpha, interferon b 1a, interferon beta 1-b, interferon beta gene delivery, interferon beta-1a, interferon gamma, interferon gamma-1b, interferon omega, interleukin-1 trap, interleukin-3/interleukin-12, intravenous immune globulin, iobenguane sulfate i 131, iodinated 125 albumin, iodinated 131 albumin, iodine, iodipamide meglumine, iodixanol, iodo-1-phenylalanine, iohexyl, iopamidol, iothalamate meglumine, iothalamate sodium, ioversol, ioxaglate meglumine, ioxaglate sodium, ipilimumab, ipratropium bromide, iproniazid, ipsapiraone, ir103 w/amplivax, irbesartan, irbesartan; hctz, irbesartan; hydrochlorothiazide, irinotecan hydrochloride, iron dextran, iron sucrose, isf 154, isis 113715, isis 301012, isocarboxazid, isoetharine hydrochloride, isoflurane, isoleucine, isometheptene, isoniazid, isophane insulin, isoproterenol, isoproterenol bitartrate, isoproterenol hydrochloride, isosorbide dinitrate, isosorbide mononitrate, isosulfan blue, isotonic gentamicin sulfate, isotretinoin, isradipine, itraconazole, iv fat emulsion, iv lipids, ivabradine, ivermectin, kanamycin, kanamycin sulfate, ketamine, ketamine hydrochloride, ketoconazole, ketoprofen, ketorolac, ketorolac tromethamine, ketotifen, kitanserin, kl-4 peptide+lipid, kos-862/kos-953 kp-1461, labetalol hydrochloride, lactated ringer's, lactoferin, lactulose, l-alphaacetylmethadol, lamivudine, lamivudine; zidovudine, lamotrigine, lanreotide, lansoprazole, lanthanum carbonate, laronidase, l-asparaginase, latanoprost, lazabemide, leflunomide, lenalidomide, lentiviral vector, lep-etu/lep-sn38, lepirudin recombinant, leptin, lerafaon-etu, lesopitron, lestaurtinib, letrozole, leucovorin calcium, leuprolide, leuprolide acetate, levalbuterol hydrochloride, levamisol hydrochloride, levetiracetam, levobunolol hydrochloride, levocabastine, levocarnitine, levodopa, levodopa and carbidopa, levodopa; carbdopa, levofloxacin, levonorgestrel, levorphan tartrate, levorphanol, levorphanol tartrate, levothyroxine sodium, liarozole, lidocaine, lidocaine hydrochloride, lidocaine; prilocalne, lidocaine; tetracaine, lignocaine; polymyxin b sulfate, lincomycin hydrochloride, linezolid, liothyronine sodium, liposomal doxorubicin, liposomal morphine, liraglutide, lisinopril, lisinopril; hctz, lisuride, lithium carbonate, lithium citrate, live, attenuated typhoid vaccine, l-lysine-n-acetyl-l-cysteinate, Iodine, lodoxamide tromethamine, lofentanil, lofepramine, lomefloxacin hcl, lomustine, loperamide hydrochloride, lopinovir; ritonavir, loprazolam, loracarbef, loratidine, lorazepam, losartan; hctz, losartan; hydrochlorothiazide, loteprednol, loteprednol etabonate, lovastatin, lovastatin; niacin, loxaglate sodium, loxapine, loxapine succinate, loxilan, lumigan; timolol, lumiracoxib, lusupultide, luteinizing hormone, ly 2181308, ly2275796, lymphostat-b, lysine acetate, m m r vax ii injection, m.t.e.-4/m.t.e-6, m195-bismuth 213 conjugate, m200, mab hefi-1, mafenide acetate, mage-3, magnesium chloride, magnesium sulfate, malathion, mangafodinir trisodium, manganese chloride, mannitol, mannitolum, maprotiline hydrochloride, maprotoline, mart-1 melanoma vaccine, matuzumab, mazipredone, mdx-060, mdx-066, mdx-070, mdx-1100, mdx-1303, mdx-214, measles mumps rubella vaccine, measles mumps vaccine, mebendazole, mebrofenin, mecamylamine hcl, mecasermin, mecasermin recombinant, mecasermin rinfabate, mecasermin rinfabate recombinant, mechlorethamine hydrochloride, meclizine hydrochloride, meclofenamate, meclofenamate sodium, mecloqualone, medetomidine, medi-507 siplizumab, medi-522, medi-528 anti-il-9 mab, medi-534 rsv/piv-3 vaccine, medi-545, medifoxamine, medroxyprogesterone acetate, mefenamic acid, mefloquine, mefloquine hydrochloride, megestrol acetate, melanocyte-stimulating hormone, melatonin, melonom tumor-reactive autologous til, meloxicam, melperone, melphalan hydrochloride, memantine, meningococcal group c vaccine, meningococcal polysaccharide vaccine, menotropins, menthol, mepenzolate, meperidine, meperidine hcl, meperidine hydrochloride, mepivacaine hydrochloride, mepivicaine; levonordefrin, mepolizumab, meprobamate, meptazinol, mequinol; tretinoin, mercaptamine bitartrate, mercaptopurine, meropenem, mesalamine, mesalamine; 5-asa, mesna, mesoridazine, metampicillin, metaproterenol, metaproterenol sulfate, metaraminol bitartrate, metastable technetium 99 demogastrin 2, metaxalone, metformin, metformin hydrochloride, metformin; pioglitazone, metformin; rosiglitazone, methacholine chloride, methadone hydrochloride, methamphetamine hcl, methaqualone, methazolamide, methenamine hippurate, methenamine mandelate, methicillin, methimazole, methocarbamol, methohexital sodium, methotrexate, methotrexate sodium, methotrimeprazine, methoxsalen, methprylon, methscopolamine, methsuximide, methyclothiazide, methyl aminolevukinate, methyldopa, methyldopa; hctz, methyldopate hydrochloride, methylene-tetrahydrofolate, methylene-tetrahydrofolic acid, methylergonovine maleate, methylphenidate, methylphenidate hydrochloride, methylphosphorothioate oligonucleotide, methylprednisolone, methylprednisolone acetate, methylprednisolone sodium succinate, methyltestosterone, methyphenidate, methyprylon, methysergide, metipranolol, metoclopramide, metoclopramide hydrochloride, metofenazate, metolazone, metomidate, metopimazine, metopon, metoprolol, metoprolol tartrate, metralindole, metronidazole, metronidazole; nystatin, metyrapone, metyrosine, mexiletine hydrochloride, mg98, mianserin, micafungin sodium, miconazole, micophenolic acid, micro+4/micro+5/micro+6/micro cr/micro cu/micro i/micro mn/micro se, midazolam, midazolam hydrochloride, midodrine hydrochloride, midostaurin, mifepristone, miglitol, miglustat, milnacipran, milrinone lactate, miltefosine, minaprine, minocycline, minocycline hydrochloride, minoxidil, mirtazapine, misoprostol, mitomycin, mitotane, mitoxantrone, mitoxantrone hydrochloride, mivacurium chloride, min 1202, min-02, mm-093, mmr; chicken pox vaccine, moclobemide, modafinil, moexipril hcl; hydrochlorothiazide, moexipril hydrochloride, mofegiline, molindone hcl, mometasone furoate, monobenzone, monoclonal antibody to human interleukin-6, monocyte-derived activated killer (mak) cells, montelukast sodium, morab 003, morab 009, moricizine, morphine, morphine sulfate, mosquirix malaria vaccine, moxifloxacin hydrochloride, mpi dmsa kidney reagent, mpi dtpa kit—chelate, mpi indium dtpa in 111, multi-11/multi-12, multivitamin infusion, mumps vaccine, mupirocin, muramyl tripeptide phosphatidyl ethanolamine, murine anti-idiotypic antibody against oc125 antibody against ca125 antigen, murine monoclonal antibody mab ar 20.5, muromonab-cd3, m-vax, mycophenolate mofetil hydrochloride, myeloma-derived idiotypic antigen vaccine, yo-029, myristoylated-peptidyl-, nabilone, nabumetone, n-acetylgalactosamine-4-sulfatase, n-acetylsarcosyl-glycyl-l-valyl-d-allo-isoleucyl-l-threonyl-l-norvalyl-l-isoleucyl-l-arginyl-l-prolyl-n-ethylamide, nadolol, nadrolone decanoate, nadroparin, nafcillin, nafcillin sodium, naftifine, nalbuphine, nalbuphine hydrochloride, nalidixic acid, nalmefene, nalmefene hydrochloride, nalorphine, naloxone, naloxone hydrochloride, naltrexone, naltrexone hydrochloride, nandrolone decanoate, nanopeptide paclitaxel, naphazoline hydrochloride, naphazoline; antazoline, naphazoline; pheniramin, naproxen, naproxen sodium, naratriptan, natalizumab, natamycin, natarelin acetate, nateglinide, n-azaphenyl-aminothiopyrrole, nbi-5788, nbi-6024, n-carbamyl-l-glutamic acid, nedocromil sodium, nefazodone, nefazodone hydrochloride, nefopam, nelarabine, nelfinavir, nemorubicin hydrochloride, neomycin neomycin sulfate, nepafenac, nesiritide recombinant, neuradiab, neuropeptide y, nevirapine, niacin, nicardipine hydrochloride, nicergoline, nicotine, nicotine polacrilex, nifedipine, nilotinib, nilutamide, nimoripine, nimotuzumab, nisoldipine, nisoxetine, nitazoxamide, nitisinone, nitisinone, nitrofurantoin, nitrofurazone, nitroglycerin, nitrous oxide, nitrous oxide; oxygen (50:50), nizatidine, nix p101, nm01, nofetumomab, nomifensine, noradrenaline, norepinephrine bitartrate, norethindrone, norethindrone acetate, norfloxacin, norgestrel; ethinyl estradiol, norlegestromin; ethinyl estradiol, nortriptyline, nortriptyline hydrochloride, nt501 ciliary neurotrophic factor, nystatin, nystatin; triamcinolone, obestatin, ocrelizumab, octreotide acetate, ofloxacin, ogx-011, okt3-gamma-1, olanzapine, oligonucleotide phosphorothioate, olopatadine hydrochloride, olsalazine sodium, omalizumab, omega 3 and ethyl esters, omeprazole, omoconazole, ondansetron, ondansetron hydrochloride, ondansetron hydrochloride dihydrate, ondansetron omega, opebacan, opium tincture, oprelvekin, oral cholera vaccine, oral recombinant human growth hormone, oral recombinant parathyroid hormone 1-34, oregovomab, orlistat, orphenadrine, orphenadrine citrate, orphendrine; aspirin; caffeine, oseltamivir phosphate, osteogenic protein-1 i, oxacillin sodium, oxaliplatin, oxalobacter formigenes strain hc-1, oxandrolone, oxaprozin, oxazepam, oxcarbazepine, oxiconazole, oxo-pentanoic acid methyl ester, oxprenolol, oxtriphylline, oxybutynin chloride, oxybutynin nicobrand, oxycodone, oxycodone, oxycodone; acetaminophen, oxycodone; apap, oxycodone; ibuprofen, oxymetazoline, oxymethalone, oxymorphone hydrochloride, oxytetracycline, oxytocin, p501, p53 and ras vaccine, paclitaxel, palifermin, palivizumab, palonosetron, palonosetron hydrochloride, paloxitene hcl, pam 4, pamelteon, pamidronate disodium, pancreatic enzymes, pancuronium, pancuronium bromide, pantoprazole sodium, papavereturn, papaverine, papiprazole, paracoxib, paracoxib sodium, parathyroid hormone, parecoxib sodium, paricalcitol, paromomycin sulfate, paroxetine, paroxetine hydrochloride, paroxetine mesylate, paxene, pazopanib, pazopanib hydrochloride, pbl and til transduced with retroviral vector-expressing anti-gp100 tcr, pbl or til transduced with retroviral vector-expressing anti-mart-1 tcr gene, pediazole, pegademase bovine, pegaptanib sodium, pegaspargase, pegfilgrastim, peginterferon alfa-2a, peginterferon alpha 2b, pegvisomant, pegylated arginine deiminase, pemetrexed disodium, pemirolast, pemoline, penbutolol, penciclovir, penfluridol, penicillamine, penicillin, penicillin g, penicillin n, penicillin o, penicillin s, penicillin v, pentamidine isethionate, pentazocine, pentazocine hydrochloride, pentazocine lactate, pentazocine; acetaminophen, pentetate calcium trisodium, pentetate zinc trisodium, pentobarbital, pentobarbital sodium, pentosan polysulfate sodium, pentostatin, pentoxifylline, peptide 144 tgf-betal-inhibitor, peptides, perflutren, perflutren protein-type a microspheres, pergolide mesylate, pericyazine, perindopril, perindopril, permethrin, perphenazine, persantine, personalized anti-cancer vaccine, pethidine, pexelizumab, pg-cpt, phenazocine, phendimetrazine tartrate, phenelzine, phenobarbital, phentermine, phentermine hydrochloride, phentolamine, phentolamine mesylate, phentytoin, phenyhydrazine, phenylephrine hydrochloride, phenyloin, phenyloin sodium, phosphodiesterase-5 inhibitor, pholine iodide, php, php pyridoxalated hemoglobin polyoxyethylene, physiologic saline solution, pilocarpine, pilocarpine hydrochloride, pimecrolimus, pimozide, pindolol, pioglitazone, pipamerone, piperacetazine, piperacillin, piperacillin sodium, piperacillin sodium/tazobactam sodium, pipotiazine, pirbuterol acetate, pirbuterolnaloxone, pirfenidone, piroxicam, pirprofen, pizotifen, plicamycin, pneumococcal vaccine polyvalent, pnu-166196, podofilox, polyeptides, polyethylene glycol, polyhematoporphyrin, polymyxin b sulfate, polypeptide yy, polysaccharide diphtheria toxoid conjugate vaccine, polythiazide, poractant alpha, porfimer sodium, posaconazole, potassium acetate, potassium chloride, potassium citrate, potassium iodide, povidone iodine, ppy 3-36, pralidoxime chloride, pramipexole, pramlintide acetate, pramoxine; hydrocortisone, prasterone, pravastatin, praziquantel, prazosin, prazosin; polythiazide, prednicarbate, prednisolone, prednisolone acetate, prednisolone sodium phosphate, prednisolone; gentamicin, prednisone, pregabalin, prentoxapylline, prilocalne, primaquine, primidone, pro 140, probenecid, probucol, procainamide hydrochloride, procaine, procaine hydrochloride, procarbazine, procaterol hcl, prochlorperazine, prochlorperazine edisylate, prochlorperazine maleate, procyclidine, progesterone, prolactin, prolifeprosan 20; carmustine, promazine, promethazine, promethazine hydrochloride, propacetamol, propafenone hydrochloride, propanedisulfonic acid, disodium salt, propanolol, propantheline bromide, proparacaine hydrochloride, propentofylline, propofol, propoxyphene, propoxyphene; acetaminophen, propranolol, propranolol hydrochloride, propylpiperidine×hcl, propylthiouracil, proscar, proscillaridin; verapamil, prosol, prostcyclin, protamine sulfate, proteinase 3 peptide vaccine, proteins, protriptyline, provocholine, prussian blue, psa: 154-163, pseudoephedrine hydrochloride, pseudomonas exotoxin-interleukin 13 chimeric protein, pseudophedrine; triprolidine, psma, pth 1-34, pulmonary surfactant, purified bromelain, purified inactivated japanese encephalitis sa14-4-2 virus vaccine, pyrazinamide, pyrethrin; piperinyl butoxide, pyridostigmine bromide, pyridoxine hydrochloride, pyrimethamine, quadravalent hpv vaccine, quazepam, quetiapine, quinapril, quinapril hydrochloride, quinapril; hctz, quinidine gluconate, quinidine sulfate, quinine, r1550, r744 cera, rabaprazole, rabies immune globulin, radiotheracim, raloxifene, ramipril, ramoplanin, ranibizumab, ranitidine, ranitidine hydrochloride, ranpirnase, rasagiline, rasburicase, rav 12, rdna hepatitis b vaccine, reboxetine, recombinant antibody derivative, recombinant dog gastric lipase, recombinant fusion protein, recombinant glycoprotein gp350 of epstein-barr virus, recombinant hepatitis b vaccine, recombinant histidine-tagged idiotype immunoglobulin fab fragment of clonal b-cell receptors, recombinant human acid alpha-glucosidase, recombinant human acid sphingomyelinase, recombinant human alpha-1-antitrypsin, recombinant human alpha-mannosidase, recombinant human arylsulfatase a, recombinant human bile salt-stimulated lipase, recombinant human c1-inhibitor, recombinant human factor xiii, recombinant human glucagon-like peptide, recombinant human insulin-like growth factor-i/recombinant human insulin-like growth factor binding protein-3, recombinant human interleukin-21, recombinant human monoclonal antibody to hsp90, recombinant human porphobilinogen deaminase, recombinant inhibitor of human plasma kallikrein, recombinant megakaryopoeisis-stimulating protein, recombinant methionyl human stem cell factor, recombinant microbial lipase, recombinant modified vaccinia virus ankara expressing tuberculosis antigen 85a, recombinant neuraminidase, recombinant p-selectin glycoprotein immunoglobulin, recombinant triple antigen hepatitis b vaccine, remacemide, remifentanil, remifentanil hydrochloride, remoxipride, remune hiv-1 immunogen, renal tumor-reactive autologous til and pbl, repaglinide, repertaxin l-lysine salt, rescinnamine, reserpine, resonium calcium, resten-mp, resten-ng, reteplase, retinol, retinol binding protein 4, retroviral gamma-c cdna containing vector, rfx111, rhbmp-2, rhcc10, rhlgfbp-3, rhmbl, rho(d) immune globulin, rhthrombin, ribavirin, rifabutin, rifampicin, rifampin, rifampin; isoniazid, rifampin; pyrazinamide; isoniazid, rifapentine, rifaximin, riluzole, rimantadine hydrochloride, rimexolone, rimonabant, ringer's, risperidone, ritanserin, ritodrine, ritodrine hydrochloride, ritonavir, rituximab, rivastigmine, rivastigmine tartrate, rizatriptan, rn1219, rn624, rocuronium bromide, ropinirole hcl, ropivacaine, roseglitazone, rosiglitazone, rosiglitazone; glimepiride, rosuvastatin, rotigotine, roxindole, rpa102, rpe cells with microcarriers, rubella virus vaccine, live, rubidium chloride rb-82, rubitecan, rufinamide, rx 0201, s. pneumoniae recombinant vaccine, sabarubicin, sacrosidase, s-adenosylmethionine, salbutamol, salicylate, salmeterol xinafoate, salmetrol, samarium sm 153 lexidronam pentasodium, samarium sm-153, sapropterin, saquinavir, sargramostim, sbil-2 transduced autologous til, scopolamine, secobarbital sodium, secretin, secretin synthetic human, secretin synthetic porcine, sehcat, selegiline, selegiline hydrochloride, selenious acid, selenium sulfide, sermorelin acetate, seromycin, serotonin, sertaconazole, sertindole, sertraline, sestamibi miraluma, sevelamer, sevoflurane, sfg, sgn-00101, sgn-30, sgn-33, sgn-40, sibrotuzumab, sibutramine, sildenafil, sildenafil citrate, silver nitrate, simplirix, simvastatin, sinapultide, dipalmitoylphosphatidylcholine, palmitoyloleoylphosphatidylglycerol and palmitic acid, sincalide, siplizumab, sipuleucel-t, sirolimus, sitaxentan sodium, sitaxsentan, sipi, sodium acetate, sodium aminohippurate, sodium benzoate/sodium phenylacetate, sodium bicarbonatee, sodium butabarbital, sodium butyrate, sodium chloride, sodium chromate, sodium dichloroacetate, sodium edecrin, sodium eglinide, sodium ferric gluconate, sodium ferric gluconate complex, sodium fluoride, sodium gluconate, sodium iodide, sodium iodide i 131, sodium lactate, sodium nitroprusside, sodium oxybate, sodium p.a.s., sodium phenylbutyrate, sodium phosphate, sodium polystyrene sulfonate, sodium tetradecyl sulfate, sodium valproate, solifenacin, soluble yeast beta-1,3/1,6-glucan, somatostatin, somatropin, somatropin (r dna), somatropin recombinant, sorafenib, sorafenib tosylate, sorbitol, sotalol, sotalol hydrochloride, spc+lipid, spectinomycin hydrochloride, spiperone, spironolactone, sps: sodium polystyrene sulfonate, ss1(dsfv)-pe38, ssd: silver sulfadiazine, stavudine, sterile diluent, sterile provocholine solution, sterile vancomycin hydrochloride, stiripentol, streptokinase, streptomycin sulfate, streptozocin, strontium chloride sr-89, strontium ranelate, suberoylanilide hydroxamic acid, succimer, succinylcholine chloride, sucralfate, sufentanil, sufentanil citrate, sulconazole nitrate, sulfacetamide sodium, sulfacetamide; prednisone, sulfadiazine, sulfadoxine; pyrimthamine, sulfamethoprim, sulfamethoxazole/trimethoprim, sulfasalazine, sulfentanil citrate, sulfinpyrazone, sulfisoxazole, sulindac, sulpiride, sumatriptan, sumatriptan succinate, sumitizib maleate, taci-Ig, tacrine, tacrolimus, tacrolimus hydrate, tadalafil, talc, tamoxifen citrate, tamsulosin hcl, tandospirone, tauferon, tazarotene, t-cell replacement therapy, technetium 99 monoclonal antibody, technetium fanolesomab, technetium tc 99m, technetium tc 99m tsc, technetium tc-99 generator, technetium tc-99m albumin, technetium tc-99m apcitide, technetium tc-99m bicisate, technetium tc-99m depreotide, technetium tc-99m disofenin, technetium tc-99m exametazime, technetium tc-99m gluceptate, technetium tc-99m mebrofenin, technetium tc-99m medronate, technetium tc-99m mertiatide, technetium tc-99m oxidronate, technetium tc-99m pentetate, technetium tc-99m pyrophosphate, technetium tc-99m red blood cell, technetium tc-99m sestamibi, technetium tc-99m succimer, technetium tc-99m sulfur colloid, technetium tc-99m tetrofosmin, teduglutide, tegaserod maleate, teicoplanin, telbivudine, telithromycin, telmisartan, telmisartan; hctz, telmisartan; hydrochlorothiazide, temazepam, temocillin sodium, temozolomide, temsirolimus, tenecteplase, teniparatide, teniposide, tenofovir, tenofovir; emtricitabine, terazosin hydrochloride, terbinafine, terbutaline, terbutaline sulfate, terconazole, terguride, teriparatide recombinant human, testalactone, testosterone, testosterone cypionate, testosterone enanthate, testosterone propionate, testosteroneacetate, testosteroneenanthate, testosteropropionate, tetanus and diphtheria toxoid, tetanus and diphtheria toxoids adsorbed, tetanus immune globulin, tetanus toxoid, reduced diphtheria toxoid and acellular pertussis vaccine, tetraazacyclotetradecane, tetracycline hydrochloride, tetracycline; metronidazole; bismuth subsalicylate, tetrahydrobiopterin, tetrahydrocannabinol, tetrahydrozoline, tetrahydrozoline hcl, tg 1042, tg 4001, tg 4010, tgaac94, tgaav-cf, tgf-β2 specific phosphorothioate antisense oligodeoxynucleotide, thalidomide, thallium chloride, thallous chloride, thallous chloride tl-201, thc; cbp, theophylline, thiabendazole, thiamine hydrochloride, thiethylperazine, thioguanine, thioridazine, thioridazine hydrochloride, thiotepa, thiothixene, thiothixene hydrochloride, thrombin (human), thrombopoietin, thromboxane, thymalfasin, thyroid-stimulating hormone, thyrotropin (tsh), thyrotropin alfa, thyrotropin-releasing hormone, thyroxine, tiagabine, tianeptine, tiaprofenic acid, ticarcillin disodium, ticilimumab, ticlopidine hydrochloride, tifacogin, tigecycline, tilarginine acetate, tiludronate disodium, timolol, timolol maleate, tinidazole, tioconazole, tiopronin, tiotropium bromide monohydrate, tipifarnib, tipranavir, tirofiban hydrochloride, tissue repair cells, titanium dioxide and bisoctrizole, tizanidine, tizanidine hydrochloride, tnf alpha la, tnx-355, tnx-650, tnx-832, tobramycin, tobramycin sulfate, tobramycin; dexamethasone, tofenacin, tolazamide, tolbutamide, tolcapone, tolevamer, gt160-246, tolfenamate, tolfenamicacid, tolmetin sodium, tolterodine tartrate, topical vegf, topiramate, topotecan hydrochloride, toremifene citrate, torsemide, tositumomab, tpl0, tpi-asm8, trabectedin, tradolapril; verapamil, trafermin, tramadol, tramadol; acetaminophen, trandolapril, tranexamic acid, tranylcypromine, trastuzumab, travoprost, travoprost; timolol, trazodone, trazodone hydrochloride, treosulfan, treprostinil, treprostinil sodium, tretinoin, triamcinolone acetonide, triamcinolone hexacetonide, triamterene, triamterene; hydrochlorothiazide, triazolam, tricarbocyanine, tridesilon, trientine dihydrochloride, trientine hcl, triethylperazine, trifluoperazine, trifluoperazine hydrochloride, trifluperidol, triflupromazine, trifluridine, trihexyphenidyl, trihexyphenidyl hydrochloride, triiodothyronine, trimeprazine, trimethadione, trimethobenzamide, trimethobenzamide hydrochloride, trimethoprim, trimethoprim sulfate, trimethorprim sulfate; polymyxin b sulfate, trimetrexate glucuronate, trimipramine, triodothyronine, tripelennamine, triprolidine hydrochloride, triptorelin pamoate, troleandomycin, tromethamine, tropicamide, tropisetron, trospium chloride, troxacitabine, trx 1, trx 4, trypan blue, tryptophan, tuberculosis recombinant vaccine, tucotuzumab celmoleukin, tumor necrosis tumor necrosis, ty800 yphoid fever vaccine, tykerb lapatinib, tyrosine, unoprostone, urea, urofollitropin, urokinase, ursodiol, urtoxazumab, valacyclovir, valdecoxib, valganciclovir, val-leugin-glu-leu-asn-val-thr-val, valproate sodium, valproicacid, valrubicin, valsartan, vancomycin, vandetanib, vardenafil, varenicline, varicella zoster virus recombinant vaccine, vascular endothelial growth factor 2, vasoactive intestinal peptide, vectibix, vecuronium bromide, vegf trap, veglin, velafermin, veldon lozenges, venlafaxine, verapamil, verapamil hydrochloride, verteporfin, vigabatrin, viloxazine, vinblastine, vinblastine sulfate, vincristine sulfate, vinorelbine, vinorelbine tartrate, vip, vitamin a acid, vitamin a palmitate, vitamin d, vitamin k, vitamin k1, voriconazole, vrc-hivadv 014-00-vp, vrx 496, vwf/fviii-concentrate, warfarin sodium, xaliproden hydrochloride, xenon, xtl 6865, y-fowlpox, r-vaccinia-tricom vaccine, y-fowipox-cea(6d) tricom vaccine, y-fowlpox-gm-csf vaccine, y-fowlpox-psa vaccine, yohimbine, yttrium (90y) antiferritin polyclonal antibodies, yttrium (90y) chloride, yttrium (90y) chloride, zafirlukast, zalcitabine, zaledronic acid, zaleplon, zalospirone, zanamivir, ziconotide, zidovudine, zileuton, zinc acetate, zinc acetate dehydrate, zinc acetate dihydrate, zinc chloride, ziprasidone, ziprasidone mesylate, zoledronic acid, zolmitriptan, zolpidem, zonisamide, zopiclone, zoster vaccine, zosuquidar trihydrochloride, zotepine, zuclopenthixol, zyc 101a, zyc 300, and combinations thereof.

Pharmaceutical Compositions

For administration to a subject, the albumin:active agent NPs can be provided in pharmaceutically acceptable (e.g., sterile) compositions. Accordingly, another aspect described herein is a pharmaceutical composition comprising a compound disclosed herein and a pharmaceutically acceptable carrier. These pharmaceutically acceptable compositions comprise an effective amount of one or more of the compounds described herein, formulated together with one or more pharmaceutically acceptable carriers (additives) and/or diluents. As described in detail below, the pharmaceutical compositions of the present disclosure can be specifically formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and/or systemic absorption), boluses, powders, granules, pastes for application to the tongue; (2) parenteral administration, for example, by subcutaneous, intramuscular, intravenous (e.g., bolus or infusion) or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. Nos. 3,773,919; and 3,270,960, content of all of which is herein incorporated by reference.

As used herein, the term "pharmaceutically acceptable" or "pharmacologically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Moreover, for animal (e.g., human) administration, it will be understood that compositions should meet sterility, pyrogenicity, general safety and purity standards as required by FDA Office of Biological Standards.

As used herein, the term "pharmaceutically acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alchols, such as ethanol; and (23) other non-toxic compatible substances employed in pharmaceutical formulations. Wetting agents, coloring agents, release agents, coating agents, disintegrating agents, binders, sweetening agents, flavoring agents, perfuming agents, protease inhibitors, plasticizers, emulsifiers, stabilizing agents, viscosity increasing agents, film forming agents, solubilizing agents, surfactants, preservative and antioxidants can also be present in the formulation. The terms such as "excipient", "carrier", "pharmaceutically acceptable carrier" or the like are used interchangeably herein.

Some Selected Definitions

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

For convenience, certain terms employed herein, in the specification, examples and appended claims are collected herein. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are useful to an embodiment, yet open to the inclusion of unspecified elements, whether useful or not.

As used herein and in the claims, the singular forms include the plural reference and vice versa unless the context clearly indicates otherwise. Thus, the singular terms "a," "an," and "the" include plural referents unless context clearly indicates otherwise. Similarly, the word "or" is intended to include "and" unless the context clearly indicates otherwise, for example, by "either."

As used herein, the term "herein" referres to the whole of the disclosure and is not limited to a specific section or subsection.

Other than in the operating examples, or where otherwise indicated, all numbers expressing quantities of ingredients or reaction conditions used herein should be understood as modified in all instances by the term "about." The term "about" when used in connection with percentages can mean ±5% of the value being referred to. For example, about 100 means from 95 to 105.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

As used herein, the term "bioavailability" generally means the rate and extent to which the active agent becomes available at the site of action.

It is to be understood that laser actuation can be in any form of light or radiation such as ultraviolet, visible, and/or infrared wavelengths. For example, laser actuation can be at wavelengths from at least 200 nm, 300 nm, 325 nm, or 340 nm to no greater than 900 nm, 800 nm, 750 nm, 600 nm, 500 nm or 400 nm.

The amount of active agent released from the nanoparticles can also be controlled by adjusting the amount of time the albumin:active agent NP is irradiated with the laser. For example, irradiation can range from seconds to hours. In some embodiments, irradiation can be from about 1 to about 60 minutes. For example, irradiation can be from about 1 second to about 55 minutes, from about 15 second to about 50 minutes, from about 30 second to about 45 minutes, from about 1 minute to about 40 minutes, from about 2 minutes to about 35 minutes, from about 3 minutes to about 30 minutes, from about 4 minutes to about 25 minutes, from about 5 minutes to about 20 minutes, from about 10 minutes to about 15 minutes.

As used herein, the term "low-power laser" refers to an energy density less than about 250 J/cm². For example, an energy density less than about 200 J/cm², less than about 175 J/cm², less than about 150 J/cm², less than about 125 J/cm², less than about 100 J/cm², less than about 75 J/cm², less than about 50 J/cm², less than about 25 J/cm², or less than about 10 J/cm². In some embodiments, low-power laser has an energy density of about 1 J/cm² to about 50 J/cm², about 1.5/cm² to about 40 J/cm², about 2 J/cm² to about 35 J/cm², about 2.5 J/cm² to about 30 J/cm².

The disclosure is further illustrated by the following examples which should not be construed as limiting. The examples are illustrative only, and are not intended to limit, in any manner, any of the aspects described herein. The following examples do not in any way limit the invention.

EXAMPLES

Example 1

Preparation of BSA NP and BSA NP TGF-β1 Conjugates

Reagents were purchased from the following sources: BSA (Fraction V, EMD Chemicals, Inc., San Diego, Calif., Lot #D00107504); 200 proof ethanol (Koptec, King of Prussia, Pa.); poly-L-lysine (Polysciences, Inc., Warrington, Pa.); 30% w/w H2O2 (VWR, West Chester, Pa.); Amplex UltraRed™ (N Acetyl-3,7,-dihydroxyphenoxazine, Molecular Probes, Invitrogen, Carlsbad, Calif.); IAEDANs (5-((2-[(iodoacetyl)amino]ethyl)amino)naphthalene-1-sulfonic acid), (Molecular Probes, Invitrogen, Carlsbad, Calif.); recombinant human TGF-β1 (R&D Systems, Minneapolis, Minn.); Alamar Blue (Invitrogen, Carlsbad, Calif.); DMEM Glutamax, FBS, Penicillin and Streptomycin (all from Gibco, Invitrogen, Carlsbad, Calif.); 2-mercaptoethanol (Sigma-Alridge, St. Louis, Mo.); GM-CSF (PeproTech, Rocky Hill, N.J.); lipopolysaccharide (LPS) (Sigma-Aldrich, St. Louis, Mo.); hydroxyapatite (HA) beads (Sigma-Aldrich, St. Louis, Mo.); and dithiothreitol (DTT) (NuPAGE® Sample Reducing Agent, Life Technologies, Invitrogen, Carlsbad, Calif.).

The BSA nanoparticles were prepared using an adapted and modified coacervation method from published literature. BSA solution (10 mg/mL) was mixed with equal volume of phosphate buffer solution (PBS, pH 7.4) for 15 min under constant stirring (500 rpm) at room temperature. The BSA solution was coacervated with ethanol at an 8:3 ethanol/albumin ratio (the final volume ratio of ethanol added to the initial amount of BSA solution) under constant stirring (500 rpm) at room temperature over 2 hours using an automatic pump controlled system (Model 55-5920, Harvard Apparatus, South Natick, Mass.). BSA nanoparticles were stabilized with 50 μg/mL PLL in phosphate buffer solution (pH 7.4) for 1 hr under constant stirring at 500 rpm at room temperature. Any large aggregates were removed using a 40 μm cell strainer (BD Biosciences, Durham, N.C.). To investigate the dependence of particle stability during dialysis, coated nanoparticles were dialyzed (MWCO: 3500 kDa, Spectrum Laboratories, Inc., Rancho Dominguez, Calif.) against 1 mM NaCl, PBS, or 1 M NaCl to remove non-adsorbed polymer and ethanol. The dialyzed buffer was exchanged every 18-24 hours for 3 days. After dialysis, BSA nanoparticles were lyophilized for 5 days in a freeze-dry system (Labconco, Kansas City, Mo.). BSA NPs were reconstituted in solvent 18%-20% w/w based on final lyophilized mass and stored in aqueous suspension at −20° C. until used.

Figure 5:
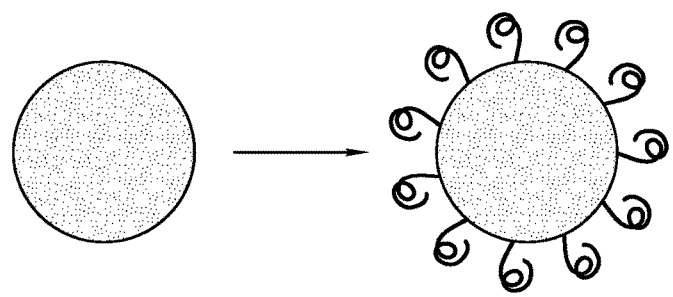
FIG. 5 presents a scheme for conjugating TGF-β1 with BSA NPs. TGF-β1 is conjugated to BSA NPs as a model payload.
Figure 6:
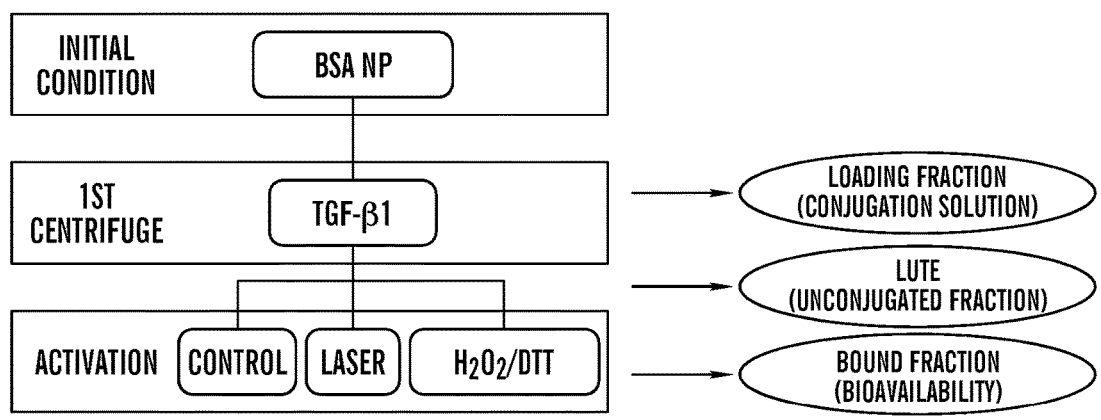
FIG. 6 illustrates an overview of BSA NP conjugation and experimental design.

Conjugation of TGF-β1 to BSA Nanoparticles: BSA NPs dialyzed against 1 M NaCl, reconstituted at 100 mg/mL, were conjugated with 3 ng/mL of recombinant human TGF-β1 by mixing at 4° C. overnight (FIG. 5). In order to remove the unconjugation fraction of TGF-β1, the nanoparticle solution was filtered (30K Microsep Advance centrifugal device, Pall Life Sciences, Ann Arbor, Mich.). The conjugated BSA:TGF-β1 NPs were resuspended in diH₂0 in the same volume. The liquid that passed through the centrifuge device is the unbound fraction. FIG. 6 shows the process of conjugation, spinning, and activating the BSA:TGF-β1 NPs for experiments.

BSA NPs embedded with TGF-β1 were fabricated using the same coacervation protocol as described herein, except for prior addition of TGF-β1 (3 ng/mL) with the BSA solution for 1 hr before coacervation. The remaining protocol was carried out as described herein.

Example 2

Characterization of BSA NPs

BSA NPs were characterized for their size and composition using a panel of techniques.

Dynamic Light Scattering: The mean particle size and polydispersity index of BSA NPs were determined using dynamic light scattering (DLS). Measurements were carried out using the Malvern Zetasizer Nano-ZS (Malvern Instruments, Worcestershire, United Kingdom) at 25° C. using a 633 nm laser at a scattering angle of 173°. NPs were diluted 1:50 in diluent with various solvents in a low volume cuvette (Sarstedt, Nümbrecht, Germany) right before measurement. The mean particle size value and polydispersity measurements were performed in triplicates.

Surface-Enhanced Ellipsometric Contrast: BSA NP samples (20 uL) were placed on SURF silicon oxide-coated microscope slides (Nanolane, Paris, France), allowed to dry, and imaged using an upright optical microscope (IX81 Olympus, Centerway, Pa.). SARFUS Mapping Lite (Nanolane, Paris, France) allowed for the conversion of a 2D SEEC images into a 3D map for complete topographic studies.

Phase Contrast Microscope: BSA NPs were diluted 1:50 in diluent and 20 μL of sample was added onto a slide. An IX81 Olympus microscope (Centerway, Pa.) with a water immersion lens was used to image the BSA NPs. As controls, HA beads of 200 nm were used.

Scanning Electron Microscopy and Energy-dispersive X-ray Spectroscopy: Samples of lyophilized BSA NPs were placed on SEM stubs coated with carbon tape (3M, Maplewood, Minn.). The samples were analyzed and imaged at room temperature by secondary electron emission SEM (Evo-55, Carl Zeiss, Thornwood, N.Y.) using an electron high tension (EHT) of 12.00 kV.

Energy-dispersive X-ray spectroscopy (EDS) (Bruker Optics, Billerica, Mass.) was used in conjunction with SEM to map the distribution of elements, in particular sodium and chloride, in the BSA NPs. EDS utilizes an electron beam inside a SEM to move electrons from their current energy levels to a high-energy state, which is accompanied by an X-ray emission. Each element release X-rays with unique amounts of energy during the electron transfer process and X-rays can be used to determine elemental composition of a sample. Ausserre & Valignat, 15 Opt. Express 8329 (2007).

Bradford Assay: The Pierce BCA Protein Assay (Thermo Fisher Scientific, Rockford, Ill.) was used to assess the presence of protein in aggregates and NP samples. BCA Protein Assay was made by combining Reagent A and B as per the manufacturer's instructions. Equal volumes of BCA Protein Assay and sample were added together. Color change from blue to purple was monitored to determine the presence of protein. A 10 mg/mL BSA solution was used as a positive control and PBS was used as a negative control.

Biocompatability: Alamar Blue was used to assess the in vitro toxicity of BSA NPs, both conjugated and embedded. Alamar Blue, used to measure cell viability, was diluted 10% into cell medium and placed on cells. Cells are incubated for 2-3 hr at 37° C. incubator and 5% $CO_2$. Media color changes from blue to pink-purple as resazurin, a non-fluorescent indicator dye, is converted to bright red-fluorescent resorufin via the reduction reactions of metabolically active cells. Fluorescence representing the metabolic activity is shown to represent cell viability. Samples of the media were read in a 96-well black well plate (Costar, Corning, N.Y.) at Ex/Em 520/590 using a microplate reader (Synergy HT, Bio-Tek Instruments, Winooski, Vt.).

Example 3

Low Power Laser Irradiation

A customized 810 nm GaAlAs laser diode system [Driver, Temperature controller and cooling mount] (all from Newport, Irvine, Calif.) with a fiberoptic delivery system was used for irradiation. The power density (irradiance, $W/cm^2$) was calibrated with a power meter (Newport, Irvine, Calif.) to achieve various energy densities (fluence, $J/cm^2$). The distance to irradiate target zone was varied based on the sample size and time (300 sec) was kept constant in all experiments.

Assessment of ROS Generation: ROS presence was assessed with a fluorescent dye, Amplex UltraRed™, which measures hydrogen peroxide ($H_2O_2$). BSA NPs were treated with $H_2O_2$ (10 mM) or laser irradiation (3 J/cm2) for five minutes. Samples were incubated with Amplex dye (10 mM) at 37° C. for 20 min. Fluorescence was assessed with a microplate reader (Synergy HT, Bio-Tek Instruments, Winooski, Vt.) in a 96-well black well plate (Costar, Corning, N.Y.) and concentrations were estimated from $H_2O_2$ standard curve.

Assessment of BSA NP Conformation Change: Free cysteines levels were assessed with a fluorescent dye, 5-((2-[(iodoacetyl)amino]ethyl)amino) naphthalene-1-sulfonic acid (IAEDANS), which binds free thiols, as a measure of protein conformational change due to ROS. BSA NPs were treated with $H_2O_2$ (10 mM) or laser irradiation (3 $J/cm^2$) for 5 min. Samples were incubated with IAEDANS dye (250 µM) at 37° C. for 30 min. Fluorescence was assessed with a microplate reader (Synergy HT, Bio-Tek Instruments, Winooski, Vt.) in a 96-well black well plate (Costar, Corning, N.Y.) and concentrations were estimated from a L-cysteine standard curve (Sigma-Aldrich, St. Louis, Mo.).

IAEDANs tagged samples separated by gel electrophoresis under native conditions based on charge:mass in 1D. Solutions were separated on a SDS reducing polyacrylamide gradient gel (4%-20% Tris-Glycine PAGE, Invitrogen, Carlsbad, Calif.). The gel was imaged on a UV transilluminator (365 nm, Hoefer, Hollistan, Mass.) to visualize tagged complex.

Assessment of Bioactivity TGF-β1 in BSA NP System: The activity of TGF-β1 in the BSA NP system was assessed with an ELISA (Promega, Madison, Wis.). The ELISA was performed as per the manufacturers' instructions. Briefly, solutions were incubated in microplate wells coated with the capture antibody followed by the secondary antibody and colorimetric substrate. Absorbance was read on a microplate reader at 450 nm with a wavelength correction at 540 nm (Synergy HT, Bio-Tek Instruments, Winooski, Vt.).

The bioactivity of TGF-β1 was also assessed in vitro by determining its ability to induce lucifrase activity in a TGF-β1 reporter cell line, a kind gift of Dan Rifkin, NYU Medical Center. Mv1Lu (Mink Lung Epithelium) cells stably transfected with p3TP-luciferase were maintained in 10% FBS, DMEM Glutamax, Penicillin (100 U/ml) and Streptomycin (100 µg/ml) at 37° C. incubator and 5% $CO_2$. Mv1Lu cells were plated in a 48-well plate (30,000 cells/well) (Nunc, Thermo Fisher Scientific, Waltham, Mass.) in complete media and allowed to attach for 4 hours before treatment. BSA:TGF-β1 NPs were subjected to laser irradiation at 3 $J/cm^2$ for 5 min. After actuation, the NPs were diluted 1:5 in 0.2% FBS media and incubated with the cells for 24 hr. Experiments were performed in the presence of 0.2% FBS media in order to reduce baseline luciferase activity because serum itself contains some basal active TGF-β1. As a control, cells were also treated with nanoparticles that did not undergo laser irradiation. After overnight incubation, cells were lysed in passive lysis buffer and luciferin substrate (both Promega, Madison, Wis.) was added to evaluate luciferase activity with a microplate reader (Synergy HT, Bio-Tek Instruments, Winooski, Vt.).

Assessment of BSA-TGF-β1 NPs as an Immune Modulator: To evaluate the possible utility of conjugated BSA:TGF-β1 nanoparticles as an immune modulator, a biological assay was designed. The assay used Secreted Embryonic Alkaline Phosphatase (SEAP) as a measure of inflammation in a macrophage cell line (RAW293). These cells express an NF-κB/AP-1-inducible SEAP reporter gene; therefore as more NF-κB is induced, increased SEAP will be secreted. Hence, ALP is used as a measure of NF-κB inflammatory activity. RAW293 were maintained in 10% FBS, DMEM Glutamax, Penicillin (100 U/ml) and Streptomycin (100 ug/ml) at 37° C. incubator and 5% $CO_2$. Cells were plated in a 48 well plate (40,000 cells/well) (Nunc, Thermo Fisher Scientific, Waltham, Mass.) in complete media for four hours to allow for cell attachment before the start of experimentation.

As positive controls, cells were exposed to one of four conditions in triplicates overnight: media (baseline), TGF-β1 (10 ng/mL), LPS (2 ng/mL), and LPS (2 ng/mL) plus TGF-β1 (10 ng/mL). Cells were also exposed to one of four conditions in triplicates overnight: BSA:TGF-β1 NPs (control), BSA:TGF-β1 NPs+LPS, laser-irradiated BSA:TGF-β1 NPs, laser-irradiated BSA:TGF-β1 NPs+LPS, where stimulation with LPS was always at 2 ng/mL. The BSA:TGF-β1 NPs were laser irradiated prior to being diluted 1:5 into the media and placed onto the cells. All experimental conditions were performed in the presence of 0.2% FBS media in order to reduce baseline activity since serum itself contains some basal active TGF-β1. The cells were incubated for 24 hr, and the condition media was collected. Levamisole (Invitrogen, Carlsbad, Calif.) was added to the condition media to reduce background from endogenous alkaline phosphaste. Lysis buffer (50 mM Tris HCl, 0.1% Triton X100, pH 9.5) was added to the sample. 4-Methylbelliferyl phosphate (4-MUP) substrate (Sigma-Aldrich, St. Louis, Mo.) was added and samples were incubated for 30 min at 37° C. Fluorescence was assessed at Em/Ex 360/440 with a microplate reader (Synergy HT, Bio-Tek Instruments, Winooski, Vt.) and concentrations were estimated with a standard curve using human alkaline phosphatase (Sigma-Aldrich, St. Louis, Mo.). Alamar Blue staining was performed to normalize the data to cell metabolic activity.

To further investigate the ability for this system for immune modulation, primary bone marrow dendritic cells (BMDCs) were isolated and cultured in RPMI 1640 (Gibco, Invitrogen, Carlsbad, Calif.) supplemented with and Penicillin (100 U/ml), Streptomycin (100 ug/ml), 10% FBS, 50 µM of 2-mercaptoethanol, and 20 ng/mL of GM-CSF. BMDCs at day 12 were seeded onto 24-well plates (Nunc, Thermo Fisher Scientific, Waltham, Mass.) at a concentration of 50,000 cells per well in RPMI 1640 media with only 3-10 ng/mL of GM-CSF for 4 hours to allow for cell attachment. To verify the system, cells were co-cultured with one of four conditions in triplicates overnight: media (baseline), TGF-β1 (2.5 ng/mL), LPS (2 ng/mL), and LPS (2 ng/mL with TGF-β1 (2.5 ng/mL). Primary BMDCs were exposed to one of five conditions in triplicates overnight: (1) BSA:TGF-β1 NPs (control); (2) BSA:TGF-β1 NPs+LPS; (3) laser-irradiated BSA:TGF-β1 NPs, (4) laser-irradiated BSA:TGF-β1 NPs at 3 J/cm$^2$+LPS, and (5) laser-irradiated BSA:TGF-β1 NPs at 30 J/cm$^2$+LPS, where stimulation with LPS was always at 2 ng/mL. All experimental conditions were in the presence of RPMI 1640 with only 0.2% FBS in order to reduce baseline activity since serum itself contains some basal active TGF-β1. The cells were incubated for 24 hr, and the condition media was collected. Levels of pro-inflammatory cytokines, TNF-α and IL-b, were quantified using Quantikine Colorimetric Sandwich ELISAs (R&D Systems, Minneapolis, Minn.). The ELISA was performed as per the manufacturers' instructions. Briefly, conditioned media were incubated with conjugated detection antibody followed by a colorimetric substrate and absorbance was assessed at 440 nm with a microplate reader (Synergy HT, Bio-Tek Instruments, Winooski, Vt.). Alamar Blue staining was performed to normalize the data to cell metabolic activity.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

What is claimed is:

1. A composition comprising a laser actuated serum albumin nanoparticle active agent conjugate, wherein the free cysteine concentration on the surface of the laser actuated nanoparticle active agent conjugate is higher than the free cysteine concentration on the surface of the nanoparticle active agent conjugate prior to laser actuation, and wherein the higher free cysteine on the surface of the nanoparticle active agent conjugate increases the bioavailability of the active agent as compared to the bioavailability of the active agent prior to laser actuation.

2. The composition of claim 1, wherein the serum albumin nanoparticle is prepared by ethanol coacervation.

3. The composition of claim 1, wherein the serum albumin nanoparticle and active agent are conjugated by adsorption.

4. The composition of claim 1, wherein the active agent is selected from the group consisting of a small organic or inorganic molecule; a saccharine; an oligosaccharide; a polysaccharide; a peptide; a protein; a peptide analog and derivative; a peptidomimetic; an antibody or antigen binding fragment thereof; a nucleic acid; a nucleic acid analog and derivative; an extract made from a biological material; an animal tissue; a naturally occurring or synthetic composition; and any combinations thereof.

5. The composition of claim 1, wherein the active agent is a cytokine.

6. The composition of claim 5, wherein the cytokine is TGF-β1.

7. The composition of claim 1, wherein the active agent is a growth factor.

8. The composition of claim 1, wherein the active agent is an anti-cancer agent.

9. The composition of claim 1, wherein the active agent is one useful in regenerative medicine.

10. The composition of claim 1, wherein the size of the nanoparticle ranges from 150 nm to 350 nm, inclusive.

11. The composition of claim 1, wherein the nanoparticle comprises from about 0.01% to about 99% (w/w) of the active agent.

12. The composition of claim 1, wherein the active agent is non-covalently adsorbed on the nanoparticle.

13. The composition of claim 1, wherein the active agent is covalently linked with the nanoparticle.

14. The composition of claim 1, wherein the free cysteine concentration on the surface of the laser actuated nanoparticle active agent conjugate is at least 1.2-fold higher than the free cysteine concentration on the surface of the nanoparticle active agent conjugate prior to laser actuation.

15. The composition of claim 1, wherein the diameter of the laser actuated serum albumin nanoparticle active agent conjugate is about 50 nm to about 750 nm.

16. The composition of claim 1, wherein the diameter of the laser actuated serum albumin nanoparticle active agent conjugate is about 100 nm to about 500 nm.

17. The composition of claim 1, wherein the diameter of the laser actuated serum albumin nanoparticle active agent conjugate is about 150 nm to about 450 nm.

* * * * *